(12) United States Patent
Nam et al.

(10) Patent No.: US 10,905,774 B2
(45) Date of Patent: Feb. 2, 2021

(54) NANOCAGE AND USE THEREOF

(71) Applicant: KOREA INSTITUTE OF SCIENCE AND TECHNOLOGY, Seoul (KR)

(72) Inventors: Gi Hoon Nam, Seoul (KR); Eun Jung Lee, Seoul (KR); Yoo Soo Yang, Seoul (KR); Cherl Hyun Jeong, Seoul (KR); In-San Kim, Seoul (KR); Kwangmeyung Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/247,937

(22) Filed: Jan. 15, 2019

(65) Prior Publication Data
US 2019/0216947 A1 Jul. 18, 2019

Related U.S. Application Data

(63) Continuation-in-part of application No. PCT/KR2017/007679, filed on Jul. 17, 2017.

(30) Foreign Application Priority Data

Jul. 15, 2016 (KR) ........................ 10-2016-0090233

(51) Int. Cl.
| | | |
|---|---|---|
| A61K 39/00 | (2006.01) | |
| A61K 47/00 | (2006.01) | |
| A61K 9/14 | (2006.01) | |
| A61K 39/12 | (2006.01) | |
| A61K 47/69 | (2017.01) | |
| A61K 31/704 | (2006.01) | |
| C07K 14/79 | (2006.01) | |
| C07K 14/47 | (2006.01) | |
| A61K 31/69 | (2006.01) | |
| A61K 9/51 | (2006.01) | |
| A61K 39/395 | (2006.01) | |
| A61P 35/00 | (2006.01) | |
| A61K 31/337 | (2006.01) | |
| B82Y 5/00 | (2011.01) | |
| B82Y 40/00 | (2011.01) | |
| C07K 14/005 | (2006.01) | |
| C07K 14/705 | (2006.01) | |
| C07K 14/785 | (2006.01) | |
| C07K 16/28 | (2006.01) | |

(52) U.S. Cl.
CPC ............ *A61K 47/6929* (2017.08); *A61K 9/51* (2013.01); *A61K 31/337* (2013.01); *A61K 31/69* (2013.01); *A61K 31/704* (2013.01); *A61K 39/395* (2013.01); *A61P 35/00* (2018.01); *B82Y 5/00* (2013.01); *B82Y 40/00* (2013.01); *C07K 14/005* (2013.01); *C07K 14/47* (2013.01); *C07K 14/70546* (2013.01); *C07K 14/785* (2013.01); *C07K 14/79* (2013.01); *C07K 16/2818* (2013.01)

(58) Field of Classification Search
CPC ........ A61K 39/00; A61K 39/12; A61K 39/39; A61K 47/6935; A61K 47/6937
See application file for complete search history.

(56) References Cited

U.S. PATENT DOCUMENTS

| | | | | |
|---|---|---|---|---|
| 7,964,196 B2* | 6/2011 | de los Rios | .......... | A61K 9/5184 424/189.1 |
| 2015/0329616 A1* | 11/2015 | Uger | ................ | C07K 14/70503 424/134.1 |

FOREIGN PATENT DOCUMENTS

| | | | |
|---|---|---|---|
| KR | 10-2013-0039672 A | | 4/2013 |
| KR | 20130039672 | * | 4/2013 |
| KR | 10-2015-0085721 A | | 7/2015 |
| WO | WO-2016-061231 A1 | | 4/2016 |

OTHER PUBLICATIONS

Liang et al., "H-ferritin-nanocaged doxorubicin nanoparticles specifically target and kill tumors with a single-dose injection," PNAS, vol. 111, No. 41, pp. 14900-14905 (Oct. 2014).

* cited by examiner

*Primary Examiner* — Barry A Chestnut
(74) *Attorney, Agent, or Firm* — Foley & Lardner LLP

(57) ABSTRACT

The present invention relates to a novel recombinant nanocage and use thereof wherein the nanocage is formed by self-assembly of a fusion protein including a phagocytosis enhancing protein and a self-assembling protein, and to a protein nanocage complex in which an immunogenic cell death inducer is loaded in the nanocage as an active ingredient.

27 Claims, 25 Drawing Sheets
Specification includes a Sequence Listing.

pT7-7 vector + *Nde* I – HisX6 – hFTH-H – *Xho* I – linker – *Hind* III– SIRP – *Cla* I 1: Expressed FH-SIRPα HV in BL21
2: BL21 (control)
3: Purified FH-SIRPα HV using Nickel affinity purification

- CT26.CL25 tumor bearing mice
- 28 mg/kg (0.7 mg)
- i.t. injection
- Two times every three days

SEQUENCE LISTING

```
<160> NUMBER OF SEQ ID NOS: 106

<210> SEQ ID NO 1
<211> LENGTH: 182
<212> TYPE: PRT
<213> ORGANISM: Homo sapiens

<400> SEQUENCE: 1

Thr Thr Ala Ser Thr Ser Gln Val Arg Gln Asn Tyr His Gln Asp Ser
1               5                   10                  15

Glu Ala Ala Ile Asn Arg Gln Ile Asn Leu Glu Leu Tyr Ala Ser Tyr
            20                  25                  30

Val Tyr Leu Ser Met Ser Tyr Tyr Phe Asp Arg Asp Asp Val Ala Leu
        35                  40                  45

Lys Asn Phe Ala Lys Tyr Phe Leu His Gln Ser His Glu Glu Arg Glu
    50                  55                  60

His Ala Glu Lys Leu Met Lys Leu Gln Asn Gln Arg Gly Gly Arg Ile
65                  70                  75                  80

Phe Leu Gln Asp Ile Lys Lys Pro Asp Cys Asp Asp Trp Glu Ser Gly
                85                  90                  95

Leu Asn Ala Met Glu Cys Ala Leu His Leu Glu Lys Asn Val Asn Gln
            100                 105                 110

Ser Leu Leu Glu Leu His Lys Leu Ala Thr Asp Lys Asn Asp Pro His
        115                 120                 125

Leu Cys Asp Phe Ile Glu Thr His Tyr Leu Asn Glu Gln Val Lys Ala
    130                 135                 140

Ile Lys Glu Leu Gly Asp His Val Thr Asn Leu Arg Lys Met Gly Ala
145                 150                 155                 160

Pro Glu Ser Gly Leu Ala Glu Tyr Leu Phe Asp Lys His Thr Leu Gly
                165                 170                 175

Asp Ser Asp Asn Glu Ser
            180

<210> SEQ ID NO 2
<211> LENGTH: 181
<212> TYPE: PRT
<213> ORGANISM: Mus musculus

<400> SEQUENCE: 2

Thr Thr Ala Ser Pro Ser Gln Val Arg Gln Asn Tyr His Gln Asp Ala
1               5                   10                  15

Glu Ala Ala Ile Asn Arg Gln Ile Asn Leu Glu Leu Tyr Ala Ser Tyr
            20                  25                  30

Val Tyr Leu Ser Met Ser Cys Tyr Phe Asp Arg Asp Asp Val Ala Leu
        35                  40                  45
```

```
Lys Asn Phe Ala Lys Tyr Phe Leu His Gln Ser His Glu Glu Arg Glu
     50                  55                  60

His Ala Glu Lys Leu Met Lys Leu Gln Asn Gln Arg Gly Gly Arg Ile
 65                  70                  75                  80

Phe Leu Gln Asp Ile Lys Lys Pro Asp Arg Asp Asp Trp Glu Ser Gly
                 85                  90                  95

Leu Asn Ala Met Glu Cys Ala Leu His Leu Glu Lys Ser Val Asn Gln
                100                 105                 110

Ser Leu Leu Glu Leu His Lys Leu Ala Thr Asp Lys Asn Asp Pro His
            115                 120                 125

Leu Cys Asp Phe Ile Glu Thr Tyr Tyr Leu Ser Glu Gln Val Lys Ser
            130                 135                 140

Ile Lys Glu Leu Gly Asp His Val Thr Asn Leu Arg Lys Met Gly Ala
145                 150                 155                 160

Pro Glu Ala Gly Met Ala Glu Tyr Leu Phe Asp Lys His Thr Leu Gly
                165                 170                 175

His Gly Asp Glu Ser
            180

<210> SEQ ID NO 3
<211> LENGTH: 181
<212> TYPE: PRT
<213> ORGANISM: Rattus norvegicus

<400> SEQUENCE: 3

Thr Thr Ala Ser Pro Ser Gln Val Arg Gln Asn Tyr His Gln Asp Ser
 1               5                  10                  15

Glu Ala Ala Ile Asn Arg Gln Ile Asn Leu Glu Leu Tyr Ala Ser Tyr
                20                  25                  30

Val Tyr Leu Ser Met Ser Cys Tyr Phe Asp Arg Asp Asp Val Ala Leu
             35                  40                  45

Lys Asn Phe Ala Lys Tyr Phe Leu His Gln Ser His Glu Glu Arg Glu
     50                  55                  60

His Ala Glu Lys Leu Met Lys Leu Gln Asn Gln Arg Gly Gly Arg Ile
 65                  70                  75                  80

Phe Leu Gln Asp Ile Lys Lys Pro Asp Arg Asp Asp Trp Glu Ser Gly
                 85                  90                  95

Leu Asn Ala Met Arg Cys Ala Leu His Leu Glu Lys Ser Val Asn Gln
                100                 105                 110

Ser Leu Leu Glu Leu His Lys Leu Ala Thr Asp Lys Asn Asp Pro His
            115                 120                 125

Leu Cys Asp Phe Ile Glu Thr His Tyr Leu Asn Glu Gln Val Lys Ser
            130                 135                 140

Ile Lys Glu Leu Gly Asp His Val Thr Asn Leu Arg Lys Met Gly Ala
145                 150                 155                 160

Pro Glu Ser Gly Met Ala Glu Tyr Leu Phe Asp Lys His Thr Leu Gly
                165                 170                 175

His Gly Asp Glu Ser
            180

<210> SEQ ID NO 4
<211> LENGTH: 170
<212> TYPE: PRT
<213> ORGANISM: Ovis aries

<400> SEQUENCE: 4
```

Thr Thr Ala Ser Pro Ser Gln Val Arg Gln Asn Tyr His Gln Asp Ser
1               5                   10                  15

Glu Ala Ala Ile Asn Arg Gln Ile Asn Leu Glu Leu Tyr Ala Ser Tyr
                20                  25                  30

Val Tyr Leu Ser Met Ser Tyr Tyr Phe Asp Arg Asp Asp Val Ala Leu
            35                  40                  45

Lys Asn Phe Ala Lys Tyr Phe Leu His Gln Ser His Glu Glu Arg Glu
        50                  55                  60

His Ala Glu Arg Leu Met Lys Leu Gln Asn Gln Arg Gly Ala Arg Ile
65                  70                  75                  80

Phe Leu Gln Asp Ile Lys Lys Pro Asp Arg Asp Trp Glu Asn Gly
                85                  90                  95

Leu Asn Ala Met Glu Cys Ala Leu Cys Leu Glu Arg Ser Val Asn Gln
                100                 105                 110

Ser Leu Leu Glu Leu His Lys Leu Ala Thr Glu Lys Asn Asp Pro His
            115                 120                 125

Leu Cys Asp Phe Ile Glu Thr His Tyr Leu Asn Gln Gln Val Glu Ala
        130                 135                 140

Ile Lys Glu Leu Gly Asp His Ile Thr Asn Leu Arg Lys Met Gly Ala
145                 150                 155                 160

Leu Trp Ile Gly His Gly Arg Val Pro Leu
                165                 170

<210> SEQ ID NO 5
<211> LENGTH: 180
<212> TYPE: PRT
<213> ORGANISM: Sus scrofa

<400> SEQUENCE: 5

Thr Thr Ser Cys Ser Ser Gln Val Arg Gln Asn Tyr His Gln Asp Ser
1               5                   10                  15

Glu Ala Ala Ile Asn Arg Gln Ile Asn Leu Glu Leu Tyr Ala Ser Tyr
                20                  25                  30

Val Tyr Leu Ser Met Ser Tyr Tyr Phe Asp Arg Asp Asp Val Ala Leu
            35                  40                  45

Lys Asn Phe Ala Lys Tyr Phe Leu His Gln Ser His Gly Gly Arg Gly
        50                  55                  60

His Ala Glu Lys Leu Met Lys Leu Gln Thr Gln Arg Gly Ala Arg Ile
65                  70                  75                  80

Phe Leu Gln Asp Ile Met Lys Pro Glu Arg Asp Asp Trp Glu Asn Gly
                85                  90                  95

Leu Thr Ala Met Glu Phe Ala Leu His Val Val Lys Asn Val Tyr Gln
                100                 105                 110

Ser Leu Leu Glu Leu His Lys Leu Ala Thr Asp Lys Asn Asp Pro His
            115                 120                 125

Leu Cys Asp Phe Ile Glu Thr His Tyr Leu His Glu Gln Val Lys Ala
        130                 135                 140

Ile Lys Glu Leu Gly Asp His Ile Thr Asn Leu His Arg Met Gly Ala
145                 150                 155                 160

Pro Glu Tyr Gly Met Ala Glu Tyr Leu Phe Asp Lys His Thr Leu Gly
                165                 170                 175

Ser Ser Glu Ser
            180

```
<210> SEQ ID NO 6
<211> LENGTH: 185
<212> TYPE: PRT
<213> ORGANISM: Cricetulus griseus

<400> SEQUENCE: 6

Thr Thr Thr Ala Leu Thr Thr Ala Ser Pro Ser Gln Val Arg Gln Asn
1               5                   10                  15

Tyr His Gln Asp Ser Glu Ala Ala Ile Asn Arg Gln Ile Asn Leu Glu
            20                  25                  30

Leu Tyr Ala Ser Tyr Val Tyr Leu Ser Met Ser Cys Tyr Phe Asp Arg
        35                  40                  45

Asp Asp Val Ala Leu Lys Asn Phe Ala Lys Tyr Phe Leu His Gln Ser
    50                  55                  60

His Glu Glu Arg Glu His Ala Glu Lys Leu Met Lys Leu Gln Asn Gln
65                  70                  75                  80

Arg Gly Gly Arg Ile Phe Leu Gln Asp Ile Lys Lys Pro Asp Arg Asp
                85                  90                  95

Asp Trp Glu Ser Gly Leu Asn Ala Met Glu Cys Ala Leu His Leu Glu
            100                 105                 110

Lys Ser Val Asn Gln Ser Leu Leu Glu Leu His Lys Leu Ala Thr Asp
        115                 120                 125

Lys Asn Asp Pro His Leu Cys Asp Phe Ile Glu Thr His Tyr Leu Asn
    130                 135                 140

Glu Gln Val Lys Ser Ile Lys Glu Leu Gly Asp His Val Thr Asn Leu
145                 150                 155                 160

Arg Lys Met Gly Ala Pro Glu Ala Gly Met Ala Glu Tyr Leu Phe Asp
                165                 170                 175

Lys His Thr Leu Gly His Ser Glu Ser
            180                 185

<210> SEQ ID NO 7
<211> LENGTH: 182
<212> TYPE: PRT
<213> ORGANISM: Macaca mulatta

<400> SEQUENCE: 7

Thr Thr Ala Ser Thr Ser Gln Val Arg Gln Asn Tyr His Gln Asp Ser
1               5                   10                  15

Glu Ala Ala Ile Asn Arg Gln Ile Asn Leu Glu Leu Tyr Ala Ser Tyr
            20                  25                  30

Val Tyr Leu Ser Met Ser Tyr Tyr Phe Asp Arg Asp Asp Val Ala Leu
        35                  40                  45

Lys Asn Phe Ala Lys Tyr Phe Leu His Gln Ser His Glu Glu Arg Glu
    50                  55                  60

His Ala Glu Lys Leu Met Lys Leu Gln Asn Gln Arg Gly Gly Arg Ile
65                  70                  75                  80

Phe Leu Gln Asp Ile Lys Lys Pro Asp Tyr Asp Asp Trp Glu Ser Gly
                85                  90                  95

Leu Asn Ala Met Glu Cys Ala Leu His Leu Glu Lys Asn Val Asn Gln
            100                 105                 110

Ser Leu Leu Glu Leu His Lys Leu Ala Thr Asp Lys Asn Asp Pro His
        115                 120                 125

Leu Cys Asp Phe Ile Glu Thr His Tyr Leu Asn Glu Gln Val Lys Ala
    130                 135                 140

Ile Lys Glu Leu Gly Asp His Val Thr Asn Leu Arg Lys Met Gly Ala
```

-continued

```
145                 150                 155                 160
Pro Glu Ser Gly Leu Ala Glu Tyr Leu Phe Asp Lys His Thr Leu Gly
                165                 170                 175

Asp Ser Asp Asn Glu Ser
            180

<210> SEQ ID NO 8
<211> LENGTH: 185
<212> TYPE: PRT
<213> ORGANISM: Bos taurus

<400> SEQUENCE: 8

Glu Pro Glu Pro Pro Leu Asn Pro Pro Lys Pro Ile Arg Gln Asn Tyr
1               5                   10                  15

Cys Pro Lys Cys Glu Ala Thr Val Asn Ser His Ala Ala Leu Glu Phe
            20                  25                  30

His Ala Ser Phe Gln Cys Leu Ala Met Ala Phe Tyr Leu Asp Cys Asp
        35                  40                  45

Asp Met Ala Leu Lys His Phe Ser Arg Phe Phe Leu Leu Cys Ser His
    50                  55                  60

Glu His Ser Glu Arg Ala Glu Asn Leu Leu Phe Leu Gln Asn Gln Arg
65                  70                  75                  80

Gly Gly Arg Thr Cys Phe Leu Asp Ile Arg Lys Pro Glu Thr Gln Gln
                85                  90                  95

Arg Glu Ser Gly Leu Gln Ala Met Gln Asp Ile Leu His Leu Glu Lys
            100                 105                 110

Cys Val Asn Gln Ser Leu Leu Asn Leu Tyr Gln Leu Ala Thr Asp Ser
        115                 120                 125

Ser Asp Ala His Leu Cys His Phe Leu Glu Thr His His Leu Asp Gln
    130                 135                 140

Gln Val Lys Phe Ile Lys Glu Leu Gly Tyr Val Ser Asn Leu Ser Asn
145                 150                 155                 160

Val Glu Ser Leu Glu Gly Ser Leu Ala Glu Tyr Val Phe Asp Lys Leu
                165                 170                 175

Thr Leu Gly Asp Gly Asp Lys Asn Asp
            180                 185

<210> SEQ ID NO 9
<211> LENGTH: 182
<212> TYPE: PRT
<213> ORGANISM: Gorilla gorilla

<400> SEQUENCE: 9

Thr Thr Ala Ser Thr Ser Gln Val Arg Gln Asn Tyr His Gln Asp Ser
1               5                   10                  15

Glu Ala Ala Ile Asn Ser Gln Ile Asn Leu Glu Leu Tyr Ala Ser Tyr
            20                  25                  30

Val Tyr Leu Ser Met Ser Tyr Tyr Phe Asp Arg Asp Asp Val Ala Leu
        35                  40                  45

Lys Asn Phe Ala Lys Tyr Phe Leu His Gln Ser His Glu Glu Arg Glu
    50                  55                  60

His Ala Glu Lys Leu Met Lys Leu Gln Asn Gln Arg Gly Gly Arg Ile
65                  70                  75                  80

Phe Leu Gln Asp Ile Lys Lys Pro Asp Cys Asp Asp Trp Glu Ser Gly
                85                  90                  95

Leu Asn Ala Met Glu Cys Ala Leu His Leu Glu Lys Asn Val Asn Gln
```

```
            100                 105                 110
Ser Leu Leu Glu Leu His Lys Leu Ala Thr Asp Lys Asn Asp Pro His
        115                 120                 125

Leu Cys Asp Phe Ile Glu Thr His Tyr Leu Asn Glu Gln Val Lys Ala
    130                 135                 140

Ile Lys Glu Leu Gly Asp His Val Thr Asn Leu Arg Lys Met Gly Ala
145                 150                 155                 160

Pro Glu Ser Gly Leu Ala Glu Tyr Leu Phe Asp Lys His Thr Leu Gly
                165                 170                 175

Asp Ser Asp Asn Glu Ser
            180

<210> SEQ ID NO 10
<211> LENGTH: 182
<212> TYPE: PRT
<213> ORGANISM: Pan paniscus

<400> SEQUENCE: 10

Thr Thr Ala Ser Thr Ser Gln Val Arg Gln Asn Tyr His Gln Asp Ser
1               5                   10                  15

Glu Ala Ala Ile Asn Arg Gln Ile Asn Leu Glu Leu Tyr Ala Ser Tyr
            20                  25                  30

Val Tyr Leu Ser Met Ser Tyr Tyr Phe Asp Arg Asp Asp Val Ala Leu
        35                  40                  45

Lys Asn Phe Ala Lys Tyr Phe Leu His Gln Ser His Glu Glu Arg Glu
    50                  55                  60

His Ala Glu Lys Leu Met Glu Leu Gln Asn Gln Leu Gly Gly Arg Ile
65                  70                  75                  80

Phe Leu Gln Asp Ile Lys Lys Pro Asp Cys Asp Asp Trp Glu Ser Arg
                85                  90                  95

Leu Asn Ala Met Glu Cys Ala Leu His Leu Glu Lys Asn Val Asn Gln
            100                 105                 110

Ser Leu Leu Glu Leu His Lys Leu Ala Thr Asp Lys Asn Asp Pro His
        115                 120                 125

Leu Cys Asp Phe Ile Glu Thr His Tyr Leu Asn Glu Gln Val Lys Ala
    130                 135                 140

Ile Lys Glu Leu Gly Asp Gln Val Thr Asn Leu Arg Lys Met Gly Ala
145                 150                 155                 160

Pro Glu Ser Gly Leu Ala Glu Tyr Leu Phe Asp Lys His Thr Leu Gly
                165                 170                 175

Asp Ser Asp Asn Glu Ser
            180

<210> SEQ ID NO 11
<211> LENGTH: 182
<212> TYPE: PRT
<213> ORGANISM: Pan troglodytes

<400> SEQUENCE: 11

Thr Thr Ala Ser Thr Ser Gln Val Arg Gln Asn Tyr His Gln Asp Ser
1               5                   10                  15

Glu Ala Ala Ile Asn Arg Gln Ile Asn Leu Glu Leu Tyr Ala Ser Tyr
            20                  25                  30

Val Tyr Leu Ser Met Ser Tyr Tyr Phe Asp Arg Asp Asp Val Ala Leu
        35                  40                  45

Lys Asn Phe Ala Lys Tyr Phe Leu His Gln Ser His Glu Glu Arg Glu
```

```
                 50                  55                  60

His Ala Glu Lys Leu Met Lys Leu Gln Asn Gln Arg Gly Gly Arg Ile
 65                  70                  75                  80

Phe Leu Gln Asp Ile Lys Lys Pro Asp Cys Asp Asp Trp Glu Ser Gly
                 85                  90                  95

Leu Asn Ala Met Glu Cys Ala Leu His Leu Glu Lys Asn Val Asn Gln
                100                 105                 110

Ser Leu Leu Glu Leu His Lys Leu Ala Thr Asp Lys Asn Asp Pro His
            115                 120                 125

Leu Cys Asp Phe Ile Glu Thr His Tyr Leu Asn Glu Gln Val Lys Ala
        130                 135                 140

Ile Lys Glu Leu Gly Asp His Val Thr Asn Leu Arg Lys Met Gly Ala
145                 150                 155                 160

Pro Glu Ser Gly Leu Ala Glu Tyr Leu Phe Asp Lys His Thr Leu Gly
                165                 170                 175

Asp Ser Asp Asn Glu Ser
            180

<210> SEQ ID NO 12
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 12

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro
        115

<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 13

Glu Glu Glu Val Gln Ile Ile Gln Pro Asp Lys Ser Val Ser Val Ala
 1               5                  10                  15
```

```
Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Ile Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro
        115

<210> SEQ ID NO 14
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha D1 domain

<400> SEQUENCE: 14

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro
        115

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 15

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45
```

-continued

```
Ile Tyr Asn Gln Arg Gln Gly Pro Phe Pro Arg Val Thr Thr Ile Ser
        50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (1)..(1)
<223> OTHER INFORMATION: Any amino acid

<400> SEQUENCE: 16

```
Xaa Leu Leu Phe Asn Lys Thr Lys Ser Val Glu Phe Thr Phe Gly Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Thr Arg
        115
```

<210> SEQ ID NO 17
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 17

```
Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Val Leu
            35                  40                  45
```

Ile Tyr Asn Gln Arg Gln Gly Pro Phe Pro Arg Val Thr Thr Ile Ser
            50                  55                  60

Glu Thr Thr Arg Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 18
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (1)..(1)
<223> OTHER INFORMATION: Any amino acid

<400> SEQUENCE: 18

Xaa Leu Leu Phe Asn Lys Thr Lys Ser Val Glu Phe Thr Phe Gly Asn
 1               5                  10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Ser Thr Arg
            115                 120

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 19

Glu Glu Glu Leu Gln Val Ile Gln Pro Asp Lys Ser Val Ser Val Ala
 1               5                  10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser

```
                50                  55                  60
Glu Ser Thr Lys Arg Glu Asn Met Asp Phe Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser Thr Arg
            115                 120

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 20

Glu Glu Glu Leu Gln Val Ile Gln Pro Asp Lys Ser Val Ser Val Ala
 1               5                  10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
                35                  40                  45

Ile Tyr Asn Gln Lys Glu Gly His Phe Pro Arg Val Thr Thr Val Ser
            50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser Thr Arg
            115                 120

<210> SEQ ID NO 21
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 21

Glu Glu Glu Leu Gln Val Ile Gln Pro Asp Lys Ser Val Ser Val Ala
 1               5                  10                  15

Ala Gly Glu Ser Ala Ile Leu His Cys Thr Ile Thr Ser Leu Ile Pro
                20                  25                  30

Val Gly Pro Ile Gln Trp Phe Arg Gly Ala Gly Pro Ala Arg Glu Leu
                35                  40                  45

Ile Tyr Asn Gln Arg Glu Gly His Phe Pro Arg Val Thr Thr Val Ser
            50                  55                  60

Glu Thr Thr Arg Arg Glu Asn Met Asp Phe Ser Ile Ser Ile Ser Asn
 65                  70                  75                  80
```

Ile Thr Pro Ala Asp Ala Gly Thr Tyr Tyr Cys Val Lys Phe Arg Lys
            85                  90                  95

Gly Ser Pro Asp Thr Glu Val Ser Gly Ala Gly Thr Glu Leu Ser
            100                 105                 110

Val Arg Ala Lys Pro Ser
            115

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 22

Glu Glu Glu Val Gln Val Ile Gln Pro Asp Lys Ser Val Ser Val Ala
1               5                   10                  15

Ala Gly Glu Ser Ala Ile Leu His Cys Thr Leu Thr Ser Leu Ile Pro
            20                  25                  30

Val Gly Pro Ile Gln Trp Phe Arg Gly Ala Gly Pro Ala Arg Val Leu
            35                  40                  45

Ile Tyr Asn Gln Arg Gln Gly His Phe Pro Arg Val Thr Thr Val Ser
        50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
            85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 23

Glu Glu Glu Val Gln Ile Ile Gln Pro Asp Lys Ser Val Ser Val Ala
1               5                   10                  15

Ala Gly Glu Ser Val Ile Leu His Cys Thr Ile Thr Ser Leu Thr Pro
            20                  25                  30

Val Gly Pro Ile Gln Trp Phe Arg Gly Ala Gly Pro Ala Arg Leu Leu
            35                  40                  45

Ile Tyr Asn Gln Arg Glu Gly Pro Phe Pro Arg Val Thr Thr Val Ser
        50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Leu Arg Lys
            85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 24
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 24

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Ser Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 25
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 25

Glu Glu Glu Ile Gln Val Ile Gln Pro Asp Lys Ser Val Ser Val Ala
1               5                   10                  15

Ala Gly Glu Ser Val Ile Ile His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Arg Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Val Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

```
<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 26

Glu Glu Glu Val Gln Ile Ile Gln Pro Asp Lys Ser Val Ser Val Ala
1               5                   10                  15

Ala Gly Glu Ser Ile Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Arg Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 27
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 27

Glu Glu Glu Val Gln Leu Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 28
<211> LENGTH: 119
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<223> OTHER INFORMATION: SiRP alpha variant

<400> SEQUENCE: 28

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 29
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: SiRP alpha variant

<400> SEQUENCE: 29

```
Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Leu Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

<210> SEQ ID NO 30
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: SiRP alpha variant

<400> SEQUENCE: 30

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Lys Gln Gly Pro Phe Pro Arg Val Thr Thr Ile Ser
50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 31
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 31

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Thr Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 32

Glu Glu Glu Leu Gln Val Ile Gln Pro Asp Lys Ser Val Leu Val Ala
1               5                   10                  15

-continued

```
Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 33
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: SiRP alpha variant

<400> SEQUENCE: 33

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

<210> SEQ ID NO 34
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: SiRP alpha variant

<400> SEQUENCE: 34

```
Glu Glu Glu Leu Gln Val Ile Gln Pro Asp Lys Ser Val Ser Val Ala
1               5                   10                  15

Ala Gly Glu Ser Ala Ile Leu Leu Cys Thr Val Thr Ser Leu Ile Pro
            20                  25                  30

Val Gly Pro Ile Gln Trp Phe Arg Gly Ala Gly Pro Ala Arg Glu Leu
        35                  40                  45
```

Ile Tyr Asn Gln Lys Glu Gly His Phe Pro Arg Val Thr Thr Val Ser
            50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 35

Glu Glu Gly Leu Gln Val Ile Gln Pro Asp Lys Ser Val Ser Val Ala
 1               5                  10                  15

Ala Gly Glu Ser Ala Ile Leu His Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 36
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 36

Glu Glu Glu Leu Gln Val Ile Gln Pro Asp Lys Phe Val Leu Val Ala
 1               5                  10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn

```
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 37

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Pro Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 38
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 38

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95
```

```
Gly Ser Pro Asp Thr Glu Phe Lys Ser Gly Ala Gly Thr Glu Leu Ser
            100                 105                 110

Val Arg Gly Lys Pro Ser
        115

<210> SEQ ID NO 39
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 39

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 40

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
50                  55                  60

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

```
<210> SEQ ID NO 41
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 41

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
```

```
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (104)..(104)
<223> OTHER INFORMATION: Any amino acid

<400> SEQUENCE: 42

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
```

<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 43

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 44
<211> LENGTH: 118
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 44

Glu Glu Glu Xaa Gln Xaa Ile Gln Pro Asp Lys Ser Val Ser Val Ala
1               5                   10                  15

Ala Gly Glu Ser Xaa Ile Leu Leu Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60
```

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid

```
<220> FEATURE:
<221> NAME/KEY: MOD_RES
<222> LOCATION: (104)..(104)
<223> OTHER INFORMATION: Any amino acid

<400> SEQUENCE: 45

Glu Glu Gly Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
```

<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (104)..(104)
<223> OTHER INFORMATION: Any amino acid

<400> SEQUENCE: 46

Glu Glu Glu Xaa Gln Xaa Ile Gln Pro Asp Lys Phe Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid

```
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (104)..(104)
<223> OTHER INFORMATION: Any amino acid

<400> SEQUENCE: 47

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Pro Ile Arg Ile Gly Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
```

```
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 48

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
            85                  90                  95
```

Gly Ser Pro Asp Thr Glu Xaa Lys Ser Gly Ala Gly Thr Glu Leu Ser
            100                 105                 110

Val Arg Gly Lys Pro Ser
        115

<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 49

-continued

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Ala Arg Xaa Leu
            35                  40                  45

Ile Tyr Asn Gln Xaa Xaa Gly Xaa Phe Pro Arg Val Thr Thr Val Ser
        50                  55                  60

Glu Xaa Thr Xaa Arg Glu Asn Met Asp Phe Ser Ile Ser Ile Ser Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:

```
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (104)..(104)
<223> OTHER INFORMATION: Any amino acid

<400> SEQUENCE: 50

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
50                  55                  60

Asp Xaa Thr Xaa Arg Asn Asn Met Asp Phe Ser Ile Arg Ile Ser Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
        100                 105                 110

Ser Val Arg Ala Lys Pro Ser
        115

<210> SEQ ID NO 51
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
```

```
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 51

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
```

```
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (65)..(66)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (70)..(70)
<223> OTHER INFORMATION: Any amino acid
<220> FEATURE:
<221> NAME/KEY: MOD_RES
<222> LOCATION: (75)..(75)
<223> OTHER INFORMATION: Any amino acid
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (79)..(80)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (101)..(102)
<223> OTHER INFORMATION: Any amino acid
```

```
<220> FEATURE:
<221> NAME/KEY: MOD_RES
<222> LOCATION: (104)..(104)
<223> OTHER INFORMATION: Any amino acid
<220> FEATURE:
<221> NAME/KEY: MOD_RES
<222> LOCATION: (116)..(116)
<223> OTHER INFORMATION: Any amino acid

<400> SEQUENCE: 52

Glu Glu Xaa Xaa Gln Xaa Ile Gln Pro Asp Lys Xaa Val Xaa Val Ala
1               5                   10                  15

Ala Gly Glu Xaa Xaa Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
    50                  55                  60

Xaa Xaa Thr Xaa Arg Xaa Asn Met Asp Phe Xaa Ile Xaa Ile Xaa Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Xaa Xaa Glu Xaa Lys Ser Gly Ala Gly Thr Glu Leu
            100                 105                 110

Ser Val Arg Xaa Lys Pro Ser
        115

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 53

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly His Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
```

```
                       polypeptide
<220> FEATURE:
<223> OTHER INFORMATION: SiRP alpha variant

<400> SEQUENCE: 54

Glu Glu Glu Val Gln Val Ile Gln Pro Asp Lys Ser Val Ser Val Ala
1               5                   10                  15

Ala Gly Glu Ser Ala Ile Leu His Cys Thr Leu Thr Ser Leu Ile Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly His Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 55

Glu Glu Glu Val Gln Ile Ile Gln Pro Asp Lys Ser Val Ser Val Ala
1               5                   10                  15

Ala Gly Glu Ser Val Ile Leu His Cys Thr Ile Thr Ser Leu Thr Pro
            20                  25                  30

Val Gly Pro Ile Gln Trp Phe Arg Gly Ala Gly Pro Ala Arg Leu Leu
        35                  40                  45

Ile Tyr Asn Gln Arg Glu Gly Pro Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 56
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 56
```

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Ser Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Lys Arg Glu Asn Met Asp Phe Ser Ile Ser Ile Ser Asn
65              70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: SiRP alpha variant

<400> SEQUENCE: 57

Glu Glu Glu Ile Gln Val Ile Gln Pro Asp Lys Ser Val Ser Val Ala
1               5                   10                  15

Ala Gly Glu Ser Val Ile Ile His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Arg Phe Pro Arg Val Thr Thr Val Ser
    50                  55                  60

Glu Gly Thr Lys Arg Glu Asn Met Asp Phe Ser Ile Ser Ile Ser Asn
65              70                  75                  80

Ile Thr Pro Ala Asp Ala Gly Thr Tyr Tyr Cys Val Lys Val Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
            115

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: SiRP alpha variant

<400> SEQUENCE: 58

Glu Glu Glu Val Gln Ile Ile Gln Pro Asp Lys Ser Val Ser Val Ala
1               5                   10                  15

Ala Gly Glu Ser Ile Ile Leu His Cys Thr Val Thr Ser Leu Phe Pro

```
            20                  25                  30

Val Gly Pro Ile Gln Trp Phe Arg Gly Ala Gly Pro Ala Arg Val Leu
        35                  40                  45

Ile Tyr Asn Gln Arg Glu Gly Arg Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
                115

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 59

Glu Glu Glu Val Gln Leu Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
                100                 105                 110

Val Arg Ala Lys Pro Ser
                115

<210> SEQ ID NO 60
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 60

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45
```

Ile Tyr Asn Gln Arg Gln Gly Pro Phe Pro Arg Val Thr Thr Val Ser
            50                  55                  60

Asp Thr Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 61

Glu Glu Glu Leu Gln Ile Ile Gln Pro Asp Lys Ser Val Ser Val Ala
  1               5                  10                  15

Ala Gly Glu Ser Ala Ile Leu His Cys Thr Ile Thr Ser Leu Phe Pro
                 20                  25                  30

Val Gly Pro Ile Gln Trp Phe Arg Gly Ala Gly Pro Ala Arg Leu Leu
             35                  40                  45

Ile Tyr Asn Gln Arg Gln Gly Pro Phe Pro Arg Val Thr Thr Val Ser
            50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 62

Glu Glu Glu Val Gln Ile Ile Gln Pro Asp Lys Ser Val Ser Val Ala
  1               5                  10                  15

Ala Gly Glu Ser Ala Ile Leu His Cys Thr Ile Thr Ser Leu Phe Pro
                 20                  25                  30

Val Gly Pro Ile Gln Trp Phe Arg Gly Ala Gly Pro Ala Arg Val Leu
             35                  40                  45

Ile Tyr Asn Gln Lys Gln Gly Pro Phe Pro Arg Val Thr Thr Ile Ser
            50                  55                  60

Glu Thr Thr Arg Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
        115

<210> SEQ ID NO 63
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SiRP alpha variant

<400> SEQUENCE: 63

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Thr Pro
                20                  25                  30

Val Gly Pro Ile Gln Trp Phe Arg Gly Ala Gly Pro Ala Arg Val Leu
            35                  40                  45

Ile Tyr Asn Gln Arg Gln Gly Pro Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
                100                 105                 110

Val Arg Ala Lys Pro Ser
        115

<210> SEQ ID NO 64
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SIRPaDI-Fc-VEGFRID2

<400> SEQUENCE: 64

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Ser Val Ala Ala Gly
            35                  40                  45

Glu Ser Ala Ile Leu His Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr

```
                100                 105                 110
Pro Ala Asp Ala Gly Thr Tyr Tyr Cys Val Lys Phe Arg Lys Gly Ser
            115                 120                 125

Pro Asp Thr Glu Phe Lys Ser Gly Ala Gly Thr Glu Leu Ser Val Arg
        130                 135                 140

Ala Lys Pro Ser Ala Pro Val Val Ser Gly Pro Ala Ala Arg Ala Thr
145                 150                 155                 160

Pro Gln His Glu Phe Glu Pro Lys Ser Cys Asp Lys Thr His Thr Cys
                165                 170                 175

Pro Pro Cys Pro Ala Pro Glu Leu Leu Gly Gly Pro Ser Val Phe Leu
            180                 185                 190

Phe Pro Pro Lys Pro Lys Asp Thr Leu Met Ile Ser Arg Thr Pro Glu
        195                 200                 205

Val Thr Cys Val Val Val Asp Val Ser His Glu Asp Pro Glu Val Lys
    210                 215                 220

Phe Asn Trp Tyr Val Asp Gly Val Glu Val His Asn Ala Lys Thr Lys
225                 230                 235                 240

Pro Arg Glu Glu Gln Tyr Asn Ser Thr Tyr Arg Val Val Ser Val Leu
                245                 250                 255

Thr Val Leu His Gln Asp Trp Leu Asn Gly Lys Glu Tyr Lys Cys Lys
            260                 265                 270

Val Ser Asn Lys Ala Leu Pro Ala Pro Ile Glu Lys Thr Ile Ser Lys
        275                 280                 285

Ala Lys Gly Gln Pro Arg Glu Pro Gln Val Tyr Thr Leu Pro Pro Ser
    290                 295                 300

Arg Asp Glu Leu Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Lys Leu Thr Val Asp Lys Ser Arg Trp Gln
        355                 360                 365

Gln Gly Asn Val Phe Ser Cys Ser Val Met His Glu Ala Leu His Asn
    370                 375                 380

His Tyr Thr Gln Lys Ser Leu Ser Leu Ser Pro Gly Lys Leu Glu Ile
385                 390                 395                 400

Ser Asp Thr Gly Arg Pro Phe Val Glu Met Tyr Ser Glu Ile Pro Glu
                405                 410                 415

Ile Ile His Met Thr Glu Gly Arg Glu Leu Val Ile Pro Cys Arg Val
            420                 425                 430

Thr Ser Pro Asn Ile Thr Val Thr Leu Lys Lys Phe Pro Leu Asp Thr
        435                 440                 445

Leu Ile Pro Asp Gly Lys Arg Ile Ile Trp Asp Ser Arg Lys Gly Phe
    450                 455                 460

Ile Ile Ser Asn Ala Thr Tyr Lys Glu Ile Gly Leu Leu Thr Cys Glu
465                 470                 475                 480

Ala Thr Val Asn Gly His Leu Tyr Lys Thr Asn Tyr Leu Thr His Arg
                485                 490                 495

Gln Thr Asn Thr Ile
            500

<210> SEQ ID NO 65
```

<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 65

Lys Glu Ser Gly Ser Val Ser Ser Glu Gln Leu Ala Gln Phe Arg Ser
1               5                   10                  15

Leu Asp

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 66

Glu Gly Lys Ser Ser Gly Ser Gly Ser Glu Ser Lys Ser Thr
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 67

Gly Ser Ala Gly Ser Ala Ala Gly Ser Gly Glu Phe
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 68

Cys Arg Arg Arg Arg Arg Arg Glu Ala Glu Ala Cys
1               5                   10

<210> SEQ ID NO 69
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: linker peptide

<400> SEQUENCE: 69

Ala Glu Ala Ala Ala Lys Glu Ala Ala Ala Lys Glu Ala Ala Ala Lys
1               5                   10                  15

```
Glu Ala Ala Ala Lys Ala Leu Glu Ala Glu Ala Ala Lys Glu Ala
             20                  25                  30

Ala Ala Lys Glu Ala Ala Ala Lys Glu Ala Ala Ala Lys Ala
         35                  40                  45

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 70

Gly Gly Gly Gly Gly Gly Gly Gly
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 71

Gly Gly Gly Gly Gly Gly
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 72

Gly Gly Gly Gly Ser
1               5

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 73

Ala Glu Ala Ala Ala Lys Glu Ala Ala Ala Ala Lys Ala
1               5                   10

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<223> OTHER INFORMATION: linker peptide

<400> SEQUENCE: 74

Pro Ala Pro Ala Pro
1               5

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 75

Val Ser Gln Thr Ser Lys Leu Thr Arg Ala Glu Thr Val Phe Pro Asp
1               5                   10                  15

Val

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 76

Pro Leu Gly Leu Trp Ala
1               5

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 77

Thr Arg His Arg Gln Pro Arg Gly Trp Glu
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 78

Ala Gly Asn Arg Val Arg Arg Ser Val Gly
1               5                   10

<210> SEQ ID NO 79
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 79

Arg Arg Arg Arg Arg Arg Arg Arg
1               5

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker peptide

<400> SEQUENCE: 80

Gly Phe Leu Gly
1

<210> SEQ ID NO 81
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: linker peptide

<400> SEQUENCE: 81

Gly Ser Ser Gly Gly Ser Gly Ser Ser Gly Gly Ser Gly Gly Gly Asp
1               5                   10                  15

Glu Ala Asp Gly Ser Arg Gly Ser Gln Lys Ala Gly Val Asp Glu
            20                  25                  30

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HisX6 tag

<400> SEQUENCE: 82

His His His His His His
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FLAG tag

<400> SEQUENCE: 83

Asp Tyr Lys Asp Asp Asp Lys
1               5
```

```
<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: V5 epitope tag

<400> SEQUENCE: 84

Gly Lys Pro Ile Pro Asn Pro Leu Leu Gly Leu Asp Ser Thr
1               5                   10

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Myc peptide

<400> SEQUENCE: 85

Glu Gln Lys Leu Ile Ser Glu Glu
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HA tag

<400> SEQUENCE: 86

Tyr Pro Tyr Asp Val Pro Asp Tyr Ala
1               5

<210> SEQ ID NO 87
<211> LENGTH: 546
<212> TYPE: DNA
<213> ORGANISM: Homo sapiens

<400> SEQUENCE: 87
acgaccgcgt ccacctcgca ggtgcgccag aactaccacc aggactcaga ggccgccatc     60
aaccgccaga tcaacctgga gctctacgcc tcctacgttt acctgtccat gtcttactac    120
tttgaccgcg atgatgtggc tttgaagaac tttgccaaat actttcttca ccaatctcat    180
gaggagaggg aacatgctga gaaactgatg aagctgcaga accaacgagg tggccgaatc    240
ttccttcagg atatcaagaa accagactgt gatgactggg agagcgggct gaatgcaatg    300
gagtgtgcat tacatttgga aaaaaatgtg aatcagtcac tactgaaact gcacaaactg    360
gccactgaca aaaatgaccc ccatttgtgt gacttcattg agacacatta cctgaatgag    420
caggtgaaag ccatcaaaga attgggtgac cacgtgacca acttgcgcaa gatgggagcg    480
cccgaatctg gcttggcgga atatctcttt gacaagcaca ccctgggaga cagtgataat    540
gaaagc                                                              546

<210> SEQ ID NO 88
<211> LENGTH: 93
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: polynucleotide encoding linker peptide

<400> SEQUENCE: 88
ggcagctctg gtggcagcgg tagctctggc ggtagcggcg gtggcgatga agcggacggt    60
agccgcggct ctcagaaagc gggtgtggat gaa                                93

<210> SEQ ID NO 89
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: polynucleotide encoding SiRP alpha variant

<400> SEQUENCE: 89
gaagaggagc tgcagatcat ccagcctgac aagtccgtgc tggtcgctgc tggtgaaact    60
gccactctgc gttgtacgat taccagcctg ttcccggtgg gtccaatcca gtggttccgt   120
ggtgctggtc cgggtcgtgt tctgatctac aaccagcgtc aaggtccgtt ccgcgtgta    180 actaccgtta gcgataccac gaagcgtaac aacatggact tttccatccg cattggcaat   240 attccccgg ccgacgcggg cacctactat tgcatcaaat ttcgcaaagg ctccccggat    300
gatgtagaat ttaaatctgg cgcaggcacc gaactgtctg ttcgcgcaaa accgtaa     357

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: beta-gal peptide

<400> SEQUENCE: 90

Thr Pro His Pro Ala Arg Ile Gly Leu
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AH1 peptide

<400> SEQUENCE: 91

Ser Pro Ser Tyr Val Tyr His Gln Phe
1               5

<210> SEQ ID NO 92
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: human wild type SIRP alpha

<400> SEQUENCE: 92

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro
        115

<210> SEQ ID NO 93
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: human wild type SIRP alpha

<400> SEQUENCE: 93
gaggaggaat tacaggtcat tcaaccagat aaatcggtct tagtagcagc cggagagaca      60
gctacattga gatgtacggc gacaagcctt attcccgtgg ggccgatcca atggtttcgc     120
ggggcaggcc ccggaagaga attgatttac aaccagaagg agggtcattt ccctcgcgtg     180
acgacggtca gcgacttaac taagcgtaat aacatggatt tttcaataag aataggcaat     240
ataactccgg ccgacgcagg gacgtactac tgtgttaaat tccggaaggg atctccggat     300
gatgtcgagt tcaaatctgg ggcgggtaca gaattgagcg ttcgggcaaa gccc           354

<210> SEQ ID NO 94
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: balb/c wild type SIRP alpha

<400> SEQUENCE: 94

Ala Thr Gly Thr Glu Val Lys Val Thr Gln Pro Glu Lys Ser Val Ser
1               5                   10                  15

Val Ala Ala Gly Asp Ser Thr Ile Leu Asn Cys Thr Val Thr Ser Leu
            20                  25                  30

Leu Pro Val Gly Pro Ile Arg Trp Tyr Arg Gly Val Gly Gln Ser Arg
        35                  40                  45

Leu Leu Ile Tyr Ser Phe Thr Gly Glu His Phe Pro Arg Val Arg Asn
    50                  55                  60

Val Ser Asp Thr Thr Lys Arg Asn Asn Met Asp Phe Ser Ile Arg Ile

```
                65                  70                  75                  80
Ser Asn Val Thr Pro Glu Asp Ala Gly Thr Tyr Tyr Cys Val Lys Phe
                        85                  90                  95

Gln Arg Gly Ser Ser Glu Pro Asp Thr Glu Ile Gln Ser Gly Gly Gly
            100                 105                 110

Thr Glu Val Tyr Val Leu Ala
        115

<210> SEQ ID NO 95
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: balb/c wild type SIRP alpha

<400> SEQUENCE: 95
gcgaccggta cggaagtgaa agtgactcag ccggagaaga gcgtgagtgt ggccgcgggc     60
gactctacca ttctgaattg tacggtgact tccctgttac cagtgggccc gattcgttgg    120
tatcgtggtg tgggccaaag ccgcctgttg atctacagtt ttaccggtga acattttcca    180
cgtatccgta acgtgtctga tacgactaaa cgcaataaca tggacttctc cattcgtatc    240
agcaatgtga ccccggagga tgccggcacg tattactgcg tgaagtttca gcgcggtagt    300
tctgaaccag atactgagat tcaaagtggt ggcggtaccg aagtgtatgt gctggcg       357

<210> SEQ ID NO 96
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: variant SIRP alpha

<400> SEQUENCE: 96

Glu Glu Glu Leu Gln Ile Ile Gln Pro Asp Lys Ser Val Leu Val Ala
1               5                  10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro
        115

<210> SEQ ID NO 97
<211> LENGTH: 354
<212> TYPE: DNA
<213> ORGANISM: Artificial Sequence
<220> FEATURE:
```

<223> OTHER INFORMATION: Description of Artificial Sequence: Synthetic
      polynucleotide
<220> FEATURE:
<223> OTHER INFORMATION: variant SIRP alpha

<400> SEQUENCE: 97

```
gaagaggagc tgcagatcat ccagcctgac aagtccgtgc tggtcgctgc tggtgaaact    60
gccactctgc gttgtacgat taccagcctg ttcccggtgg gtccaatcca gtggttccgt   120
ggtgctggtc cgggtcgtgt tctgatctac aaccagcgtc aaggtccgtt cccgcgtgta   180
actaccgtta gcgataccac gaagcgtaac aacatggact tttccatccg cattggcaat   240
attccccgg ccgacgcggg cacctactat tgcatcaaat tcgcaaagg ctccccggat    300
gatgtagaat ttaaatctgg cgcaggcacc gaactgtctg ttcgcgcaaa accg         354
```

<210> SEQ ID NO 98
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: wild type SIRP gamma

<400> SEQUENCE: 98

Glu Glu Glu Leu Gln Met Ile Gln Pro Glu Lys Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser
        115

<210> SEQ ID NO 99
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: wild type SIRP gamma

<400> SEQUENCE: 99

```
gaggaagaat tgcaaatgat ccagccggaa aaattattac tggttaccgt gggaaaaacg    60
gcgacccttc attgcacagt cacgtccctg ttgccggtag gtccagtttt gtggttccgg   120
ggggttggac cagggcgtga actgatctat aatcaaaagg aaggtcattt cccgcgcgtg   180
accacagtga gcgatttgac taaacggaac aatatggact ctcgatccg catttctagt    240
attacaccgg cggacgttgg cacttattat tgcgtcaagt tccgcaaagg aagtcctgag   300
```

```
aacgtagagt tcaagtccgg tcctggcact gagatggctt tgggtgctaa accc      354
```

<210> SEQ ID NO 100
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: variant SIRP gamma

<400> SEQUENCE: 100

Glu Glu Glu Leu Gln Ile Ile Gln Pro Glu Lys Leu Leu Leu Val Thr
1               5                   10                  15

Val Gly Lys Thr Ala Thr Leu His Cys Thr Val Thr Ser Leu Phe Pro
            20                  25                  30

Val Gly Pro Val Leu Trp Phe Arg Gly Val Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro
        115

<210> SEQ ID NO 101
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: variant SIRP gamma

<400> SEQUENCE: 101

```
gaagaggaat tacaaatcat acaacctgaa aagctgttat tggtcaccgt aggcaaaacc      60
gctactctgc actgcactgt gacgtcccct tttcctgttg gtcctgtctt atggtttcgt     120
ggagtcggtc cgggtcgggt tcttatctat aaccagcggc aaggaccatt cccacgggtt     180
accacggttt cggacacaac gaaacgcaat aacatggatt tttccattcg gatttcaagc     240
atcactccgg ccgacgttgg aacttattac tgcataaagt ttagaaaggg atctccggag     300
aacgtagaat ttaagtctgg tccaggtact gagatggccc ttggagcgaa gccg           354
```

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Gly Gly Ser
1               5

```
<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ser Ser Gly Gly Ser
1               5

<210> SEQ ID NO 104
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Ala Ala Ala Lys Glu Ala Ala Ala Lys Glu Ala Ala Ala Lys Glu
1               5                   10                  15

Ala Ala Ala Lys
            20

<210> SEQ ID NO 105
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (124)..(186)

<400> SEQUENCE: 105
cgattcgaac ttctcgattc gaacttctga tagacttcga aattaatacg actcactata    60
gggagaccac aacggtttcc ctctagaaat aattttgttt aactttaaga aggagatata   120 cat atg gct aga att cgc gcc cgg gga tcc tct aga gtc gac ctg cag    168
    Met Ala Arg Ile Arg Ala Arg Gly Ser Ser Arg Val Asp Leu Gln
    1               5                   10                  15 ccc aag ctt atc atc gat                                             186
Pro Lys Leu Ile Ile Asp
                20

<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Met Ala Arg Ile Arg Ala Arg Gly Ser Ser Arg Val Asp Leu Gln Pro
1               5                   10                  15

Lys Leu Ile Ile Asp
            20
```

NANOCAGE AND USE THEREOF

CROSS-REFERENCE TO RELATED APPLICATIONS

The present application is a Continuation-In-Part of International Application PCT/KR2017/007679, filed Jul. 17, 2017, and claims priority to Korean Patent Application No. 10-2016-0090233 filed Jul. 15, 2016.

SEQUENCE LISTING

The instant application contains a Sequence Listing which has been filed electronically in ASCII format and is hereby incorporated by reference in its entirety. Said ASCII copy, created on Mar. 28, 2019, is named 115518-0108_SL.txt and is 115,916 bytes in size.

BACKGROUND

The present invention relates to a novel recombinant nanocage and use thereof.

Methods for treating cancer include surgery, radiotherapy, and chemotherapy. However, these treatments may be accompanied by side effects or applied limitedly depending on cancer progression. In particular, the number of anti-cancer drugs has been increased in terms of quantity, but there has been no significant change in terms of quality. The reason for this is that most of the anti-cancer drugs act as a mechanism to stop cell cycle and induce death of cells whose proliferation are vigorous. Thus, in addition to cancer cells, they attack normal dividing cells and cause side effects such as hair loss, poor appetite and a decrease in immunity due to leukocyte depletion. Doxorubicin, a typical anti-cancer drug, is a chemotherapeutic compound belonging to the family called anthracyclines. Anthracyclines inhibit cell division by acting on cell cycle selectively, and are used for treating various cancers such as malignant lymphoma (lymphosarcoma, Hodgkin's lymphoma, and non-Hodgkin's lymphoma), gastrointestinal cancer (stomach cancer, liver cancer, rectal cancer, gall bladder cancer, colon cancer, pancreatic cancer), acute myelogenous leukemia, soft tissue osteosarcoma, breast cancer, ovarian cancer, lung cancer, bronchial cancer, bladder cancer and Wilm's tumor, etc. Recent studies have shown that anthracyclines induce immunogenic cell death of cancer cells by inducing preapoptotic translocation of calreticulin to cell membranes (Obeid et al., *Nat. Med.*, 13(1): 54-61, 2007). In the meantime, the above-mentioned cancer treatment strategy through the enhancement of immune function has been attracting attention recently. Studies of the relationship between immune cells and cancer have begun around the world in the 1970s and have grown exponentially since 2000. According to the results of these researches, the functions of immune cells, which are the biological weapons capable of fighting against cancer, have become very important. The importance of anti-cancer immunotherapy research is emerging, as indicated by Keytruda® (Pembrolizumab, developed by Merck), an anti-cancer immunotherapy antibody, which was received accelerated approval through FDA in September 2014. In particular, since the immune cells patrol and search for and move against cancer cells, the effect is not limited to locally, but it can be applied to various cancer cells as well as to monitor and inhibit the onset of cancer in the whole body. Therefore, it is necessary to present a new paradigm of cancer prevention and treatment strategies that overcome cancer microenvironment by controlling the dynamic networking of immune cells in the human body, away from the conventional approach of focusing on existing cancer cell necrosis.

SUMMARY

The present disclosure aims to solve various problems including the above problems, and it is an object of the present invention to provide an immunotherapeutic agent capable of maximizing the cancer immunotherapy efficiency through induction of immunogenic cell death and control of immune cell networking, and use thereof. However, these problems are exemplary and do not limit the scope of the present invention.

According to one aspect of the present invention, there is provided a pharmaceutical composition comprising a nanocage formed by self-assembly of a fusion protein comprising a phagocytosis enhancing protein and a self-assembling protein, or a nanocage complex in which an immunogenic cell death inducer is encapsulated in the nanocage as an active ingredient.

According to one aspect of the present invention, there is provided a pharmaceutical composition comprising a hybrid nanocage formed by self-assembly of a first fusion protein comprising a phagocytosis enhancing protein and a self-assembling protein, and a second fusion protein comprising a single chain-based antibody analogue targeting an immune checkpoint, and the self-assembling protein or a hybrid nanocage complex in which an immunogenic cell death inducer is encapsulated in the hybrid nanocage as an active ingredient.

According to another aspect of the present invention, there is provided a fusion protein in which a signal-regulatory protein alpha (SIRP alpha) or a SIRP gamma is linked to the N-terminal or C-terminal of a ferritin heavy chain protein.

According to another aspect of the present invention, there is provided a polynucleotide encoding the fusion protein.

According to another aspect of the present invention, there is provided a vector comprising the polynucleotide.

According to another aspect of the present invention, there is provided a transformed host cell prepared by transforming a host cell with the vector.

According to another aspect of the present invention, there is provided a protein nanocage formed by self-assembly of the fusion protein.

According to another aspect of the present invention, there is provided an anticancer protein nanocage complex in which an immunogenic cell death inducer is encapsulated in the protein nanocage.

According to another aspect of the present invention, there is provided is pharmaceutical composition for the treatment of cancer comprising the protein nanocage or the anticancer protein nanocage complex as an active ingredient.

BRIEF DESCRIPTION OF THE DRAWINGS

FIG. 1C discloses the nucleotide sequence of SEQ ID NO: 105, the peptide sequence of SEQ ID NO: 106, and "HisX6" of SEQ ID NO: 82.

FIG. 5A is a series of fluorescence microscopic images of cancer cells treated with FH-SIRPα nanocages or wtFH nanocages in order to investigate whether the FH-SIRPα HV nanocage prepared in Example 1-1 binds to various cancer cells (CT26 mouse colon cancer cells (upper) and HT29 human colon cancer cells (lower)), and FIG. 5B is a graph showing the results of flow cytometry analysis of the binding activity of various ferritin heavy chain nanocages prepared in Examples 1-1 to 1-5 to HT29 human colorectal cancer cells.

FIG. 6A is a graph representing flow cytometry analysis showing phagocytosis rate of bone marrow-derived macrophages (BMDMs) co-cultured with various cancer cells (Raji cells, HT29 cells, 4T1 cells, CT26 cells and CT26.CL25 cells), after treating nanocages according to an embodiment of the present invention (FH-SIRPα HV) to the BMDMs. As negative controls, buffer only, nanocages produced by wild-type ferritin heavy chain protein (wtFH), and recombinant SIRPα proteins (mSIRPα) were used, respectively. FIG. 6B is a graph representing the results of flow cytometry analysis showing the phagocytosis rate by the bone marrow-derived dendritic cells (BMDCs) co-cultured with various cancer cells (Raji cells, HT29 cells, 4T1 cells, CT26 cells and CT26.CL25 cells), after treating nanocages according to one embodiment of the present invention (FH-SIRPα HV). As negative controls, buffer only, nanocages produced by wild-type ferritin heavy chain protein (wtFH), and recombinant SIRPα proteins (mSIRPα) were used, respectively, while culturing with Raji cells, HT29 cells, 4T1 cells, CT26 cells and CT26.CL25 cells. FIG. 6C is a series of fluorescence microscopic images showing the phagocytosis of HT29 cells by BMDMs. FIG. 6D is a graph showing the phagocytosis rate of CT26.CL25 mouse colon cancer cells by bone marrow-derived macrophages treated with various ferritin heavy chain nanocages prepared in Examples 1-2 to 1-5. FIG. 6E is a graph showing the phagocytosis index (PI) as a percentage of the number of HT29 cells per BMDM cell counted by microscopic observation in FIG. 6C. FIG. 6F is a histogram showing the differentiation of bone marrow-derived dendritic cells (BMDCs) from C57BL/6 mice for phagocytosis. FIG. 6G is a FACS plots representing phagocytosis of B16.OVA cells by BMDCs treated with buffer only (control), FH-SIRPα HV, wtFH, and mSIRPα, respectively. FIG. 6H is a graph analysis showing phagocytosis rate of B16.OVA cells by bone marrow-derived dendritic cells (BMDCs) treated with buffer only (control), FH-SIRPα HV, wtFH, and mSIRPα, respectively.

FIG. 7A shows the schedule of tumor transplantation and administration of the ferritin heavy chain nanocage therapeutics prepared in Examples 1-1 to 1-5 of the present invention, and FIG. 7B is a graph representing the results of measuring the tumor size over time in experimental animals prepared by tumor transplantation, after administrating the nanocages prepared in Examples 1-1 to 1-3 and 1-5 (FH-mSIRPα WT, FH-SIRPα HV, FH-SIRPγ WT and FH-SIRPγ V2). FIG. 7C is a graph showing the weight of the tumor tissue extracted after sacrifice of the experimental animals, FIG. 7D shows the schedule of tumor transplantation and administration of the ferritin heavy chain nanocage complex prepared in Example 3 (FH-SIRPα HV-Dox). FIG. 7E is a graph showing the results of measuring the tumor size over time in experimental animals prepared by tumor transplantation after administrating buffer only (control), doxorubin only (dox), wild-type ferritin heavy chain nanocage loaded with doxorubicin (wtFH-dox), combination of recombinant SIRPα and doxorubicin (mSIRPα+dox) and the nanocage complexes encapsulating doxorubicin prepared in Examples 3 (FH-SIRPα HV-Dox), respectively.

FIG. 7F is a series of photographic images of tumors, 25 days after drug administration (left-side panel) and tumor transplantation (right-hand panel) in experimental animals of FIG. 7E injected with buffer only or nanocage complex encapsulating doxorubicin (FH-SIRPα HV-Dox) according to an embodiment of the present invention. FIG. 7G is a graph representing weight of tumor tissues extracted from the experimental animals of FIG. 7E, 25 days after the formation of tumor.

FIG. 8A and FIG. 8B are a series of fluorescence microscopic images of CD8$^+$ T cells stained specially. FIG. 8C is a graph showing the results of measuring the expression level of INF-γ upon treatment of various effect peptides on cancer antigen-specific INF-γ-secreting effector cells among splenocytes. FIG. 8D is a series of histogram representing the results of the measurement of priming ability of various substances including FH-SIRPα to CD8$^+$ T cells by administrating buffer only, nanocage complex encapsulating doxorubicin according to an embodiment of the present invention (FH-SIRPα HV-Dox), doxorubicin only (DOX), ferritin nanocage presenting SIRPα according to an embodiment of the present invention (FH-SIRPα).

FIG. 9A is a graph showing the percentage of tumor-free mice in which the primary tumor tissues of the experimental animals was surgically removed and transplanted to the other side to induce secondary cancer and then the cancerous part is not grown in the corresponding area. FIG. 9B is a graph showing a survival rate of the experimental animals up to 80 days, FIG. 9C is a series of photographic images showing the growth state of the secondary tumor of the experimental animals administrated with a buffer only (left panel) and nanocage complex encapsulating doxorubicin according to an embodiment of the present invention (FH-SIRPα HV-Dox, right panel), respectively.

FIG. 10A is a series of near-infrared fluorescence images taken from tumor model mice administrated with doxorubicin-encapsulated nanocage complex (FH-SIRPα HV-Dox), doxorubicin-encapsulated wild-type ferritin nanocage (wtFH-dox), recombinant SIRPα (mSIRPα) and combination of recombinant SIRPα and doxorubicin (mSIRPα+dox), respectively, over time. FIG. 10B is a graph showing the fluorescence intensity of the tumor region of the experimental animals of FIG. 10A over time. FIG. 10C is a series of photographs showing the near-infrared fluorescence image of the main organs and tumor tissues extracted from the experimental animals of FIG. 10A. FIG. 10D is a graph showing fluorescence intensity of a tumor at 24 hours after injection of each drug in the experimental animals of FIG. 10A.

DETAILED DESCRIPTION OF EMBODIMENTS

Definition of Terms

Figure 1A:
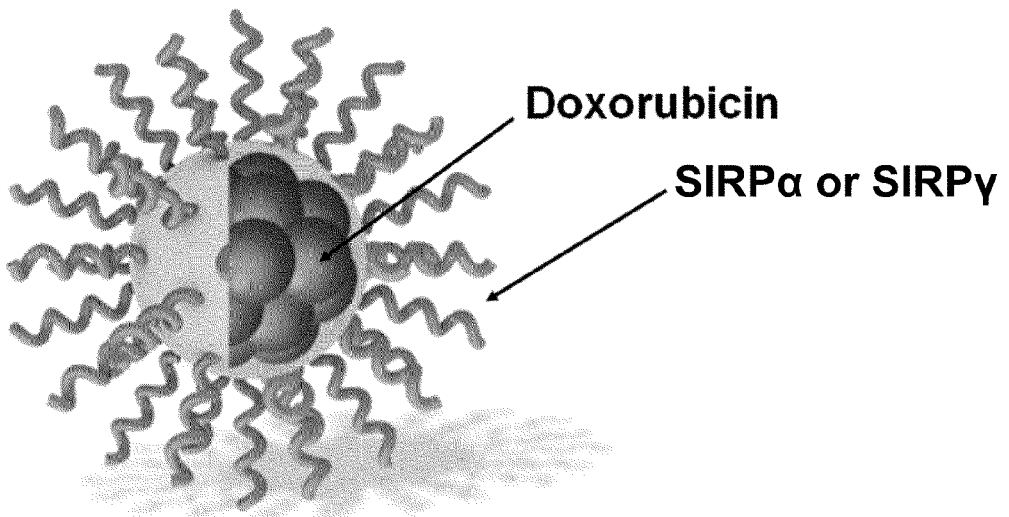
FIG. 1A is a schematic diagram showing an anti-cancer nanocage complex in which doxorubicin is loaded inside a nanocage produced by self-assembly of a fusion protein composed of ferritin heavy chain protein and SIRPα according to an embodiment of the present invention.

The term "immunogenic cell death" as used herein refers to a kind of cell deaths induced by a cell proliferation inhibitor such as anthracyclines, oxaliplatin and bortezomib, radiotherapy or photodynamic therapy. Unlike general apoptosis, the immunogenic cell death of cancer cells can induce an effective anti-cancer immune response through activation of dendritic cells and thus activation of specific T cell responses. The substance causing immunogenic cell death is referred to as "immunogenic cell death inducer". The immunogenic cell death and the immunogenic cell death inducers are well described in Kroemer et al. (*Annu. Rev. Immunol.*, 31: 51-72, 2013). This document is incorporated herein by reference in its entirety.

As used herein, the term "self-assembling protein" refers to a protein capable of forming nanoparticles by forming multimers by regular arrangement at the same time as expression without the aid of a particular inducer. Self-assembling proteins include sHsp (small heat shock protein), ferritin, vault, P6HRC1-SAPN, M2e-SAPN, MPER-SAPN and various virus or bacteriophage capsid proteins. Such self-assembling proteins are well described in Hosseinkhani et al. (*Chem. Rev.*, 113(7): 4837-4861, 2013). This document is incorporated herein by reference in its entirety.

As used herein, the term "phagocytosis enhancing protein" refers to a protein that plays a role in promoting the phagocytosis of cancer cells by macrophages, such as SIRPα, SIRPγ, anti-CD47 antibodies, surfactant protein A and surfactant protein D, which play a role in promoting phagocytosis of cancer cells by phagocytic cells by masking CD47, a phagocytosis evading protein, overexpressed in the surface of cancer cells.

As used herein, the term "SIRP (signal-regulated protein)" is a regulatory membrane glycoprotein that is mainly expressed in bone marrow cells and expressed in stem cells or neurons. Among the SIRPs, SIRPα and SIRPγ act as inhibitory receptors and interact with the broadly expressed transmembrane protein, CD47 protein, which is often referred to as the "do not eat me" signal. These interactions negatively regulate the effector function of innate immune cells, such as host cell phagocytosis. This is similar to the self-signal provided by MHC I family molecules via Ig-like or Ly49 receptors. Cancer cells overexpressing CD47 activate SIRPα and SIRPγ to inhibit macrophage-mediated destruction. Recent studies have shown that high-affinity mutants of SIRPα increase the phagocytosis of cancer cells by masking CD47 on cancer cells (Weiskopf et al., *Science* 341(6141): 88-91, 2013).

As used herein, the term "ferritin heavy chain protein" (hereinafter abbreviated as "FH") refers to a protein that constitutes the heavy chain subunit of ferritin, a major intracellular iron storage protein in prokaryotes and eukaryotes and the ferritin protein consists of 24 subunits of ferritin heavy chains and light chains, respectively. The main function of ferritin proteins is to store iron in a water-soluble, non-toxic state. In addition, it is known that ferritin heavy chain proteins self-assemble into 24 subunits without light chain proteins (Cho et al., *Biochem. Biophys. Res. Commun.* 327(2): 604-608, 2005). The ferritin heavy chain protein can act as a nanocage by loading other drugs into the empty internal space of self-assembled nanoparticles, and due to these properties, has been studied for the purpose of drug delivery.

As used herein, the term "nanocage" refers to a hollow nanoparticle, which includes inorganic nanocage and organic nanocage, where the inorganic nanocages are porous hollow gold nanoparticles prepared by reacting silver nanoparticles with chloroauric acid ($HAuCl_4$) in boiling water and organic nanocages include a protein nanocage prepared by self-assembly of self-assembling proteins such as ferritin.

As used herein, the term "nanocage complex" refers to a nanocage in which a specific substance is loaded into the empty space of the nanocage. For example, when doxorubicin, an anticancer drug, is loaded inside a protein nanocage composed of a ferritin heavy chain protein, it becomes a doxorubicin-encapsulated protein nanocage complex. The "doxorubicin-encapsulated nanocage complex" can be used interchangeably with "doxorubicin-loaded nanocage", "doxorubicin composite protein nanocage" or "doxorubicin-loaded protein nanocage".

The term "hybrid nanocage" as used herein means a protein nanocage produced by self-assembly of two or more fusion proteins comprising two or more different surface expression proteins in the same self-assembling protein.

As used herein, the term "anthracycline-based anticancer agent" or briefly "anthracyclines" refers to a chemotherapeutic anticancer agent belong to cell cycle non-specific anticancer agents derived from *Streptomyces peucetius* var. *caseius*, a bacteria belong to genus *Streptomyces* sp. Anthracycline-based anticancer agents are used for the treatment of various cancers including leukemia, lymphoma, breast cancer, stomach cancer, uterine cancer, ovarian cancer, bladder cancer and lung cancer. The first anthracycline-based anticancer agents discovered were daunorubicin, followed by doxorubicin, followed by epirubicin, idarubicin, pixantrone, sabarubicin, valrubicin, and the like. Examples of the mechanism of action of the anthracyclines include insertion between base paring of the DNA/RNA strands, inhibiting DNA and RNA synthesis, inhibiting the replication of rapidly growing cancer cells, inhibiting transcription and replication by inhibiting relieving stress of supercoiled DNA due to the inhibition of topoisomerase 11 enzyme activity, inducing damage of DNA, protein and cell membrane by formation of iron-mediated free oxygen radicals, and inducing histone expelling from chromatin deregulating epigenome and transcriptomes. Recent studies have shown that doxorubicin increases the Th1 immune response by activating $CD4^+$ cells (Park et al., *Int. Immunopharmacol.* 9(13-14): 1530-1539, 2009), and it was reported that combined administration of doxorubicin and dendritic cells (DCs) induced immunogenic cell death of osteosarcoma (Kawano et al., *Oncol. Let.* 11: 2169-2175, 2016).

The term "taxanoid anticancer agent" or "taxane anticancer drug" as used herein refers to diterpenoid taxane derivatives extracted from genus *Taxus* sp. It is a mitotic inhibitor with a mechanism of promoting assembly and inhibiting disassembly of microtubules in the cell. Currently, commercially available drugs include paclitaxel and docetaxel. Among them, paclitaxel, a taxanoid anticancer drug extracted from the peridum of *Taxus brevifolia* was approved by the US FDA for the treatment of intractable ovarian cancer in 1992 and docetaxel, a taxanoid anticancer agent, derived from *Taxus bacaata*, has similar efficacy to paclitaxel. It is used for the treatment of breast cancer, non-small cell lung cancer, lymphoma, bladder cancer and the like, and has high hydrophilic properties compared with paclitaxel. Recently, a taxane anticancer agent has been shown to have a mechanism of promoting immunogenic cell death of these cancer cells by sensitizing cancer cells to cytotoxic T lymphocytes.

As used herein, the term "immune checkpoint inhibitor" refers to a kind of drugs that block a particular protein produced from certain types of immune system cells, such as T lymphocytes, and some cancer cells. The protein inhibits immune responses and prevents T lymphocytes from killing cancer cells. Thus, when these proteins are blocked, the "braking device" of the immune system is unlocked and T lymphocytes can kill cancer cells better. PD-1/PD-L1 and CTLA-4/B7-1/B7-2 are well known as the above-mentioned "immune check point". PD-1 inhibitors include Pembrolizumab (trade name: Keytruda®), Nivolumab (trade name: Opdivo®), Inhibitors of PD-1 ligand (PD-L1) include Atezolizumab (trade name: Tecentriq®) and Avelumab (trade name: Bavencio®), etc. Meanwhile, Ipilimumab (trade name: Yervoy®) and the like have been approved by the FDA as CTLA-4 inhibitors that inhibit the interaction of CTLA-4/B7-1/B7-2. Recent years have seen impressive success, especially in patients with metastatic melanoma or Hodgkin lymphoma, and show many possibilities in clinical trials in other types of cancer patients.

DETAILED DESCRIPTION

According to one aspect of the present invention, there is provided a pharmaceutical composition for treating cancer comprising a nanocage formed by self-assembly of a fusion protein comprising a phagocytosis enhancing protein and a self-assembling protein, or a nanocage complex in which an immunogenic cell death inducer is encapsulated in the nanocage as an active ingredient.

According to one aspect of the present invention, there is provided a pharmaceutical composition for treating cancer comprising a hybrid nanocage formed by self-assembly of a first fusion protein comprising a phagocytosis enhancing protein and a self-assembling protein, and a second fusion protein comprising a single chain-based antibody analogue targeting an immune checkpoint, and the self-assembling protein or a hybrid nanocage complex in which an immunogenic cell death inducer is encapsulated in the hybrid nanocage as an active ingredient.

In the pharmaceutical composition, the phagocytosis enhancing protein may be SIRPα, SIRPγ, surfactant protein A, surfactant protein D or anti-CD47 antibody. In the pharmaceutical composition, the self-assembling protein may be sHsp (small heat shock protein), ferritin, vault, P6HRC1-SAPN, M2e-SAPN, MPER-SAPN, or a viral or bacteriophage capsid protein. In the pharmaceutical composition, the ferritin may be a ferritin heavy chain protein or a ferritin light chain protein. In the pharmaceutical composition, the viral or bacteriophage capsid protein is selected from the group consisting of a bacteriophage MS2 capsid protein, a bacteriophage P22 capsid protein, a Qβ bacteriophage capsid protein, CCMV capsid protein, CPMV capsid protein, RCNMV capsid protein, ASLV capsid protein, HCRSV capsid protein, HJCPV capsid protein, BMV capsid protein, SHIV capsid protein, MPV capsid protein, SV40 capsid protein, HIV capsid protein, HBV capsid protein, Virus capsid protein, and rotavirus VP6 protein.

In the pharmaceutical composition, the fusion protein may further comprise a linker peptide between the phagocytosis enhancing protein and the self-assembling protein. The linker peptide may be selected from the group consisting of SEQ ID $NO_s$: 65 to 81.

In the pharmaceutical composition, the immunogenic cell death inducer may be an anthracycline-based anticancer agent, a taxane anticancer agent, an anti-EGFR antibody, a BK channel agonist, a bortezomib, a cardiac glycoside, a cyclophosphamides, a GADD34/PP1 inhibitor, a LV-tS-MAC, a Measles virus or an oxaliplatin. The cardiac glycoside may be used in combination with a non-immunogenic cell death inducer. The GADD34/PP1 inhibitor may be used in combination with mitomycin. The anthracycline anticancer agent may be used in combination with mitomycin. The anthracycline-based anticancer agent can be selected from the group consisting of daunorubicin, doxorubicin, epirubicin, idarubicin, pixantrone, sabarubicin, and valrubicin. The taxane anticancer agent may be paclitaxel or docetaxel.

In the pharmaceutical composition, the immune checkpoint may be PD-1, PD-L1, CTLA-4, B7-1 or B7-2 and the immune checkpoint inhibitor may be a PD-1/PD-L1 interaction inhibitor or a CTLA-4/B7-1/B7-2 interaction inhibitor.

In the pharmaceutical composition, the PD-1/PD-L1 interaction inhibitor may be Pembrolizumab, Nivolumab, Atezolizumab or Avelumab. The CTLA-4/B7-1/B7-2 interaction inhibitor may be Ipilimumab.

In the pharmaceutical composition, the single chain-based antibody analogue may be a scFv, a sdAb, a diabody, a monobody, a variable lymphocyte receptor (VLR), a nanobody, or a camelid immunoglobulin heavy chain fragment (VtiH).

According to another aspect of the present invention, there is provided a fusion protein in which a signal-regulatory protein alpha (SIRPα) or a SIRPγ is linked to the N-terminal or C-terminal of a ferritin heavy chain protein.

In the fusion protein, the ferritin heavy chain protein may comprise an amino acid sequence of any one of SEQ ID NO$_s$: 1 to 11, and preferably a human ferritin heavy chain protein consisting of the amino acid sequence of SEQ ID NO: 1.

In the fusion protein, the SIRPα may be a full-length protein of SIRPα, and may be a fragment containing an IgV (immunoglobulin variable domain) of SIRPα, and the fragment may comprise an amino acid sequence of any one of SEQ ID NOs: 12 to 64.

In the fusion protein, the SIRPγ may be a full-length protein of SIRPγ and may be a fragment containing an IgV (immunoglobulin variable domain) of SIRPγ, and the fragment may be composed of the amino acid sequence of SEQ ID NO: 98 or 100.

The fusion protein may further comprise a linker peptide between the ferritin heavy chain protein and the SIRPα protein or SIRPγ protein. The linker peptide may be selected from the group consisting of (G$_4$S)$_n$ (SEQ ID NO: 102), (GSSGGS)$_n$ (SEQ ID NO: 103), KESGSVSSE-QLAQFRSLD (SEQ ID NO: 65), EGKSSGSGSESKST (SEQ ID NO: 66), GSAGSAAGSGEF (SEQ ID NO: 67), (EAAAK)$_4$ (SEQ ID NO: 104), CRRRRRREAEAC (SEQ ID NO: 68), A(EAAAK)$_4$ALEA(EAAAK)$_4$A (SEQ ID NO: 69), GGGGGGGG (SEQ ID NO: 70), GGGGGG (SEQ ID NO: 71), GGGGS (SEQ ID NO: 72), AEAAAKEAAAAKA (SEQ ID NO: 73), PAPAP (SEQ ID NO: 74), (Ala-Pro)$_n$, VSQTSKLTRAETVFPDV (SEQ ID NO: 75), PLGLWA (SEQ ID NO: 76), TRHRQPRGWE (SEQ ID NO: 77), AGNRVRRSVG (SEQ ID NO: 78), RRRRRRRR (SEQ ID NO: 79), GFLG (SEQ ID NO: 80), and GSSGGSGSSGGSGGGDEADGSRGSQKAGVDE (SEQ ID NO: 81).

In addition, a tag peptide for purification may be further added at the N-terminal or C-terminal of the fusion protein for efficient purification of the fusion protein. The tag peptide may comprise a His×6 peptide (SEQ ID NO: 82), a GST peptide, a FLAG peptide (DYKDDDK, SEQ ID NO: 83), a streptavidin binding peptide, a VS epitope peptide (GKPIPNPLLGLDST, SEQ ID NO: 84), a Myc peptide (EQKLISEE, SEQ ID NO: 85), or HA peptide (YPYDVPDYA, SEQ ID NO: 86).

According to another aspect of the present invention, there is provided a polynucleotide encoding the fusion protein.

According to another aspect of the present invention, there is provided a vector comprising the polynucleotide.

The recombinant vector of the present invention may be a prokaryotic vector, a eukaryotic vector or a viral vector. The prokaryotic vector may be a plasmid vector, a phage vector, a phagemid vector, a cosmid vector or a bacterial artificial chromosome vector. The eukaryotic vector may be a yeast vector, an insect cell vector, a mammalian vector, or a plant cell vector. The viral vector may be an adenovirus vector, a lentivirus vector, or a retrovirus vector.

According to another aspect of the present invention, there is provided a transformed host cell prepared by transforming a host cell with the vector.

In the transformed host cell, the host cell may be a prokaryotic cell or a eukaryotic cell. The prokaryotic cell may be a gram-negative bacterium or a gram-positive bacterium. The eukaryotic cell may be a fungal cell, a plant cell, or an animal cell. The fungal cell may be an ascomycete or a basidiomycete. The animal cell may be an insect cell or a mammalian cell.

According to another aspect of the present invention, there is provided a protein nanocage formed by self-assembly of the fusion protein.

According to another aspect of the present invention, there is provided an anticancer protein nanocage complex in which an immunogenic cell death inducer is encapsulated in the protein nanocage.

In the anticancer protein nanocage complex, the immunogenic cell death inducer may be an anthracycline-based anticancer agent, a taxananoid anticancer agent, an anti-EGFR antibody, a BK channel agonist, a bortezomib, a cardiac glycoside, a cyclophosphamide, a GADD34/PP1 inhibitor, LV-tSMAC, Measles virus, or oxaliplatin. In the anticancer protein nanocage complex, the cardiac glycoside may be used in combination with a non-immunogenic cell death inducer. The GADD34/PP1 inhibitor may be used in combination with mitomycin. The anthracycline-based anticancer agent may be at least one selected from the group consisting of daunorubicin, doxorubicin, epirubicin, idarubicin, pixantrone, sabarubicin, and valrubicin. The taxanoid anticancer agent may be paclitaxel or docetaxel.

The anticancer protein nanocage complex may further comprise an immune checkpoint inhibitor. The immune checkpoint inhibitor may be a PD-1/PD-L1 interaction inhibitor or a CTLA-4/B7-1/B7-2 interaction inhibitor.

In the anticancer protein nanocage complex, the PD-1/PD-L1 interaction inhibitor may be Pembrolizumab, Nivolumab, Atezolizumab or Avelumab. The CTLA-4/B7-1/B7-2 interaction inhibitor may be Ipilimumab.

According to another aspect of the present invention, there is provided a pharmaceutical composition for the treatment of cancer comprising the protein nanocage or the anticancer protein nanocage complex as an active ingredient.

The pharmaceutical composition of the present invention may comprise a pharmaceutically acceptable carrier. The composition comprising a pharmaceutically acceptable carrier may be various oral or parenteral formulations, but is preferably a parenteral formulation. In the case of formulation, a diluent or excipient such as a commonly used filler, an extender, a binder, a wetting agent, a disintegrant, a surfactant or the like is used. Solid preparations for oral administration include tablets, pills, powders, granules, capsules and the like, which may contain at least one excipient such as starch, calcium carbonate, sucrose, lactose, or gelatin, etc. In addition to simple excipients, lubricants such as magnesium stearate, talc, and the like may also be used. Liquid preparations for oral administration include suspensions, solutions, emulsions, and syrups. Various excipients such as wetting agents, sweetening agents, fragrances, preservatives, etc. may be included in addition to water and liquid paraffin, which are simple diluents used commonly. Preparations for parenteral administration include sterile aqueous solutions, non-aqueous solutions, suspensions, emulsions, lyophilized formulations, and suppositories. Examples of the non-aqueous solvent and the suspensions include propylene glycol, polyethylene glycol, vegetable oil such as olive oil, and injectable ester such as ethyl oleate. As a base for suppositories, witepsol, macrogol, Tween 61, cacao butter, laurin butter, and glycerogelatin can be used.

The pharmaceutical composition may be in a form selected from the group consisting of tablets, pills, powders, granules, capsules, suspensions, solutions, emulsions, syrups, sterilized aqueous solutions, non-aqueous solutions, lyophilized formulations, and suppositories.

The pharmaceutical composition of the present disclosure may be administered orally or parenterally. When administered parenterally, the pharmaceutical composition may be administered via various routes, including intravenous injection, intranasal inhalation, intramuscular administration, intraperitoneal administration, transdermal absorption, etc.

The pharmaceutical composition of the present invention may be administered in a therapeutically effective amount. As used herein, the term "therapeutically effective amount" refers to an amount sufficient for the treatment of diseases at a reasonable benefit/risk ratio applicable to a medical treatment, and the level of the therapeutically effective amount or dose may be determined based on the factors including the kind of a subject, severity of illness, age, sex, drug activity, drug sensitivity, administration time, administration route and excretion rate, duration of treatment, factors including drug(s) to be used simultaneously in combination, and other factors well-known in the medical field. The pharmaceutical composition of the present invention may be administered in an amount of 0.1 mg/kg to 1 g/kg, and more preferably, 1 mg/kg to 500 mg/kg. Meanwhile, the administration dose may be appropriately adjusted according to the age, sex, and health conditions of a patient.

The pharmaceutical composition of the present invention can be administered as an individual therapeutic agent or in combination with other anti-cancer agents. In this case, the pharmaceutical composition of the present invention may be administered sequentially or simultaneously with other conventional anti-cancer agents. In addition, the pharmaceutical composition may be administered singly or multiply. It is important to take into account all of the above factors and to administer the amount in which the maximum effect can be obtained in a minimal amount without side effects, and these factors can be easily determined by those skilled in the art.

According to one aspect of the present invention, there is provided a method for treating cancer in a subject comprising administering therapeutically effective amount of the protein nanocage or the nanocage complex encapsulating an immunogenic cell death inducer to the subject.

The loading of the immunogenic cell death inducer into the nanocage can be accomplished by culturing genetically engineered cells to produce recombinant nanocages in the cell culture medium in which the immunogenic cell death inducer is dissolved and isolating the nanocage, or by mixing isolated nanocages with the immunogenic cell death inducer in a solvent. Preferably, a complex of divalent metal ions (for example, $Cu^{2+}$, $Fe^{2+}$, and $Zn^{2+}$) and the immunogenic cell death inducer is formed, and then incubated with prepared ferritin heavy chain nanocage in buffer so that the complex of divalent metal ions and the immunogenic cell death inducer can be loaded in the inner space of the prepared ferritin heavy chain nanocage. In addition, the anticancer agent can be loaded into the inner space through the disassemble-reassembly process of the ferritin heavy chain nanocage due to pH differences, and/or the anticancer agent can be loaded on the protein nanocage by pore opening due to differences in ion concentration.

The recent identification of mutated proteins in tumors, known as neoantigens, which are targets in cancer immunotherapy has led to the development of therapies that augment antitumor T cell responses. Despite the highly mutagenic nature of cancer cells, only 1% of mutated proteins expressed in tumors are immunogenic in cancer patients. For a neoantigen to be immunogenic, it must be processed then presented by the major histocompatibility complex (MHC) molecules on cell surfaces. Also, efficient delivery of immunogenic neoantigens from tumor to a host's T cell is only achieved by activated and neoantigen peptide-loaded antigen presenting cells (APCs). In an attempt to trigger host immunity against cancers, we exploited the characteristic of genetic instability, taking advantage of the fact that immunogenic tumor neoantigens triggers immunity against cancer cells. We have overcome the activation-energy threshold of immunosuppressive tumor microenvironment and developed a new strategy to mediate the delivery and presentation of tumor neoantigens by APCs to a host's T cells. The approach is based on ferritin-based nanocages that carry not only ligands that enhance cancer cell phagocytosis by APCs, but also drugs that induce immunogenic cancer cell death (ICD) as well as deliver ligands that enhance cancer cell phagocytosis by APCs. Accordingly, the present inventors developed a next generation anticancer therapeutics comprising an anticancer nanocage complex in which doxorubicin is loaded inside a nanocage produced by self-assembly of a fusion protein composed of a ferritin heavy chain protein and SIRPα, or one further comprising an immune checkpoint inhibitor (a specific type of drugs blocking particular protein produced by particular immune system cells such as T lymphocyte and some cancer cells). The anticancer nanocage complex promotes anti-cancer immune responses specific to cancer antigens by inducing immunogenic cell death of cancer cells and thus does not have side effects caused by previous anticancer chemotherapeutics and sustains anti-cancer effect by immune cells even after treatment.

The present invention will now be described in detail with reference to the accompanying drawings. In the drawings, the components may be exaggerated or reduced in size for convenience of explanation.

Figure 1B:
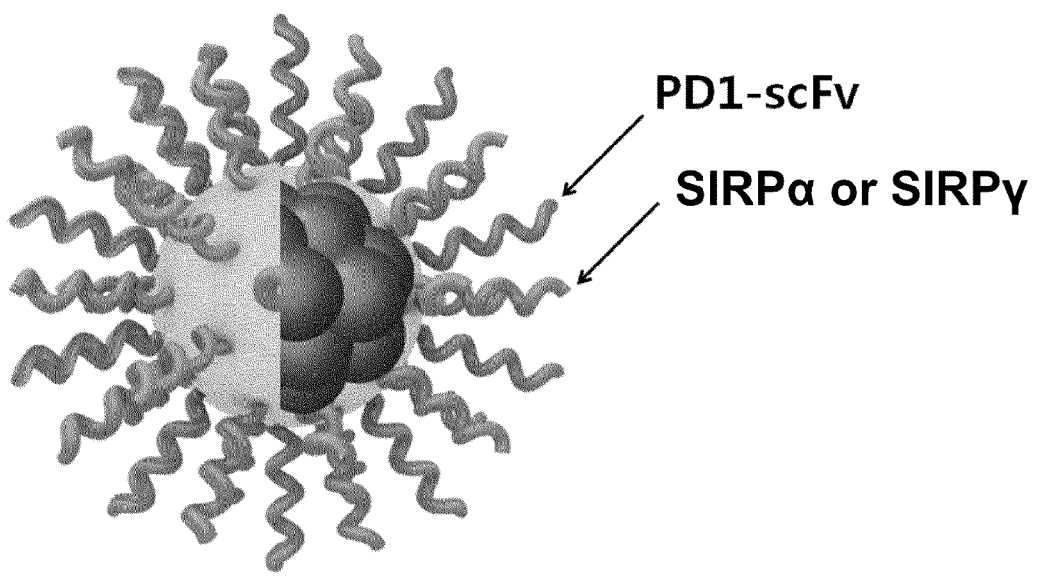
FIG. 1B is a schematic diagram of an anticancer hybrid nanocage complex including the fusion protein and a second fusion protein comprising a ferritin heavy chain protein and a single chain-based antibody targeting PD-1/PD-L1 as an immune checkpoint inhibitor.

FIG. 1A is a schematic diagram showing an anti-cancer nanocage complex in which doxorubicin is loaded inside a nanocage produced by self-assembly of a fusion protein composed of ferritin heavy chain protein and SIRPα according to an embodiment of the present invention. As shown in FIG. 1A, when a fusion protein in which a SIRPα or SIRPγ protein is linked to the C-terminal of a ferritin heavy chain protein is expressed, a hollow ferritin nanocage is formed by self-assembly of ferritin heavy chain protein 24 subunits. FIG. 1B is a schematic diagram showing an anticancer nanocage complex in which doxorubicin is encapsulated within a hybrid nanocage consisting of a first fusion protein comprising a ferritin heavy chain protein and SIRPα or SIRPγ and a second fusion protein comprising a ferritin heavy chain protein and a single chain variable fragment targeting PD-1 (PD1-scFV, SEQ ID NO: 1), one of immune checkpoints. The hybrid nanocage shown in FIG. 1B may exhibit a synergistic effect by promoting immunological activity by masking CD47 through SIRPα or SIRPγ and promoting immunological activity based on inhibition of immune checkpoints.

Figure 3A:
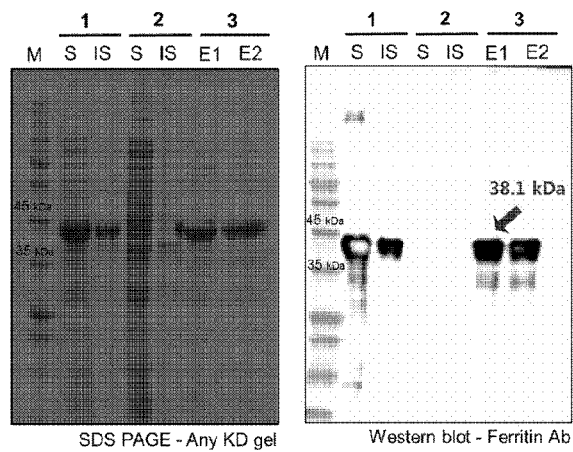
FIGS. 3A and 3B are photographs showing the results of SDS-PAGE and Western blot analysis showing the expression and purification of a ferritin heavy chain protein-SIRPα fusion protein according to an embodiment of the present invention.
Figure 3B:
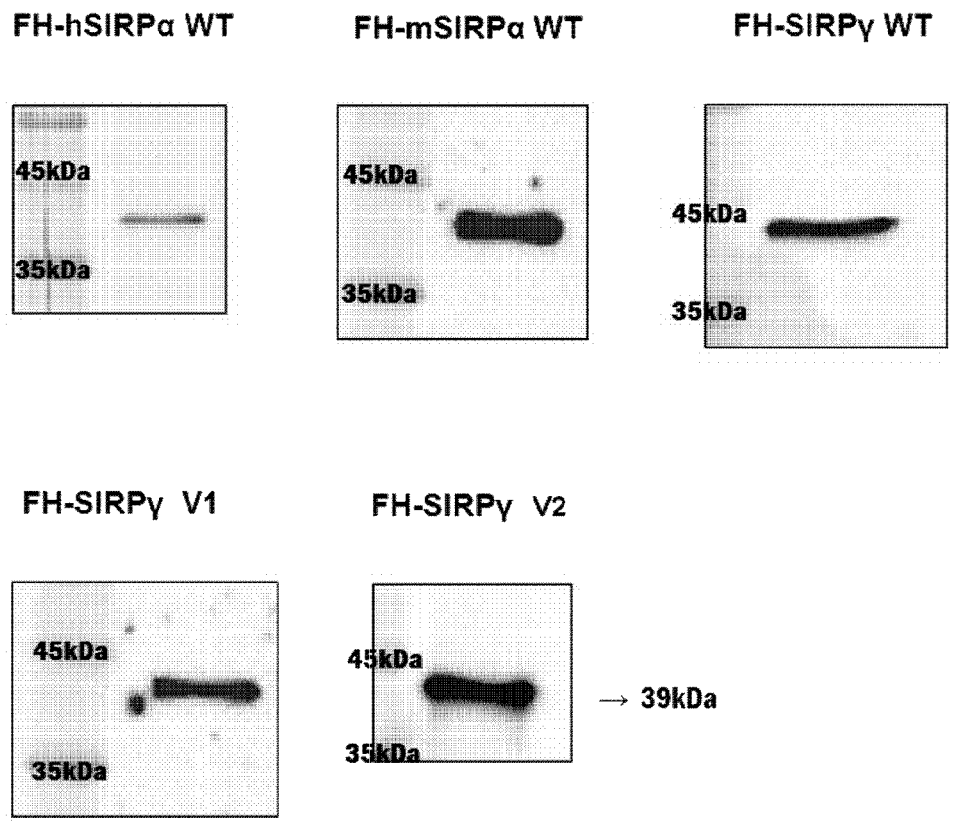
Figure 3C:
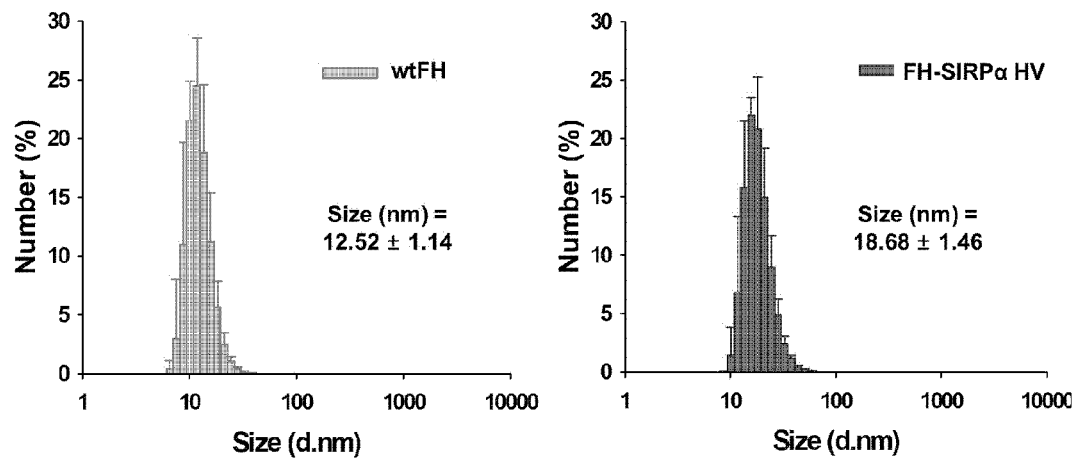
FIGS. 3C and 3D are graphs showing the result of particle size distribution analysis of the nanocages produced by self-assembly of the fusion protein and nanocages produced by self-assembly of ferritin heavy chain only.
Figure 3D:
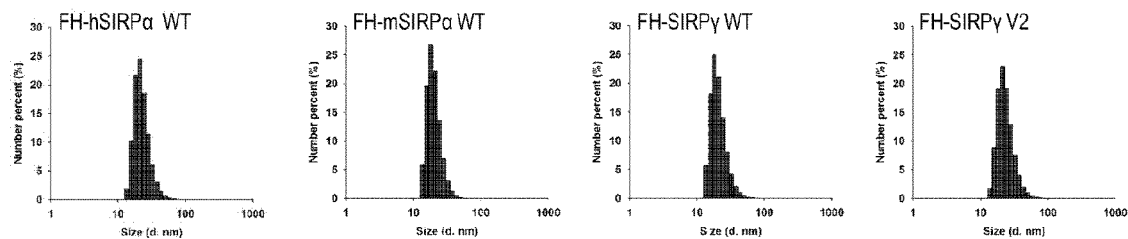
Figure 3E:
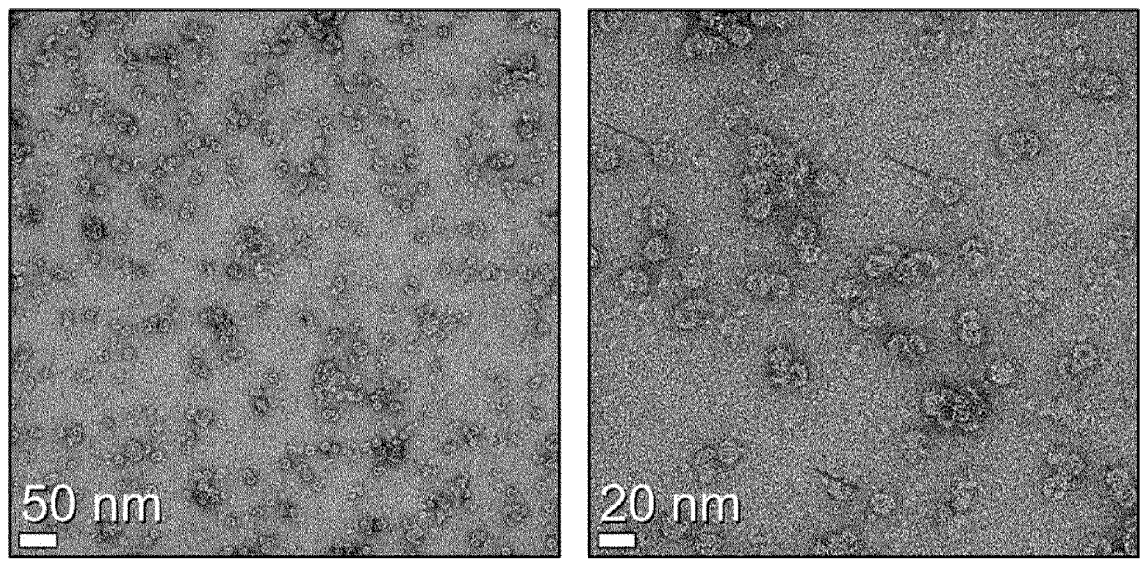
FIG. 3E is an electron micrograph of a nanocage produced by self-assembly of the fusion protein.

The present inventors have experimentally proved that a ferritin heavy chain protein whose C-terminal is linked to SIRPα protein formed a protein nanocage successfully (see FIGS. 3A, and 3C to 3E). In addition, the present inventors have experimentally proved that a ferritin heavy chain protein whose C-terminal is linked to SIRPγ wild-type and SIRPγ variant as well as SIRPα wild-type also form nanocages (FIGS. 3B and 3D). Moreover, it has been experimentally proved that even when doxorubicin, an anthracycline-based anticancer agent, is encapsulated in the nanocage, it has a morphology of a nanoparticle (see FIGS. 4A to 4D).

The nanocage produced by the self-assembly of the FH-SIRPα fusion protein not only binds to CD47 of cancer cells (see FIGS. 5A and 5B), but also promotes phagocytosis of cancer cells by macrophages (see FIGS. 6A to 6H). In addition, the present inventors experimentally demonstrated that the growth of cancer is inhibited significantly in tumor-model animals prepared by transplanting cancer cells subcutaneously by administrating the anti-cancer nanocage complex loaded with doxorubicin (See FIGS. 7A to 7G).

The nanocage-based anticancer drug of the present invention delivers drugs that induce immunogenic cancer cell death (ICD) as well as ligands that enhance cancer cell phagocytosis by APCs (antigen presenting cells). The nanocage therapeutic agent of the present invention arouses the host's immune system against cancer cells and allows the host to obtain an intrinsic anti-cancer vaccination against the cancer, by inducing the secretion of danger signals and neoantigens in dying cancer cells, enhancing phagocytosis cancer cells, and cross-priming tumor-specific T cells by dendritic cells loaded with neoantigen peptides (see FIGS. 9A-9C).

Innate immune cells such as macrophages and dendritic cells mediate the activation of the adaptive immune system through phagocytosis and antigen presentation and play an important role in initial host defense against pathogens. One mechanism to avoid phagocytosis by innate immune cells is to up-regulate CD47, a signal "do not eat me". Blocking the CD47-SIRPα axis between tumor cells and phagocytic cells, increases phagocytosis of tumor cells and thus was proven to be an advantage as a target of anti-cancer immunotherapy. In addition, CD47-based therapies have been shown to be effective in the development of innate and adaptive immune responses in immunocompetent mouse models (Liu, X. J. et al., *Nat Med.* 21, 1209-1215, 2015). Recently, SIRPα mutants and nanobodies that block CD47 as an anti-cancer therapeutics have been developed.

Figure 2:
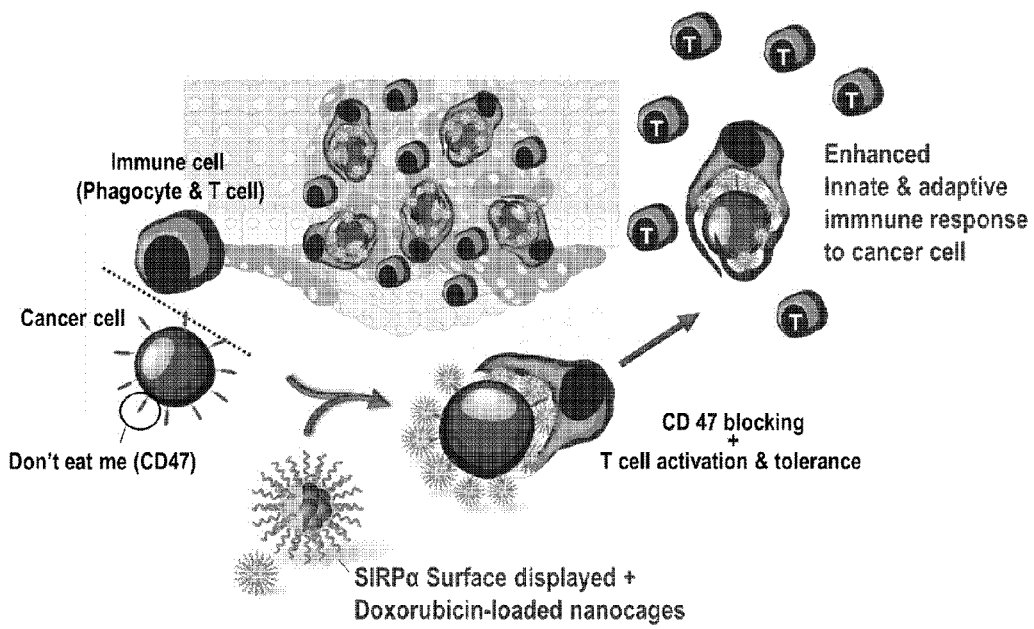
FIG. 2 is a schematic diagram showing a mechanism of action of an anti-cancer nanocage complex according to an embodiment of the present invention.

To improve CD47-mediated immunotherapy, we designed a nanocage by engineering the surface of human ferritin to include SIRPα variants capable of binding and antagonizing human and murine CD47 and named it FH-SIRPα HV. The nanocage could also bind to human and mouse CD47 and block its function (FIG. 2), like SIRPα.

The present inventors have conducted intensive studies on the secretion of immunogenic neoantigens and danger signals in dying cancer cells and found that the FH-SIRPα HV nanocage stimulates local inflammatory reaction and induces the production of dendritic cells presenting a neoantigen. Some dying cancer cells trigger a massive immune response, which is called "immunogenic cell death" (Kroemer et al., *Annu. Rev. Immunol.* 31: 51-72, 2013). The ICD communicates with a combination of three distinct "danger" signals, restricted spatio-temporally:

(1) an "eat-me" signal associated with translocation of calreticulin (CRT) existing the endoplasmic reticulum (ER) to the cell surface; (2) a "find-me" signal associated with the activation of ATP secretion; and (3) a signal that promotes antigen-processing and presentation to T cells related to the extracellular secretion of the nuclear high-mobility group box 1 (HMGB1) protein. These signals regulate a series of receptors expressed on the dendritic cell surface to stimulate the presentation of tumor neoantigens to T cells. The present inventors therefore hypothesized that the ICD inducer co-delivered with the CD47 antagonist to the tumor microenvironment would trigger danger signals and initiate a cellular immune response from dying cancer cells.

Doxorubicin (dox), an anthracycline-based anticancer drug that induces three characteristics of ICD in cancer cells treated was selected as an ICD inducer to be delivered with FH-SIRPα and the advantages of metal ion-binding affinity of ferritin was used. The metal-ion binding affinity of the ferritin allows a metal-based drug or metal-complex drug to accumulate in the central cavity of the ferritin. The present inventors prepared a doxorubicin formulation in which doxorubicin is encapsulated in FH-SIRPα nanocage by incorporating doxorubicin pre-complexed with Cu (II) into the interior of the nanocage, and named it FH-SIRPα HV-Dox. Successful loading of doxorubicin into FH-SIRPα nanocage was confirmed by size-exclusion chromatography and the amount of encapsulated doxorubicin was confirmed to be 54 doxorubicin molecules per FH-SIRPα nanocage (FIGS. 4A-4D).

The above-mentioned FH-SIRPα HV-Dox was administered to tumor model mice, and it was confirmed that there was a strong synergistic antitumor activity reflecting a favorable accumulation of a large amount of CD47 antagonist and ICD in tumor tissues. The stimulation of local inflammatory responses, the phagocytosis and maturation of innate immune cells in an immunosuppressive tumor microenvironment induce effective delivery and presentation of immunogenic tumor neoantigens to T cells. These strong immune responses have resulted in complete remission of cancer and a persistent anti-tumor immune response and, overall, has proven to be a universal and effective approach to activating the immune system of the host against cancer.

In comparison, current cancer vaccines are limited in that they require constant expression of the desired target tumor neoantigen and induce the formation of resistant clones that do not express the target tumor neoantigen. Chimeric antigen receptor (CAR) T cell therapy is also associated with other major obstacles, including the need for constant expression of the desired target tumor neoantigen, optimization requirements, and the economic cost required for ex vivo manipulation. In addition, regulatory antibodies such as anti-PD-1 antibody have the disadvantage that all activated or depleted T cells, including anti-tumor and anti-autoimmune T cells, can be stimulated. However, the FH-SIRPα HV-Dox of the present invention is a powerful immunostimulant that has proven its efficacy as an "intrinsic anti-cancer vaccination" that activates both local and systemic anti-tumor specific immune responses. Furthermore, considering that the durability of FH-SIRPα HV-Dox of the present invention is strong and robust, the synergistic effect has a wide potential and can be used for various types of cancer treatment regardless of the stage.

EXAMPLES

Hereinafter, specific embodiments of the present disclosure will be described in detail. However, the present disclosure is not limited to embodiments explained herein but may be specified in various aspects. Rather, the embodiments are provided to sufficiently transfer the concept of the present disclosure to a person skilled in the art to thorough and complete contents introduced herein.

Figure 1C:
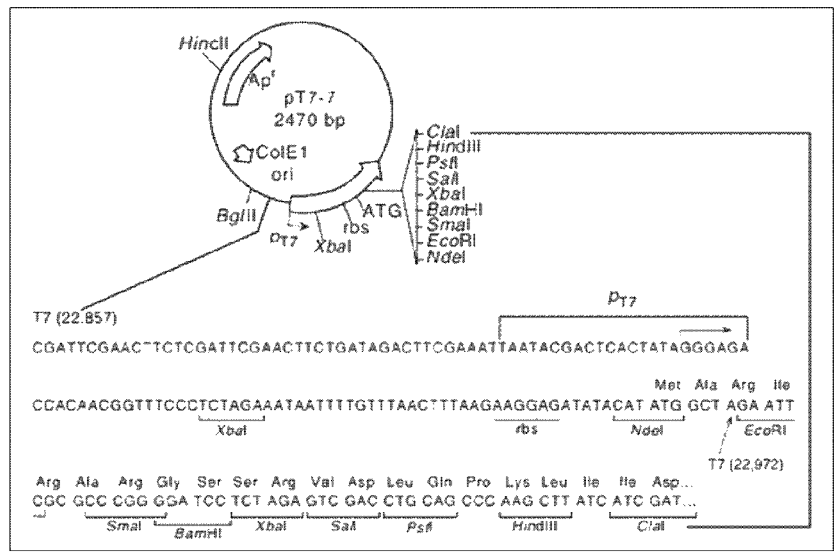
FIG. 1C is a schematic diagram of the plasmid vector used for the expression of FH-SIRPα.

Example 1: Preparation of Ferritin Nanocages 1-1: Fusion Protein Comprising a Ferritin Heavy Chain Protein and a SIRPα High-Affinity Variant The present inventors prepared a polynucleotide (SEQ ID NO: 87) encoding a human ferritin heavy chain protein (hFTH) consisting of the amino acid sequence shown in SEQ ID NO: 1; a polynucleotide (SEQ ID NO: 88) encoding a linker peptide consisting of the amino acid sequence shown in SEQ ID NO: 65 and a polynucleotide (SEQ ID NO: 89) encoding a SIRPα high-affinity variant consisting of the amino acid sequence shown in SEQ ID NO: 12 by PCR or nucleotide synthesis, linked them using restriction enzymes and ligase and then cloned the linked polynucleotide into pT7-7 vector comprising His tag. To facilitate cloning of the polynucleotides encoding the respective proteins or peptides, a Xho I recognition site was added between the hFTH and the linker peptide, a Hind III recognition site was added between the linker peptide and SIRPα, a Cla 1 recognition site was added to the 3'-end of the polynucleotide encoding SIRPα (FIG. 1C).

The vectors prepared above were transformed into *E. coli* by the method described by Hanahan (Hanahan D, DNA Cloning vol. 1, 109-135, IRS press, 1985). Specifically, the above-prepared vectors were transformed with *E. coli* BL21 (DE3) treated with $CaCl_2$ by heat shock method, and then cultured in a medium containing ampicillin to select cells showing ampicillin resistance. The transformed cells were cultured at 36° C. until the $OD_{600}$ reached 0.6, and the expression of the fusion protein was induced by adding 1 mM IPTG and further cultured at 20° C. for 16 hours. The cultured cells were recovered, disrupted by sonication, and centrifuged at 12,000×g for 30 minutes to remove cellular debris. The recombinant proteins were each separated using a $Ni^{2+}$-NTA column (Qiagen, Hilden, Germany) (wash buffer: pH 8.0, 50 mM sodium phosphate, 300 mM NaCl, 80 mM imidazole; elution buffer: pH 8.0, 50 mM sodium phosphate, 300 mM NaCl, 250 mM imidazole). To remove imidazole from the elution buffer, the buffer was replaced with PBS using a membrane filter (Amicon, 10K). The concentration of the obtained nanocage was measured by Bradford protein analysis method. The nanocage thus prepared was named as 'FH-SIRPα HV'.

1-2: Fusion Protein Comprising a Ferritin Heavy Chain Protein and a SIRPα Wild-Type Protein The present inventors prepared a fusion protein in which a human SIRPα wild-type protein is linked to ferritin heavy chain protein and a ferritin heavy chain nanocage using the fusion protein (hereinafter, referred as to 'FH-hSIRPα WT nanocage') by the same method of Example 1-1 except that the polynucleotide (SEQ ID NO: 93) encoding the human SIRPα wild-type protein consisting of the amino acid sequence shown in SEQ ID NO: 92 was used instead of the SIRP alpha high-affinity variant.

In addition, the present inventors prepared a fusion protein in which a mouse SIRPα wild-type protein is linked to ferritin heavy chain protein and a ferritin heavy chain nanocage using the fusion protein (hereinafter, referred as to 'FH-mSIRPα WT nanocage') by the same method of Example 1-1 except that the polynucleotide (SEQ ID NO: 95) encoding the mouse SIRPα wild-type protein consisting of the amino acid sequence shown in SEQ ID NO: 94 was used instead of the human SIRPα wild-type protein.

1-3: Fusion Protein Comprising a Ferritin Heavy Chain Protein and a SIRPγ Wild-Type Protein The present inventors prepared a fusion protein in which a SIRPγ wild-type protein is linked to ferritin heavy chain protein and a ferritin heavy chain nanocage using the fusion protein (hereinafter, referred as to 'FH-SIRPγ WT nanocage') by the same method of Example 1-1 except that the polynucleotide (SEQ ID NO: 97) encoding the SIRPγ wild-type protein consisting of the amino acid sequence shown in SEQ ID NO: 96 was used.

1-4: Fusion Protein Comprising a Ferritin Heavy Chain Protein and a SIRPγ Variant 1 Protein The present inventors prepared a fusion protein in which a SIRPγ variant protein having amino acid mutations corresponding to the SIRPα high-affinity variant is linked to ferritin heavy chain protein and a ferritin heavy chain nanocage using the fusion protein (hereinafter, referred as to 'FH-SIRPγ V1 nanocage') by the same method of Example 1-1 except that the polynucleotide (SEQ ID NO: 99) encoding the SIRPγ variant consisting of the amino acid sequence shown in SEQ ID NO: 98 was used instead of the SIRPα high-affinity variant protein.

1-5: Fusion Protein Comprising a Ferritin Heavy Chain Protein and a SIRPγ Variant 2 Protein The present inventors prepared a fusion protein in which a SIRPγ variant protein having amino acid substitution corresponding to the SIRPα high-affinity variant except that the $27^{th}$ amino acid is not substituted in the SIRPγ variant protein (hereinafter, referred as to "SIRPγ HV2") is linked to ferritin heavy chain protein and a ferritin heavy chain nanocage using the fusion protein (hereinafter, referred as to 'FH-SIRPγ V2 nanocage') by the same method of Example 1-1 except that a polynucleotide (SEQ ID NO: 101) encoding the SIRPγ HV2 consisting of amino acid sequence shown in SEQ ID NO: 100 was used instead of the SIRPα high-affinity variant.

Experimental Example 1: Confirmation of Production of Ferritin Nanocage

The present inventors confirmed protein expression by SDS-PAGE and western blot analysis using an anti-ferritin heavy chain antibody from the crude extract obtained in the above Examples 1-1 to 1-5. As a result, as shown in FIGS. 3A and 3B, the fusion protein according to one embodiment of the present invention was mainly distributed in the water-soluble fraction, and some were found to be present in the insoluble fraction, and a band corresponding to 38.1 kDa (about 39 kDa) was clearly detected from the affinity purification using the nickel affinity column indicating that the protein purification using the His tag was also successfully performed. Next, the present inventors analyzed the particle size of the recovered nanocage using a dynamic light scattering (DLS) analyzer (Malvern zetasizer nano ZS, UK) and imaged the nanocages produced by a transmission electron microscope.

Figure 3F:
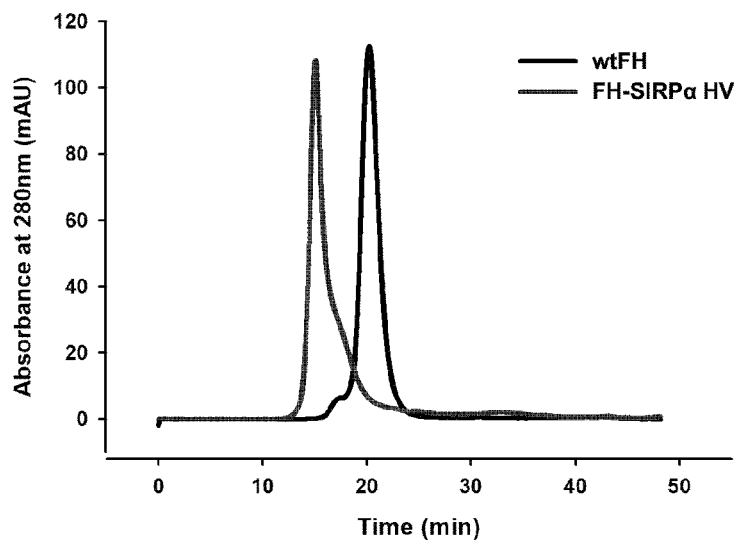
FIG. 3F is a chromatogram comparing the nanocage produced by the self-assembly of the fusion protein and the nanocage produced by self-assembly of the ferritin heavy chain protein only by FPLC analysis.

As a result, as shown in FIGS. 3C and 3D, the FH-SIRPα nanocage prepared according to an embodiment of the present invention showed spherical nanoparticles having a relatively uniform size of about 10 to 20 nm which was similar to the particle size distribution of wild-type ferritin heavy chain protein. As shown in FIG. 3F, when FH-SIRPα nanocage (hereinafter abbreviated as "FH-SIRPα HV nanocage") according to an embodiment of the present invention was analyzed by fast protein liquid chromatography (FPLC) and it was observed as one peak as in the case of the wild-type ferritin heavy chain nanocage, and it was confirmed that it was produced in a uniform state. The FH-SIRPα HV nanocage according to an embodiment of the present invention has a slightly longer retention time than wild-type ferritin heavy chain nanocage, which is a natural result due to an increase in molecular weight due to protein fusion.

Example 2: Preparation of Hybrid Nanocage

A recombinant expression vector in which a polynucleotide (SEQ ID NO: 93) encoding a first fusion protein comprising a FLAG tag consisting of the amino acid sequence shown in SEQ ID NO: 92, a human ferritin heavy chain protein (hFTH) consisting of the amino acid sequence shown in SEQ ID NO: 1; a linker peptide consisting of the amino acid sequence shown in SEQ ID NO: 65 and a SIRPα high-affinity variant consisting of the amino acid sequence shown in SEQ ID NO: 12 is operably linked to a promoter is constructed (hereinafter, referred as to "pCMV-FLAG-hFTH-SIRPα HV").

Further, a recombinant expression vector in which a polynucleotide (SEQ ID NO: 94) encoding a first fusion protein comprising a FLAG tag consisting of the amino acid sequence shown in SEQ ID NO: 92, a human ferritin heavy chain protein (hFTH) consisting of the amino acid sequence shown in SEQ ID NO: 1; a linker peptide consisting of the amino acid sequence shown in SEQ ID NO: 65 and a scFv peptide against PD-1/PD-L1, an immune checkpoint, consisting of amino acid sequence shown in SEQ ID NO: 93 is operably linked to a promoter is constructed (hereinafter, referred as to "pCMV-FLAG-hFTH-PD1-scFV").

CHO cells were co-transfected with the two expression vectors, and hybrid nanocages presenting the SIRPα and the scFv against PD-1/PD-L1 on the surface which are produced by self-assembly of two fusion proteins are recovered by affinity chromatography using an anti-FLAG antibody.

In addition, the hybrid nanocage is treated with a Cu-dox complex to encapsulate doxorubicin therein to produce an anticancer hybrid nanocage complex (FIG. 1B).

Example 3: Preparation of Doxorubicin-Loaded Nanocage

Figure 4A:
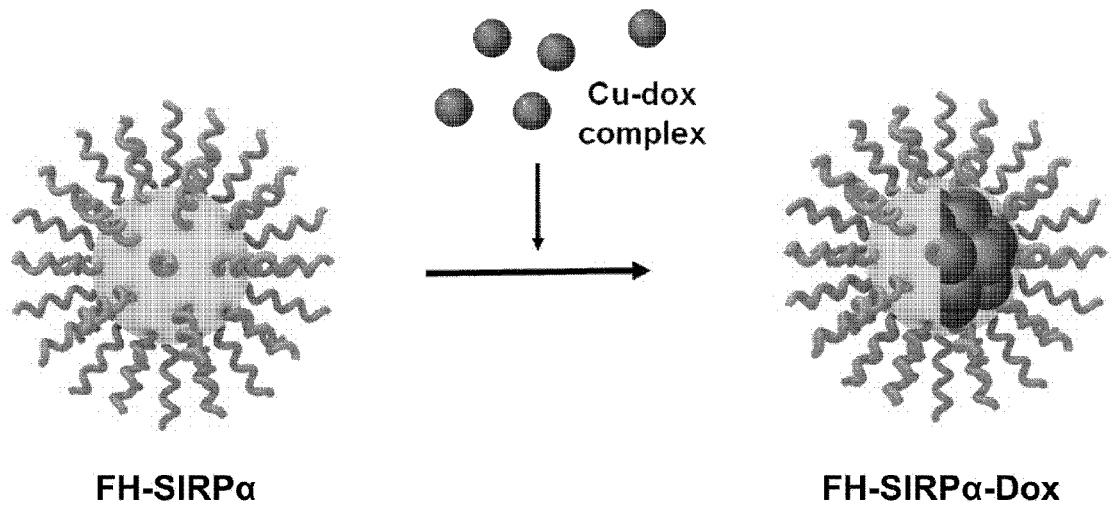
FIG. 4A is a schematic diagram showing a process of encapsulating doxorubicin (dox) in a nanocage (FH-SIRPα) according to an embodiment of the present invention.

The present inventors firstly reacted 1 mg/ml of doxorubicin with 1 mM of copper ion ($Cu^{2+}$) for 30 minutes at room temperature to form a doxorubicin-copper ion complex. Then, the mixture was added to the FH-SIRPα Solution (250 µg/ml) prepared in Example 1 and reacted at room temperature for 120 minutes and then doxorubicin and free copper ions were removed by chromatography using a PD-10 column (FIG. 4A). The loaded doxorubicin was quantified by comparison with a standard curve after measuring with a fluorescence spectrometer (2103 EnVision™ Multilabel Plate Readers, PerkinElmer, USA). To confirm whether the prepared doxorubicin nanocage complex was formed as nanoparticles, FPLC analysis, DLS analysis and transmission electron microscopic imaging were performed in the same manner of the Experimental Example 1.

Figure 4B:
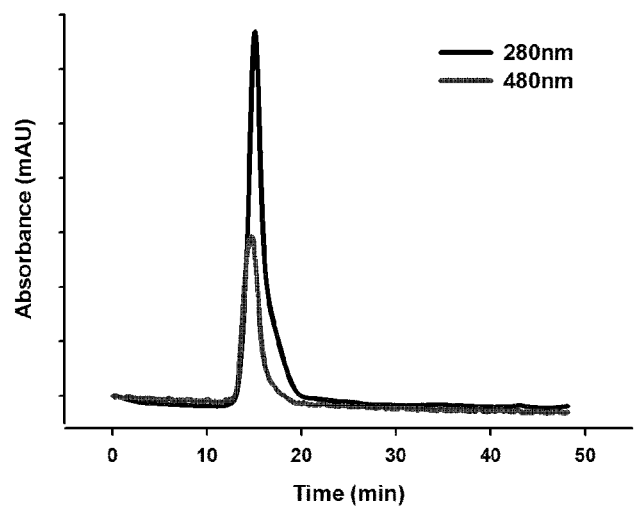
FIG. 4B is a chromatogram representing the result of FPLC analysis of a doxorubicin-encapsulated nanocage (FH-SIRPα)
Figure 4C:
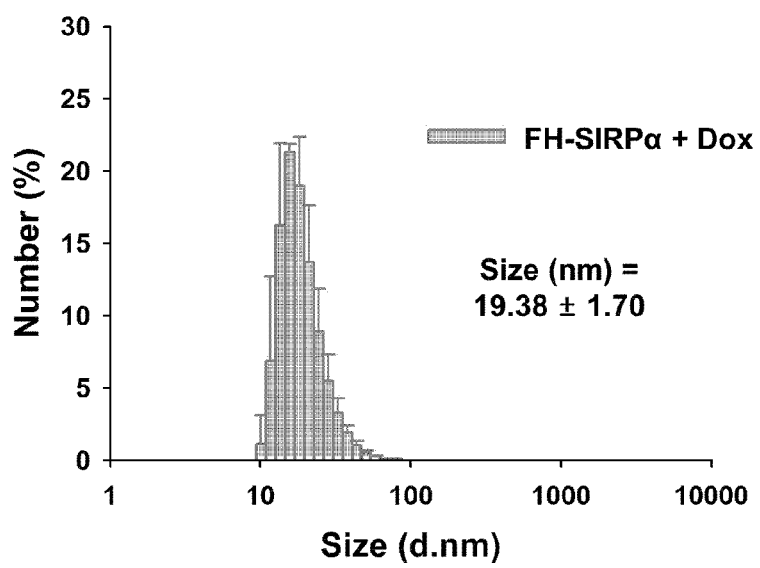
FIG. 4C is a histogram showing the result of particle size distribution analysis.
Figure 4D:
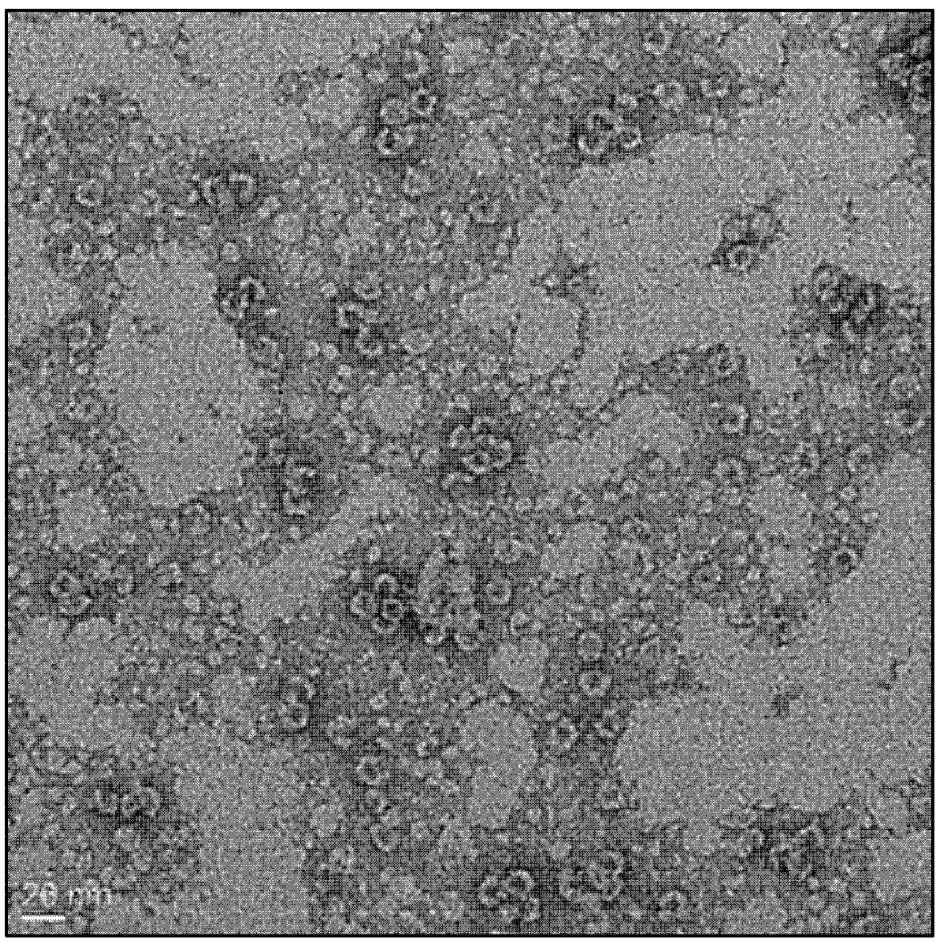
FIG. 4D is a transmission electron microscopic image of doxorubicin-encapsulated nanocage (FH-SIRPαHV-Dox).

As a result, as shown in FIG. 4B, the doxorubicin nanocage complex of the present invention also showed a single peak on the FPLC, and the absorbance at 480 nm for doxorubicin measurement also showed the same retention time as the protein detection at the wavelength of 280 nm, thus it was indirectly confirmed that doxorubicin was successfully loaded inside the nanocage of the present invention. As a result of the particle size analysis, it was confirmed that the nanoparticles having a particle size of 10 to 20 nm as shown in FIG. 4C and the transmission electron microscope photographic image also showed spherical nanoparticles as shown in FIG. 4D.

Figure 5A:
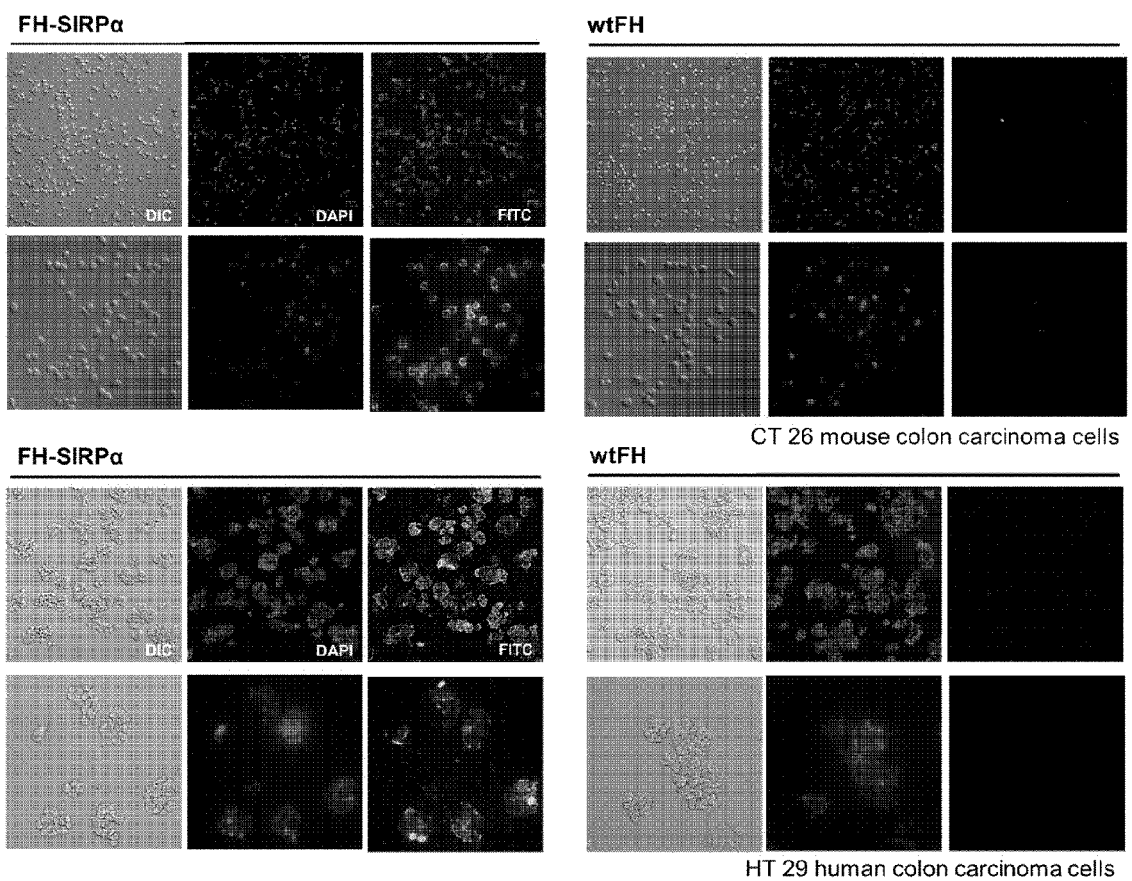
FIGS. 5A-5B show experimental results of CD47 binding ability of the nanocage prepared according to an embodiment of the present invention.

Experimental Example 2: Evaluation of Adhesion Ability of Cancer Cells In Vitro 2-1: Fluorescence Microscopic Analysis The present inventors performed fluorescence microscopy to confirm whether the FH-SIRPα HV nanocage prepared in Example 1 specifically binds to CD47 on the surface of cancer cells. Specifically, CT26 mouse colorectal cancer cell line and HT29 human colorectal cancer cell line were inoculated at a concentration of $3 \times 10^4$ cells/ml. Then, after treating 400 nM of FH-SIRPα HV nanocage prepared in Example 1-1 or same amount of wild-type ferritin heavy chain nanocage as control group, anti-ferritin primary antibody (Abcam, Cambridge, UK) and FITC-conjugated anti-mouse rabbit secondary antibody (Jackson ImmunoResearch, Suffolk, UK) were treated and then fluorescence microscopic images were obtained. As a result, FITC fluorescence was observed in most cancer cells as shown in FIG. 5A, confirming that the FH-SIRPα HV nanocage of the present invention binds well to cancer cells. The affinities and kinetics of FH-SIRP α HV nanocage binding human or mouse CD47 were analyzed by surface plasmon resonance (SPR) analysis and the results are shown in Table 1 below.

TABLE 1

|  | Human CD47 | | | Mouse CD47 | | |
| --- | --- | --- | --- | --- | --- | --- |
| Molecule | $k_a$, $M^{-1} s^{-1}$ | $k_d$, $s^{-1}$ | $k_d$, M | $k_a$, $M^{-1} s^{-1}$ | $k_d$, $s^{-1}$ | $k_d$, M |
| FH-SIRPα | $5.0 \times 10^6$ | $2.4 \times 10^{-7}$ | $4.8 \times 10^{-14}$ | $1.1 \times 10^6$ | $4.1 \times 10^{-4}$ | $3.7 \times 10^{-10}$ |
| mSirpα | $7.0 \times 10^6$ | $3.7 \times 10^{-5}$ | $5.4 \times 10^{-12}$ | $1.8 \times 10^6$ | $1.1 \times 10^{-2}$ | $6.2 \times 10^{-9}$ |

2-2: Analysis of the Ability of Various Nanocages to Bind Cancer Cells

In order to confirm the affinity of cancer cells for nanocages produced using various SIRP proteins prepared in Examples 1-2 to 1-5, respectively in addition to the nanocage prepared in Example 1-1, flow cytometry was performed. Particularly, HT29 human colon cancer cells were seeded into $2\times10^5$ cells/ml and the wild-type ferritin heavy chain nanocage as a control group, the FH-SIRPα HV nanocage prepared in Example 1-1, the FH-hSIRPα WT nanocage prepared in Example 1, the FH-SIRPγ WT nanocage prepared in Example 1-3 and the FH-SIRPγ V2 nanocage prepared in Example 1-5 were treated at the concentration of 20, 200, 400 or 600 nM, respectively, and the degree of cell binding was measured. Particularly, after treating anti-ferritin heavy chain primary antibody (Abcam, Cambridge, UK, 1:200) and an Alexafluor 488-conjugated donkey anti-rabbit secondary antibody (Jackson ImmunoResearch, Suffolk, UK, 1:400), the cells were sorted according to fluorescence intensity through flow cytometry analysis.

Figure 5B:
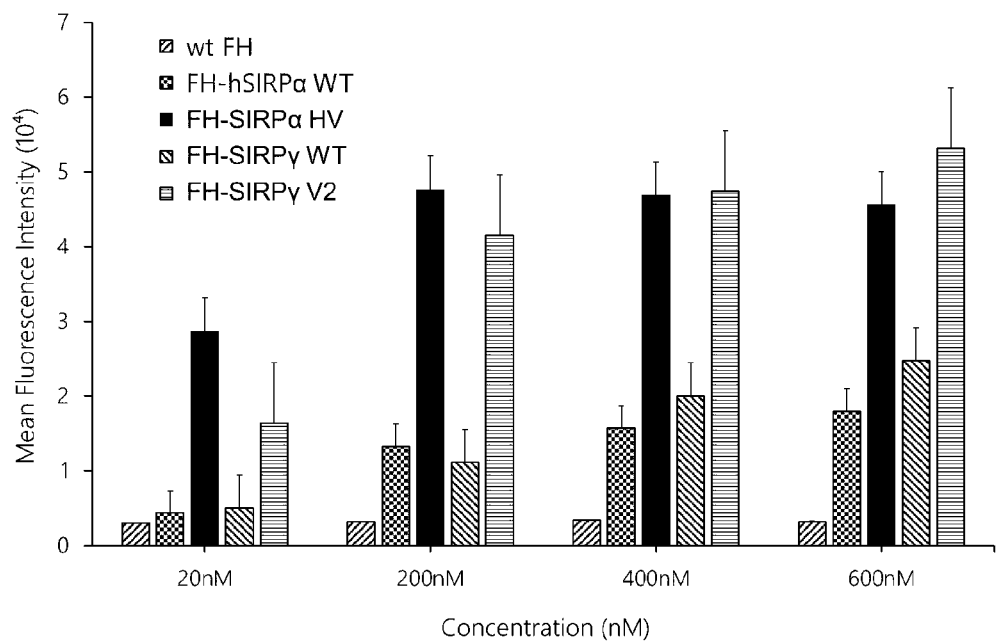

As a result, as shown in FIG. 5B, the nanocage composed of the wild-type ferritin heavy chain protein as a control group did not bind to cancer cells even when the concentration increased, while the SIRPα wild-type or SIRPγ wild-type protein binds to cancer cells in a concentration-dependent manner. However, the degree of binding was lower than that using the SIRPα high affinity variant. Interestingly, in the case of a nanocage (FH-SIRPγ V2 nanocage) in which amino acids of a SIRPγ protein substituted with amino acids corresponding to the mutation position of the SIRPα high-affinity variant except for valine, which is the $27^{th}$ amino acid residue, is equivalent to the performance of SIRPα HV nanocage.

Experimental Example 2: Analysis of In Vitro Phagocytic Activity of Phagocytic Cells Against Cancer Cells The present inventors then investigated whether FH-SIRPα nanocage according to an embodiment of the present invention binds CD47 on the surface of cancer cells and improves phagocytosis of cancer cells by phagocytic cells using flow cytometry and fluorescence microscopy.

Particularly, the present inventors observed the phagocytic action of macrophages and dendritic cells against tumor cells through FACS analysis. First, $3\times10^5$ cells/ml of bone marrow-derived macrophages (BMDMs) pre-stained with CellTracker Green (Thermo Fisher Scientific, USA) and (a) $1.25\times10^6$ cells/ml of human Raji Burkitt lymphoma cells, (b) human HT-29 colorectal cancer cells, (c) mouse 4T1 breast cancer cells, (d) mouse CT26 colorectal cancer cells and (e) mouse CT26.CL25 colorectal cancer cells overexpressing β-galactosidase pre-stained with pHrodo Red SE, respectively were seeded in RPMI medium and buffer only (control), the ferritin-SIRPα fusion nanocage (FH-SIRPα HV) of the present invention, the wild-type ferritin heavy chain nanocage (wtFH) and the monomeric SIRPα (mSIRPα) were treated at the concentration of 400 nM, respectively. In addition, $3\times10^5$ cells/ml of bone marrow-derived dendritic cells (BMDCs) pre-stained with CellTracker Green (Thermo Fisher Scientific, USA) and (a) $1.25\times10^6$ cells/ml of human Raji Burkitt lymphoma cells, (b) human HT-29 colorectal cancer cells, (c) mouse 4T1 breast cancer cells, (d) mouse CT26 colorectal cancer cells and (e) mouse CT26.CL25 colorectal cancer cells overexpressing β-galactosidase pre-stained with pHrodo Red SE, respectively were seeded in RPMI medium and buffer only (control), the FH-SIRPα HV, wtFH and the mSIRPα were treated at the concentration of 400 nM, respectively. After the treatment FACS analysis was performed. The phagocytosis rate was determined by the following formula.

Phagocytosis rate=macrophages or dendritic cells that phagocytized cancer cells (simultaneous detection of red and green)/total macrophages or dendritic cells (red)×100.

The CT26.CL25 cell line is a cell line prepared to express the β-galactosidase protein in the CT26 cell line. Therefore, it is being used to investigate the immunogenicity of β-galactosidase antigen protein. In order to effectively induce anti-cancer immunity, the antigen protein is efficiently delivered to the macrophages and dendritic cells, thereby stimulating the cytotoxic T cells effectively by increasing the rate of expression of the β-galactosidase peptides derived from the tumor-specific antigen by MHC class I molecules. The present inventors performed the above-described experiments in order to confirm whether β-galactosidase protein as a model cancer antigen can be effectively delivered to macrophages and dendritic cells and activate the antigen-presenting cell function thereby, and ultimately whether it can be used for anticancer therapy by inducing cancer antigen-specific immune responses and effectively stimulating cytotoxic T cells thereby.

As a result, as shown in FIGS. 6A, 6B and 6F to 6H, the phagocytosis of cancer cells by macrophages and dendritic cell treated with the negative control or the wild-type ferritin heavy chain nanocage was very low, but the recombinant SIRPα and the FH-SIRPα HV nanocage according to one embodiment of the present invention were significantly increased in both BMDMs and BMDCs compared with the control group. In particular, in the case of CT26.CL25 cells overexpressing β-galactosidase, the phagocytosis cancer cells by macrophages and dendritic cells was remarkably increased compared with recombinant SIRPα, and nearly doubled in the case of macrophages (see FIG. 6A).

In order to confirm whether the ferritin heavy chain nanocages prepared in Examples 1-2 to 1-5 also exhibit phagocytic activity of cancer cells by macrophages, the present inventors cocultured bone marrow-derived macrophages ($2\times10^5$ cells/ml) and CT26.CL25 mouse colon cancer cells ($8\times10^5$ cells/ml) at $37°$ C. for 4 hours and then the macrophages were stained with 1 mM of CellTracker Deep Red and cancer cells were stained with 0.5 mM of CellTracker Green. After the staining, phagocytosis rate of macrophages against cancer cells were determined by counting phagocytized cancer cells by the macrophages.

Figure 6A:
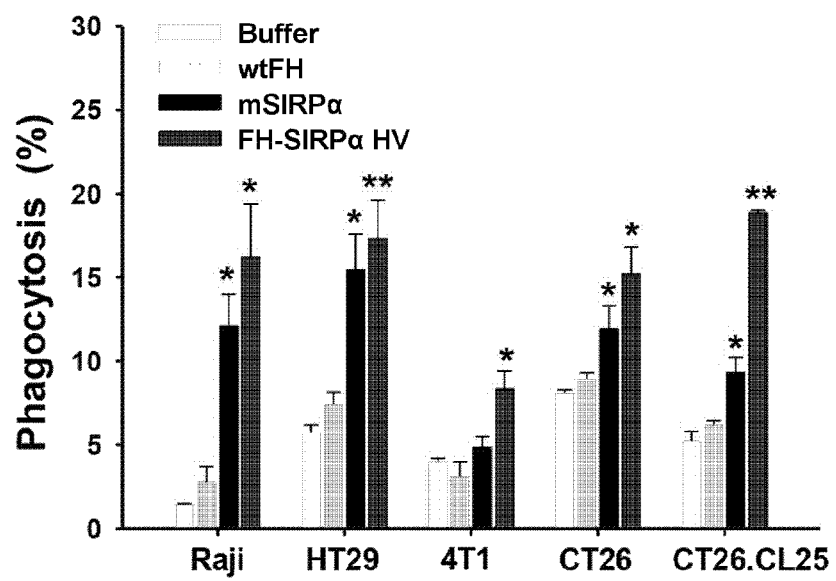
FIGS. 6A-6H show phagocytosis of cancer cells by macrophages treated with nanocages produced by self-assembly of ferritin heavy chain protein-SIRPα fusion protein according to an embodiment of the present invention.
Figure 6B:
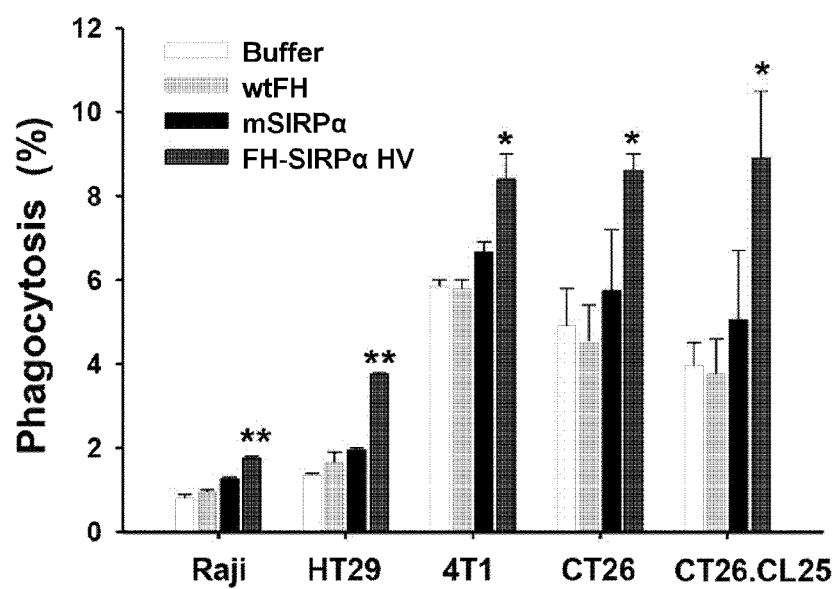
Figure 6C:
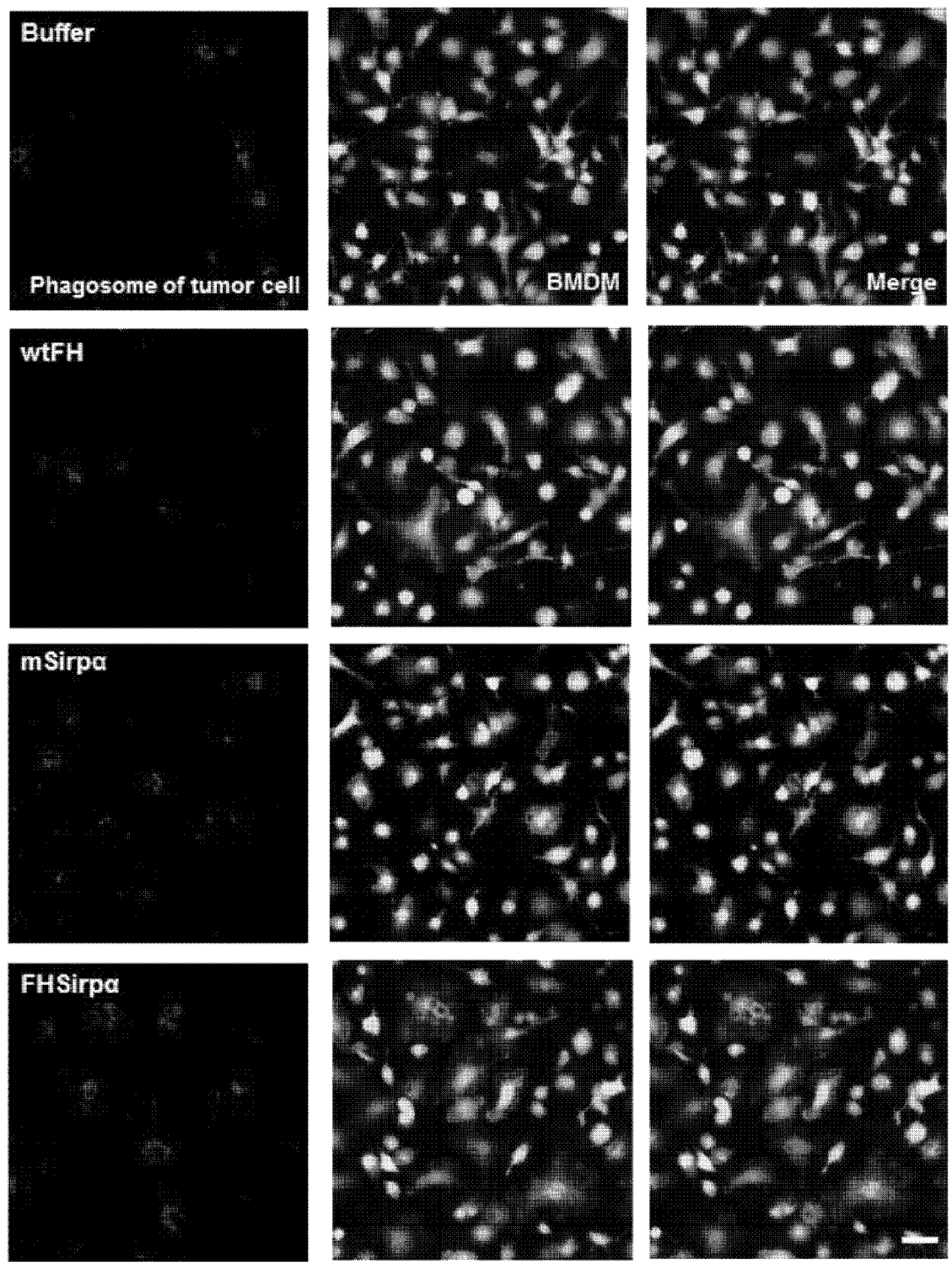
Figure 6D:
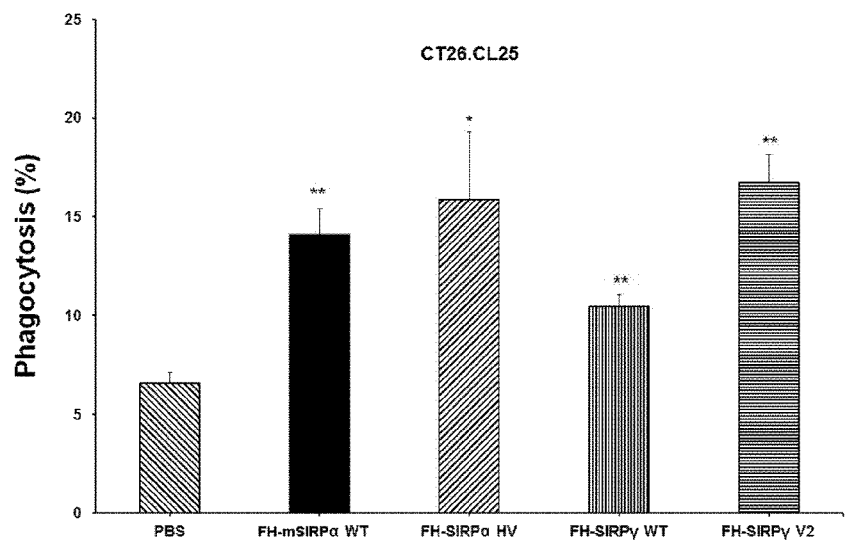

As a result, as shown in FIG. 6D, both the human SIRPα wild-type protein and the human SIRPγ wild-type protein exhibited phagocytic activity against cancer cells. Nanocage (FH-SIRPγ V2) using the SIRPγ variant showed higher phagocytosis activity against cancer cells.

Figure 6E:
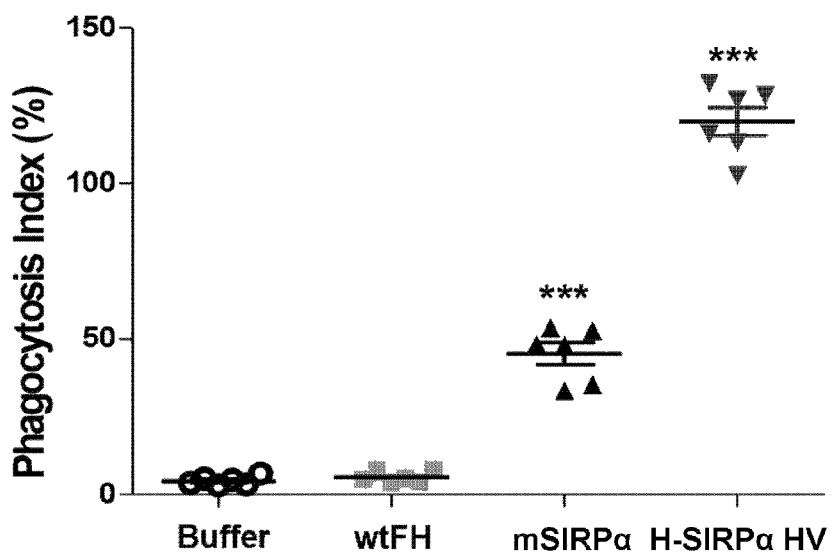
Figure 6F:
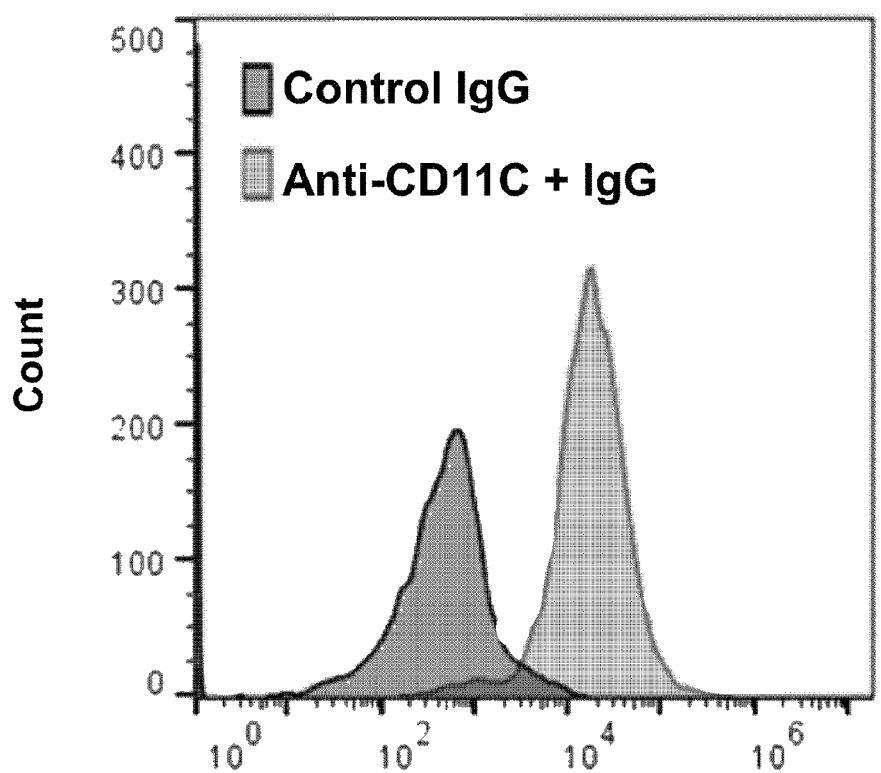
Figure 6G:
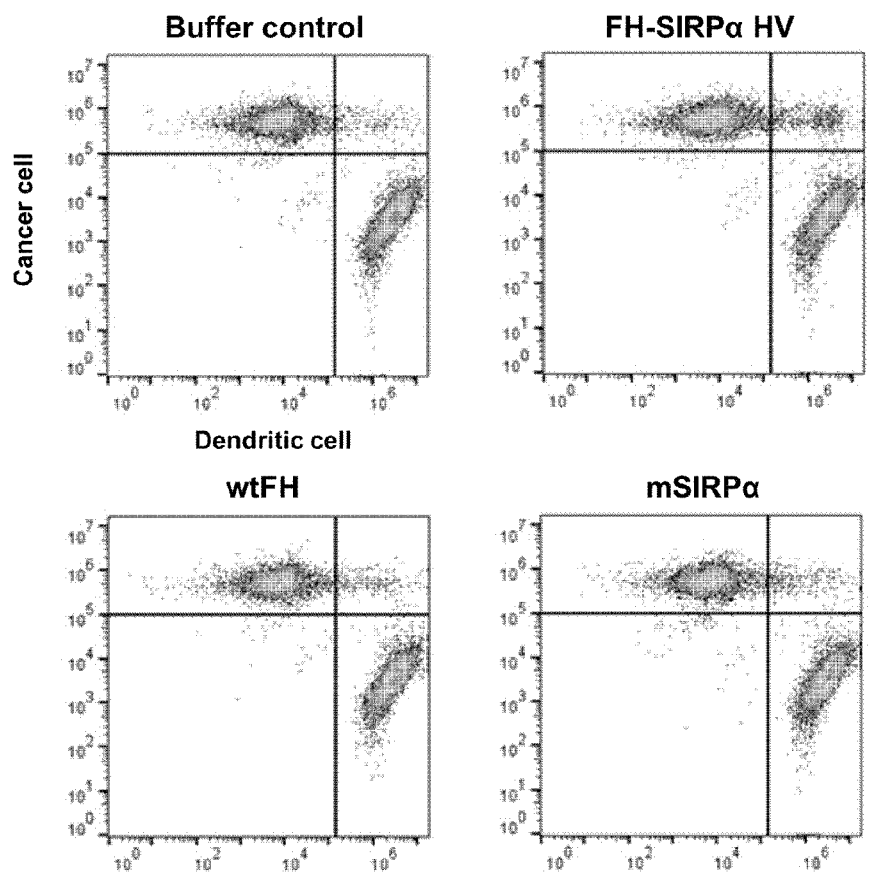
Figure 6H:
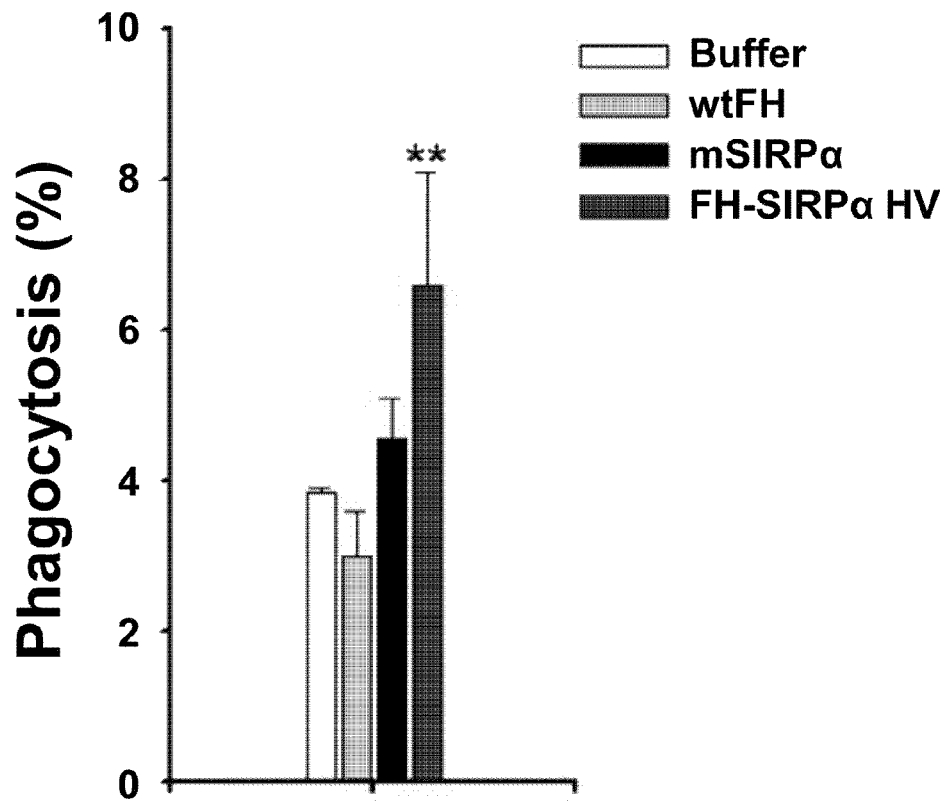

In addition, the phagocytosis rate of cancer cells by bone marrow-derived macrophages (BMDMs) was quantitated as a phagocytosis index (PI) expressed as a percentage by counting the number of cancer cells per BMDM cell by microscopic observation. As a result, as shown in FIGS. 6C and 6E, PI values were significantly higher than recombinant SIRPα. This shows that the FH-SIRPα nanocage of the present invention has a characteristic of further enhancing the phagocytosis itself as well as increasing the proportion of macrophages that perform phagocytosis. In particular, the FH-SIRPα nanocage of the present invention exhibited a similar or higher phagocytosis rate than the recombinant SIRPα.

Experimental Example 3: Analysis of In Vivo Anti-Cancer Effect

3-1: Cancer Growth Inhibition Assay

The present inventors confirmed that the FH-SIRPα nanocage of the present invention had excellent anticancer activity under the in vitro conditions and confirmed that the same anti-cancer effect was observed in the animal model experiment. The antitumor activities of the ferritin heavy chain nanocage prepared in Examples 1-1 to 1-5 and the doxorubicin nanocage complex prepared in Example 3 were examined. Particularly, Balb/c wild type mice were used as the experimental animals, and experiments on the above experimental animals were carried out according to the regulations of the KIST animal ethics committee.

First, in order to measure the in vivo anticancer activity of the various ferritin heavy chain nanocages prepared in Examples 1-1 to 1-5, $1 \times 10^6$ cells of CT26.CL25 cancer cells expressing β-galactosidase were subcutaneously injected on the left side of Balb/c wild-type mice in order to induce cancer and then each experimental substance (buffer only, FH-mSIRPα WT, FH-SIRPα HV, FH-SIRPγ WT and FH-SIRPγ V2) was injected intratumorally at dose of 28 mg/kg) after 5 day of tumor inoculation, and the length (L) and the width (W) of the tumor tissues were measured using a caliper at intervals of 3 days (FIG. 7A), and then the volume of tumor tissue was calculated using the following formula:

$$\text{Tumor tissue volume } (V \text{ [mm}^3\text{]}) = (L \text{ [mm]}) \times (W \text{ [mm]})^2 \times 0.5$$

Figure 7A:
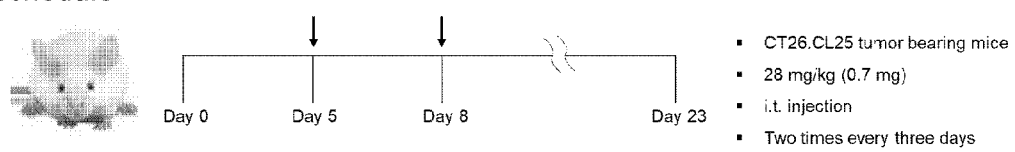
FIGS. 7A-7G show the results of a nanocage (FH-SIRPα) produced by self-assembly of a ferritin heavy chain protein-SIRPα fusion protein according to an embodiment of the present invention and a nanocage complex encapsulating doxorubicin (DOX in FH-SIRPα).
Figure 7B:
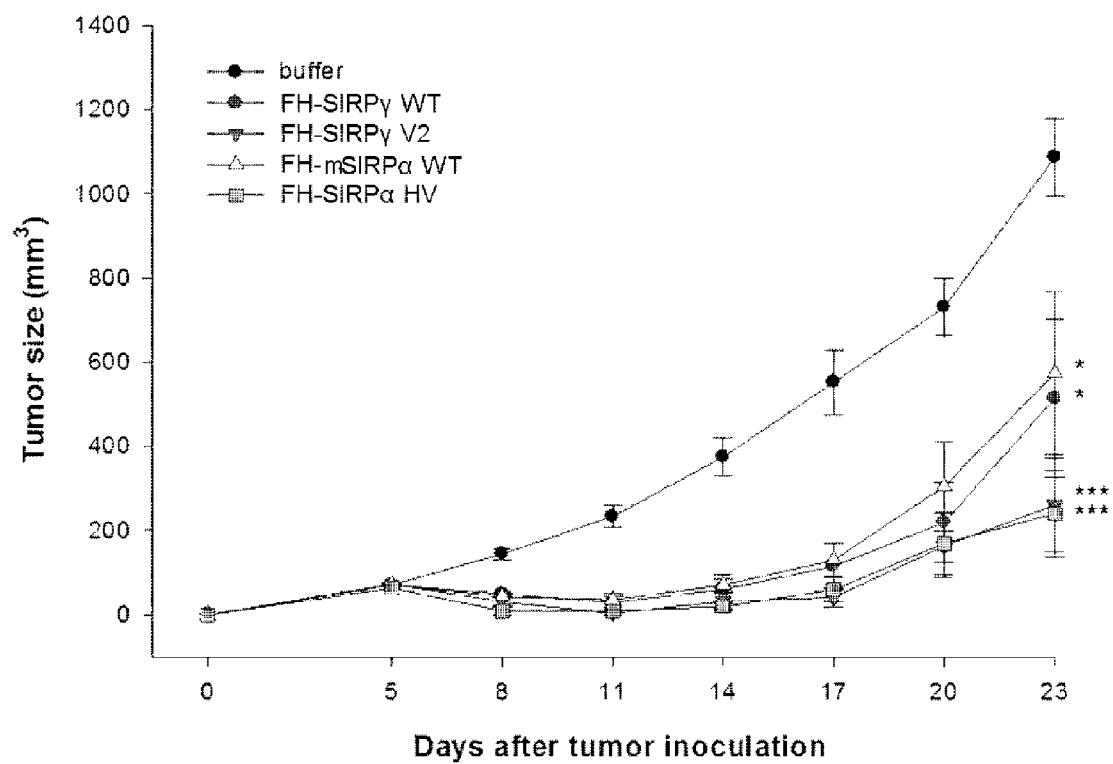
Figure 7C:
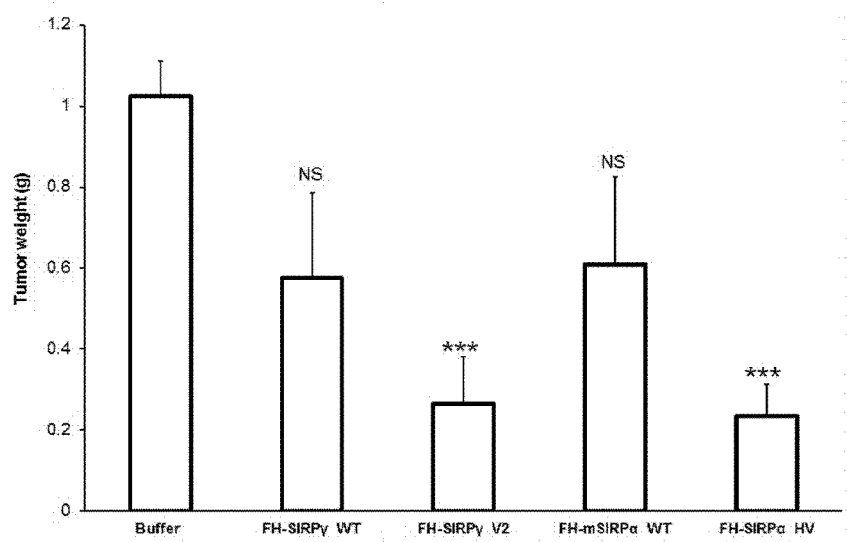

As a result, as shown in FIGS. 7B and 7C, the various ferritin heavy chain nanocages produced in Examples 1-1 to 1-5 of the present invention significantly inhibited the growth of cancer cells as compared with the control group. When SIRPα wild-type and SIRPγ wild-type were used, the antitumor activity was somewhat lowered. On the other hand, high-affinity variants of SIRPα and SIRPγ showed very good antitumor activity.

Figure 7D:
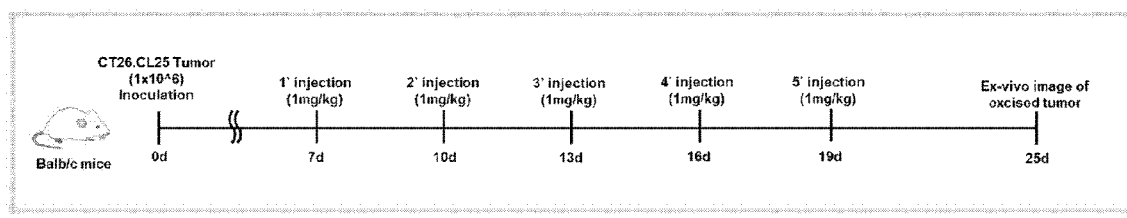

In addition, the present inventors investigated the in vivo anticancer activity of the doxorubicin-encapsulated nanocage complex prepared in Example 3 above. Particularly, $1 \times 10^6$ cells of CT26.CL25 cancer cells were subcutaneously injected into the above Balb/c wild-type mice to induce cancer. On the $7^{th}$ day after the injection of cancer cells, 1 mg/kg of each test substance (buffer only, doxorubicin-loaded FH-SIRPα HV nanocage, doxorubicin-loaded ferritin heavy chain nanocage, doxorubicin+recombinant SIRPα, doxorubicin only, FH-SIRPα HV nanocage, ferritin heavy chain nanocage or recombinant SIRPα) was injected first by the tail vein and further injected four times at interval of 3 days at the same dose. The animals were sacrificed for 25 days after the injection of cancer cells, and the tumor tissues were excised and an ex vivo image was taken (FIG. 7D). Further, the volume of the tumor tissue over time before the sacrifice of the experimental animals was recorded from 7 days after the injection of cancer cells at the interval of 3 days by calculating using the following formula after measuring length (L) and width (W) of tumor tissues using a caliper:

$$\text{Tumor tissue volume } (V \text{ [mm}^3\text{]}) = (L \text{ [mm]}) \times (W \text{ [mm]})^2 \times 0.5$$

Figure 7E:
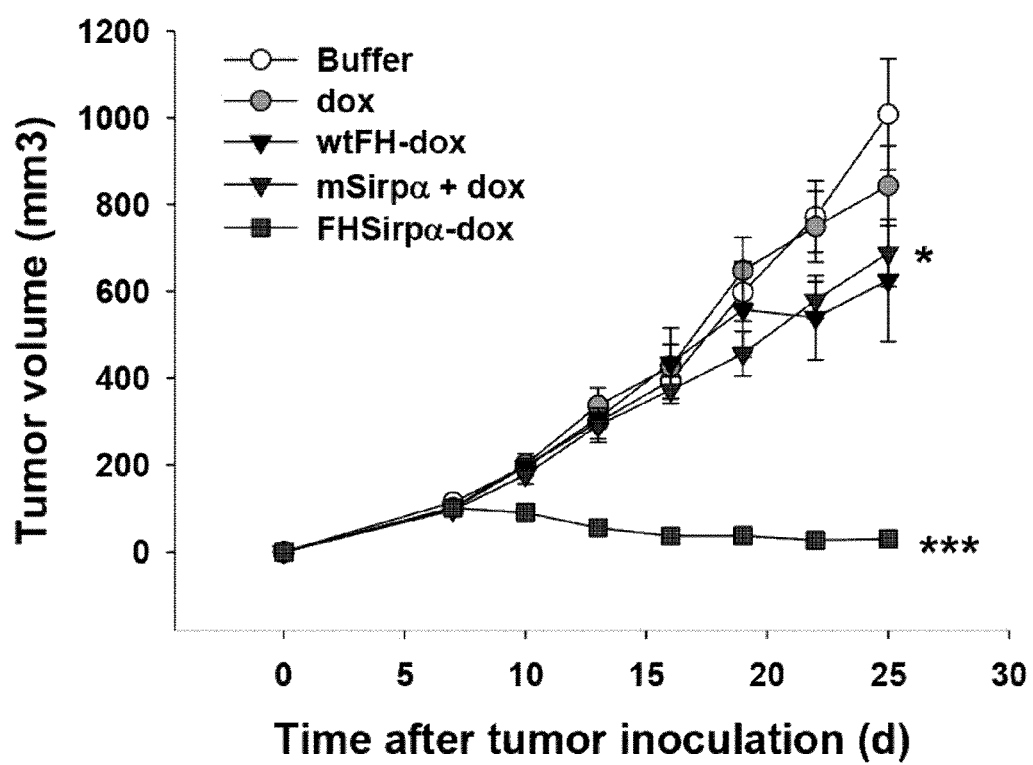

As a result, as shown in FIG. 7E, the volume of the tumor exceeded 1,000 mm³ in the control group (only buffer injection) and the recombinant SIRPα alone group, and the effect of doxorubicin alone treatment was also insignificant.

Figure 7F:
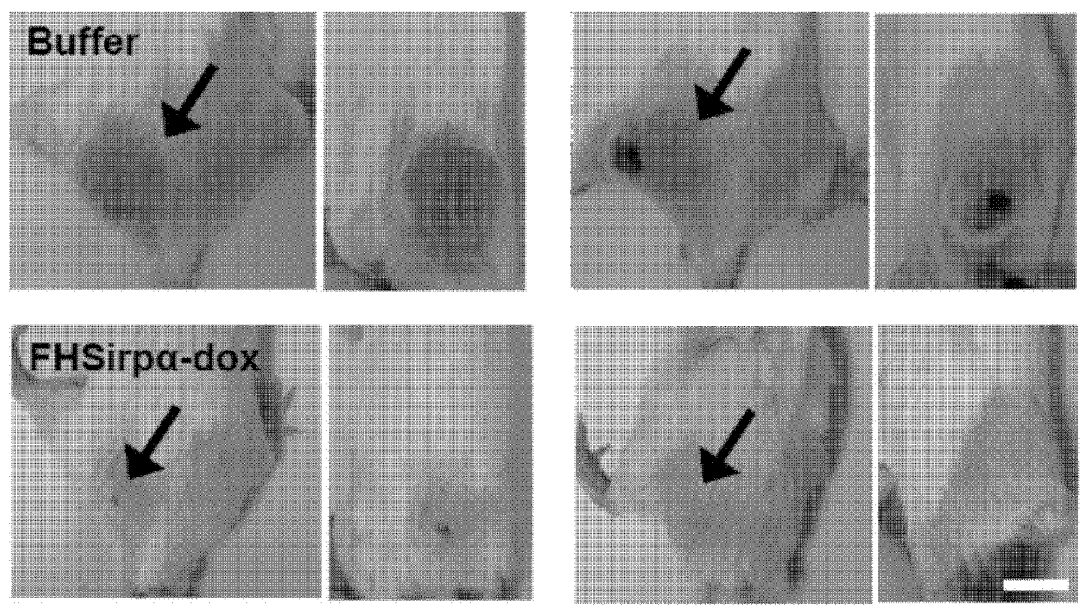
Figure 7G:
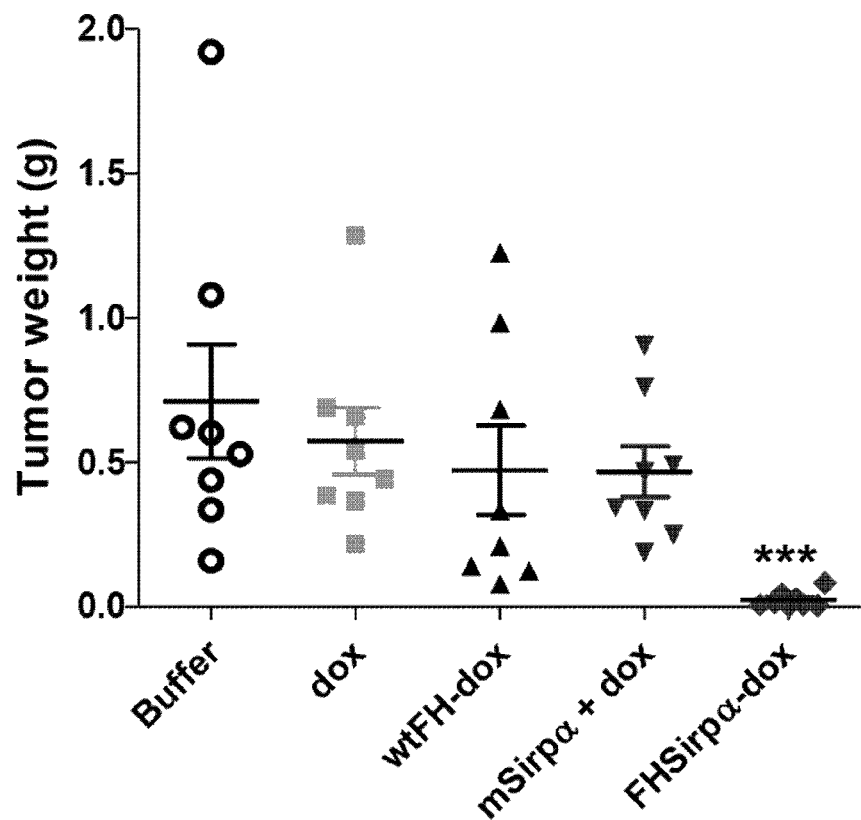

In addition, as shown in FIGS. 7F and 7G, the nanocage complex and the wild-type ferritin heavy chain nanocage in which doxorubicin was loaded in the ferritin nanocage showed an anticancer effect but did not sufficiently inhibit the growth of cancer cells. On the other hand, the doxorubicin-encapsulated FH-SIRPα nanocage complex according to an embodiment of the present invention almost completely inhibited the growth of cancer cells, so that cancer cells could not be recognized by the naked eye.

The results were slightly different from those of the in vitro tests. When administered with doxorubicin alone or recombinant SIRPα alone and the combination of recombinant SIRPα and doxorubicin, which caused the phagocytosis of cancer cells by macrophages in vitro tests, the anticancer effect was not so significant, and it is a very remarkable result.

In addition, when measuring tumor tissues excised from sacrificed animals after 25 days of cancer cell injection, it was confirmed that the doxorubicin-encapsulated FH-SIRPα nanocage complex of the present invention showed a significant cancer cell reduction effect, while the cancer cell growth inhibiting effects were limited when doxorubicin-encapsulated ferritin heavy chain nanocage, the combination of doxorubicin and mSIRPα, or doxorubicin alone were administered. Interestingly, recombinant SIRPα alone had the same tumor volume as the control group, indicating recombinant SIRPα itself was not effective in vivo. As shown in FIGS. 7F and 7G, the FH-SIRPα nanocage and doxorubicin-encapsulating FH-SIRPα nanocage complex of the present invention exhibit an excellent anticancer activity without variation according to animals.

3-2: Immunohistochemical Analysis

In order to confirm whether the result of Experimental Example 3-1 was the effect of recruiting immune cells to the tumor tissue, the present inventors cryo-sectioned the tumor tissues excised in Experimental Example 3-1 and performed immunohistochemical analysis on T cell markers CD8.

In particular, tumor tissues excised from experimental animals in Experimental Example 3-1 administered with doxorubicin-loaded FH-SIRPα HV nanocage complex were embedded in OCT, frozen at −70° C., 4 μm-thick cryo-sections were prepared, and reacted with anti-CD8 antibody (BD Bioscience, USA). The sections were washed twice, and incubated with HRP-conjugated secondary antibody (Vector Laboratories, USA). After washing twice, DAB was used to induce color reaction. The result of staining was photographed with an optical microscope.

Figure 8A:
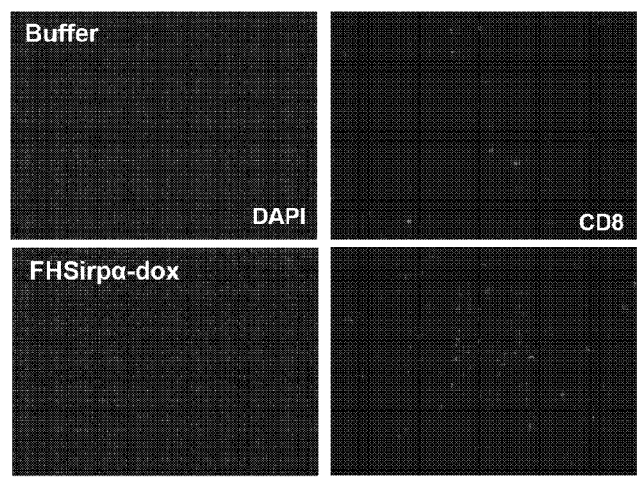
FIGS. 8A-8D represent immunohistochemical analysis showing the accumulation of CD8$^+$ T cells in the tumor area after administration of buffer only or nanocage complex encapsulating doxorubicin according to an embodiment of the present invention to experimental animals prepared by transplanting the tumor.
Figure 8B:
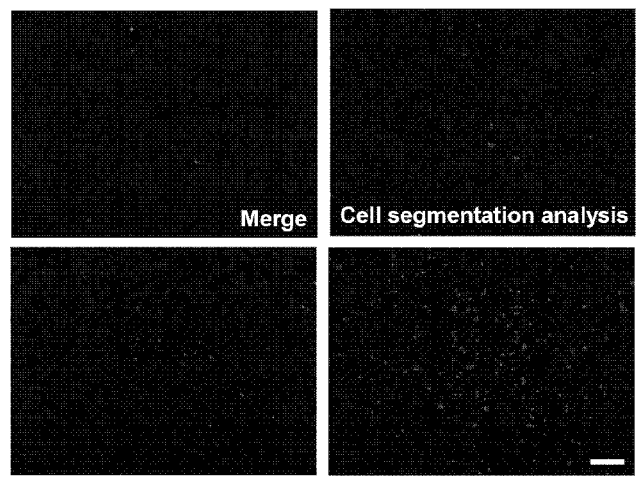

As a result, CD8 were stained positively in cancer tissues, as shown in FIGS. 8A and 8B. This demonstrates that CD8$^+$ T cells were mobilized into tumor tissues, suggesting that the anticancer effect is due to the synergistic action doxorubicin and immune cells recruit by CD47 masking by SIRPα.

3-3: Analysis of Antigen-Induced Immune Response

The present inventors investigated the cellular immunity against CT26.CL25 cancer cells in mouse spleen by doxorubicin-loaded FH-SIRPα HV nanocage complex in order to confirm whether the above-described immune response was cancer cell-specific. That is, the level of interferon-gamma (INF-γ) of T cells specific to β-galactosidase, an antigen of CT26.CL25, was quantified by ELISA (R&D Systems, Inc., USA). Three mice per group were selected from the mice treated in the same manner as in Experimental Example 3-1, the spleen was removed from each mouse, the spleen tissue was transferred to a sterilized petri dish, and the spleen tissue was ground using a cell strainer. And then cells were separated from the tissue epithelium. All the contents in the Petri dish were transferred to a 15 ml tube, filled with RPMI 1640 medium, centrifuged at 1,500 rpm for 5 minutes. After removing supernatant, red blood cells lysis buffer (Sigma-Aldrich, Germany) were added to pellet in order to hemolyze red blood cells. Cells contained in the tubes were washed with PBS and then suspended in RPMI 1640 medium to isolate splenocytes. Isolated splenocytes were seeded in 24-well plates at $1 \times 10^6$ cells/ml and promoting activation of $CD8^+$ cells secreting INF-γ by treating with 5 μg/ml of β-Gal peptide (TPHPARIGL, SEQ ID NO: 90, including H2-Ld-restricted epitope naturally engineered including amino acids residues 876-884 of β-galactosidase), AH1 (SPSYVYHQF, SEQ ID NO: 91, comprising CTL determinant derived from CT26) and PIA peptide (negative control) for 24 hours, respectively. The supernatant was then separated and level of INF-γ was quantified by ELISA (R&D Systems, Inc, USA).

Figure 8C:
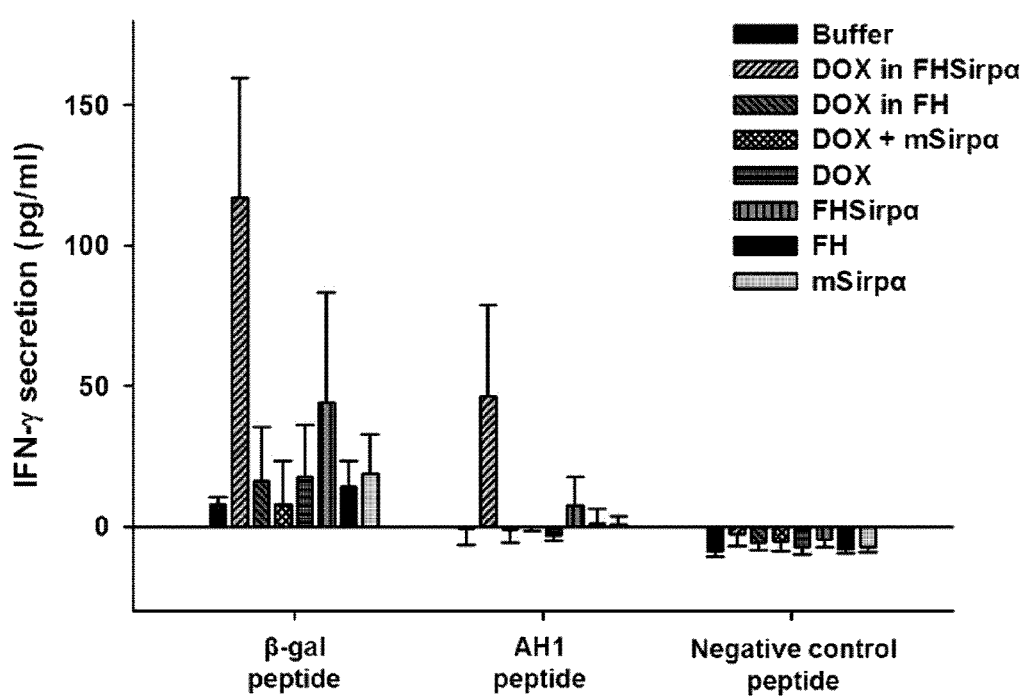

As a result, as shown in FIG. 8C, when the β-Gal peptide or the AH1 peptide were treated to the splenic immune cells isolated from the animals administered with FH-SIRPα HV nanocage or doxorubicin-loaded FH-SIRPα HV nanocage complex according to an embodiment of the present invention, the expression of IFN-γ was increased significantly. In particular, in the case of FH-SIRPα HV nanocage complex loaded with doxorubicin according to an embodiment of the present invention, the degree of expression of IFN-γ was 100 μg/ml or more, and the degree of immunogenic activation against cancer cells was very high. Other drugs, such as the combination of doxorubicin and recombinant SIRPα, showed little or no effect. In the case of FH-SIRPα HV nanocage complex loaded with doxorubicin, β-galactosidase protein is efficiently delivered to macrophages and dendritic cells to activate antigen-presenting cells, and ultimately to stimulate cytotoxic T cells effectively. It was confirmed that the immune response specific to CL26.CL25 cancer cells was efficiently induced.

The present inventors investigated in vivo cross-prime ability of antigen presenting cells against cancer by doxorubicin-loaded FH-SIRPα HV nanocage complex. For in vivo T cell-priming assays, B16.OVA cells ($1 \times 10^6$) were subcutaneously injected into the left flank of C57BL/6 mice. After allowing tumors to grow to reach a volume of around 100 mm$^3$, mice were treated with doxorubicin-loaded FH-SIRPα HV nanocage complex according to an embodiment of the present invention, FH-SIRPα HV nanocage, doxorubicin alone or buffer. All treatments were administered every 3 days for a total of two doses by intravenously injecting an amount equivalent to a dose as used for antitumor therapy as described below. 10 days after the final treatment, $2 \times 10^6$ OT-1 $CD8^+$ T cells isolated from OT-1 mice using a negative CD8 isolation column (R&D Systems, Inc, US), labeled with 10 μM CFSE (Thermo-Fisher Scientific, USA), were adoptively transferred into the above-treated mice. Tumor-draining lymph nodes (DLN) were dissected on day 3 and used for an analysis of proliferation of OT-1 $CD8^+$ T cells by an Accuri C6 flow cytometer.

Figure 8D:
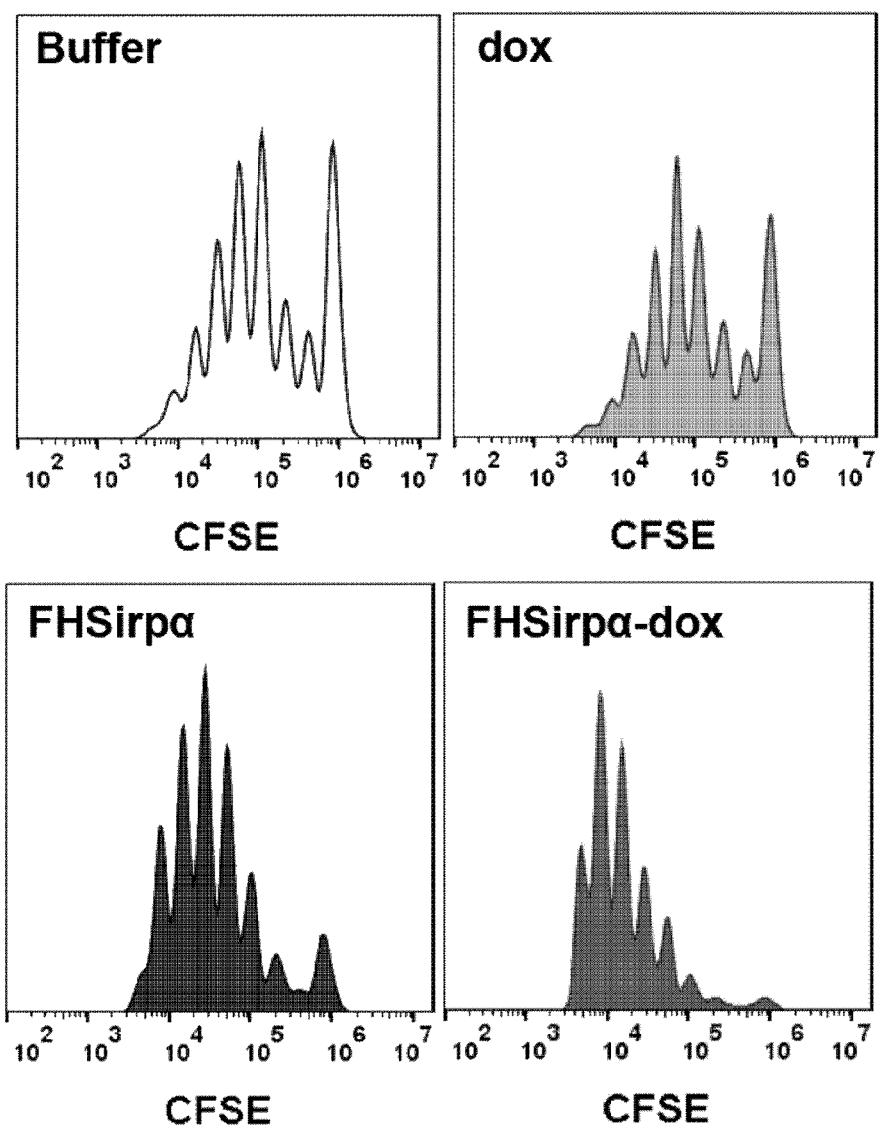

As a result, as shown in FIG. 8D, FH-SIRPα HV nanocage complex loaded with doxorubicin treatment increased proliferation of OT-1 $CD8^+$ T cells to a greater extent than other groups. These results demonstrate that FH-SIRPα HV nanocage complex loaded with doxorubicin can induce not only enhancement of phagocytosis but also increased processing of tumor antigens and their presentation to $CD8^+$ T cells.

Experimental Example 4: Analysis of Anticancer Memory Effect

The present inventors have hypothesized that the effect of FH-SIRPα nanocage according to an embodiment of the present invention is due to the recruiting of immune cells from the results of Experimental Example 3. Thus, the present inventors analyze growth of secondary cancer transplanted to other site and counted survival rate of the experimental animals after excising primary tumor tissues from the experimental animals.

Figure 9A:
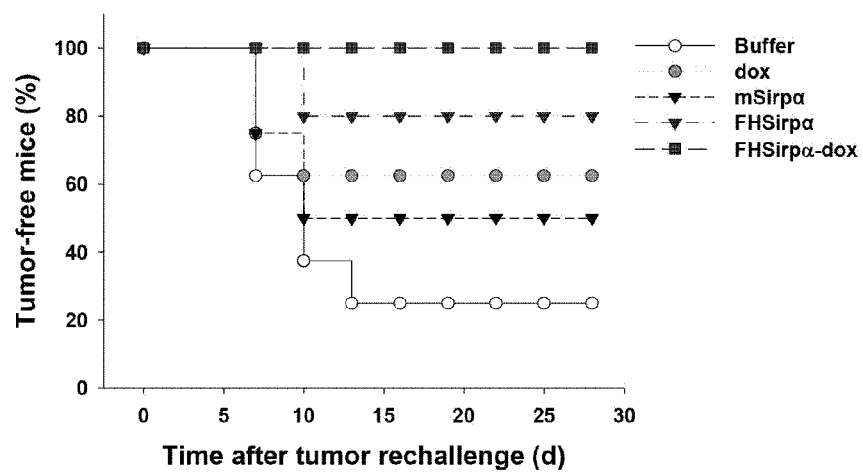
FIGS. 9A-9C show experimental results of analysis memory effect of the anticancer nanocage according to an embodiment of the present invention.
Figure 9B:
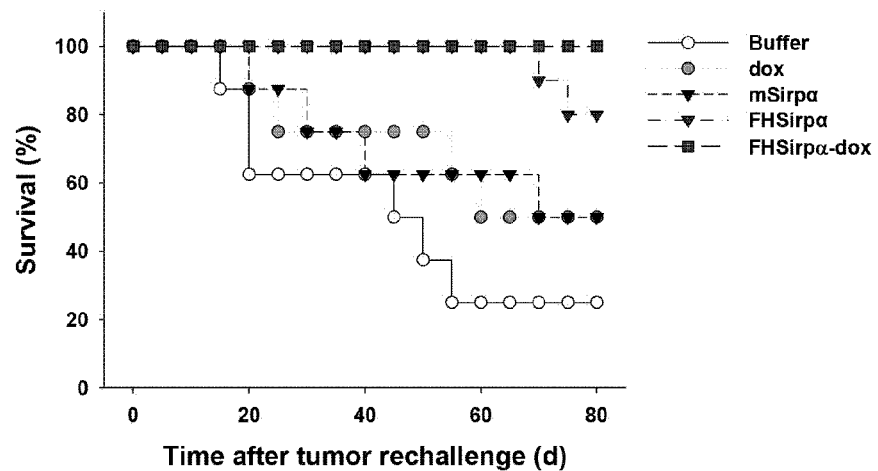
Figure 9C:
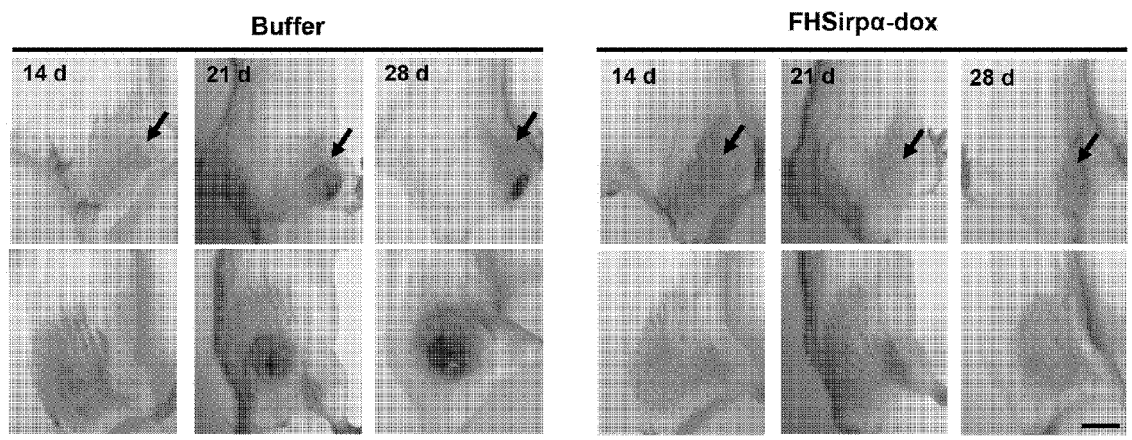
Figure 10A:
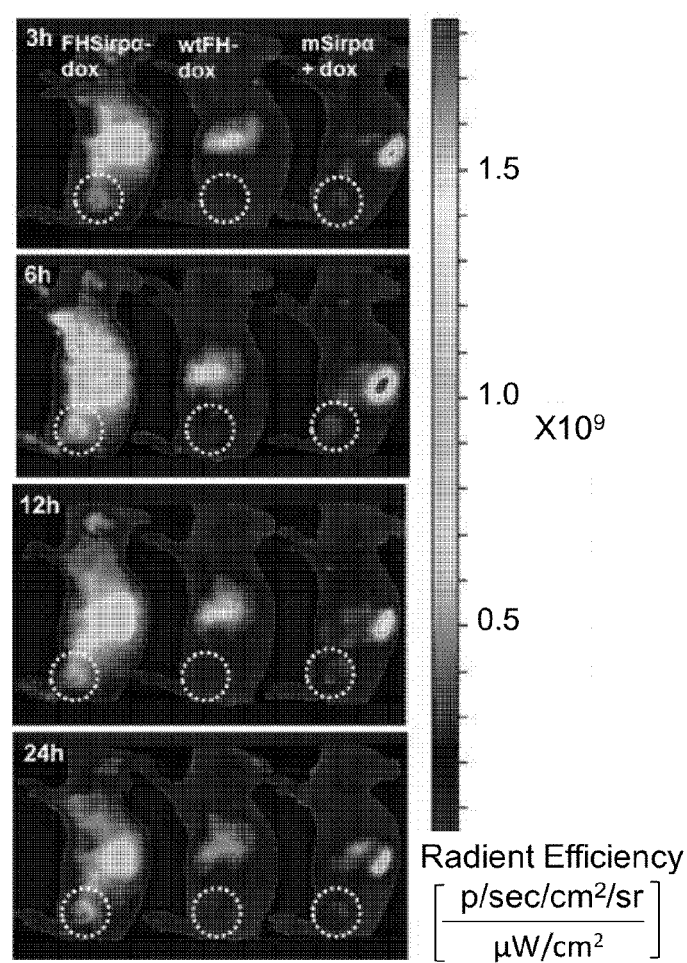
FIGS. 10A-10D show the delivery efficiency of FH-SIRPα HV-Dox to the tumor microenvironment.
Figure 10B:
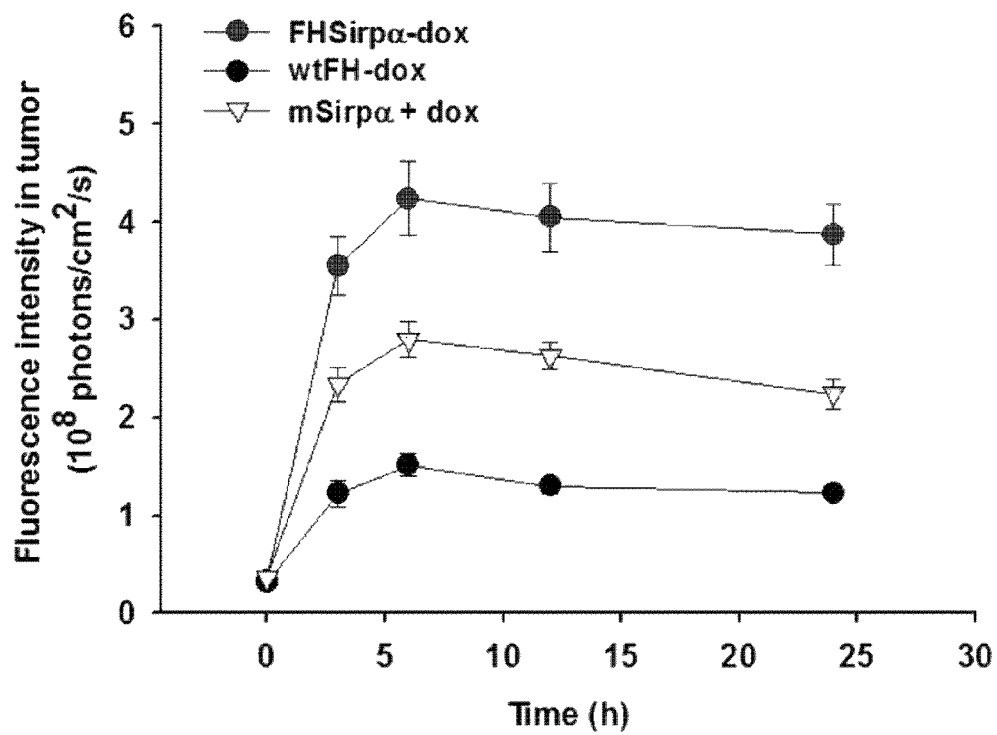
Figure 10C:
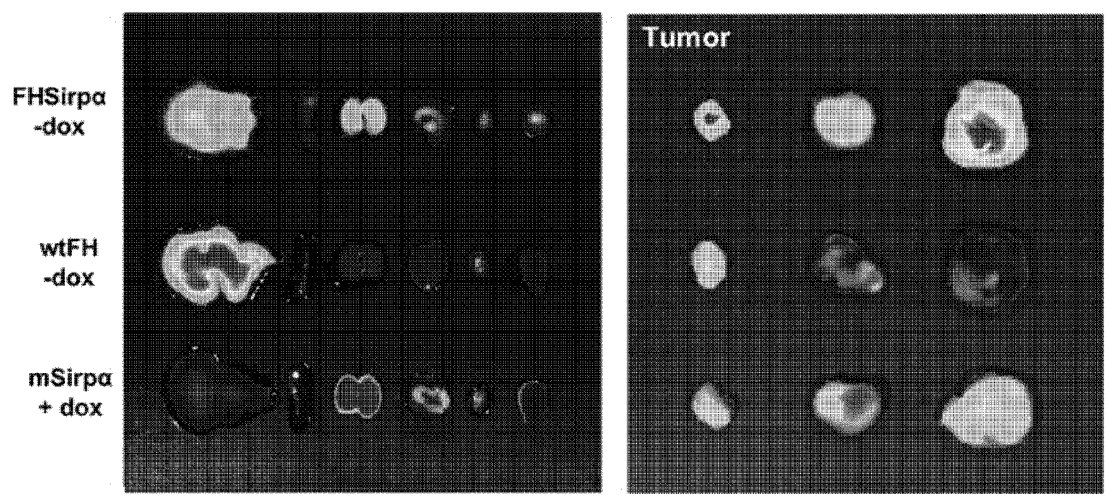
Figure 10D:
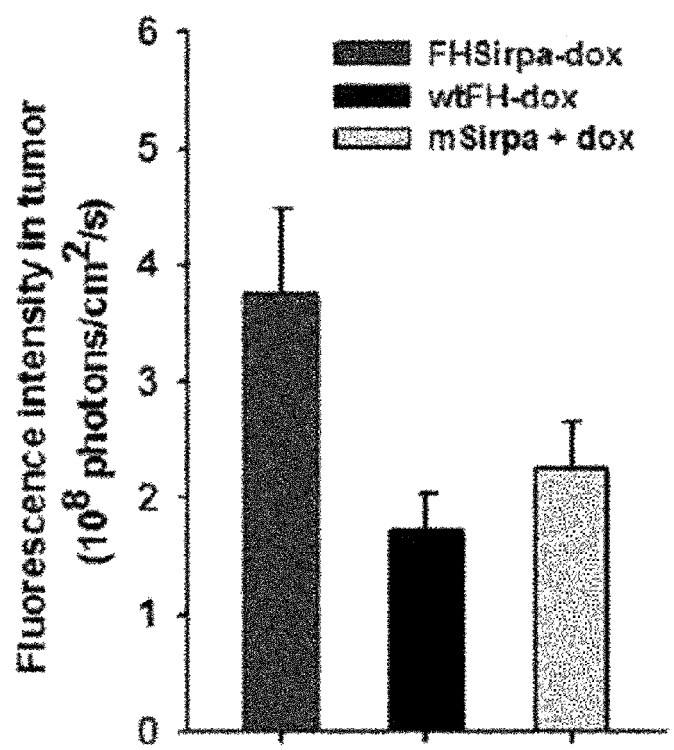

As a result, as shown in FIGS. 9A and 9C, no animal whose tumor grew was observed in the group administered with doxorubicin-loaded FH-SIRPα HV-dox nanocage complex according to an embodiment of the present invention until 28 days passed, while other groups of mice administered with other substances showed cancer recurrence although there was some difference in the degree of recurrence over time. In addition, as shown in FIG. 9B, the survival rate of the same experimental group after 80 days of tumor rechallenge was investigated, and no animals was died after 80 days in the doxorubicin-loaded FH-SIRPα HV-dox nanocage complex group. Survival rate of SIRPα HV nanocage group was 80% after 80 days which was better after FH-SIRPα HV-dox nanocage complex and survival rate of doxorubicin alone group or recombinant SIRPα alone group was 50%.

The above results suggest that the nanocage according to an embodiment of the present invention not only inhibits the growth of cancer cells but also provides a memory effect on immune cells which can inhibit recurrence after treatment of cancer. Therefore, the nanocage according to an embodiment of the present invention can be very effective not only for treating cancer, but also for suppressing recurrence.

Experimental Example 5: Near Infrared Fluorescence System and Tumor

The present inventors investigated in vivo biodistribution (n=4 mice/group) of Cy5.5-labeled FH-SIRPα HV-dox using eXplore Optix System (Advanced Research Technologies Inc., USA). The delivery efficiency of FH-SIRPα HV-dox to the tumor microenvironment was observed. First, for Cy5.5 conjugation, Cy5.5-NHS and FH-SIRPα-dox, wtFH-dox or mSIRPα were mixed at a molar ratio of 1:24 in 0.1 M sodium bicarbonate (pH 8.5) and cultured for 16 hours. The fee Cy5.5 was then removed and the buffer was exchanged with PBS by ultrafiltration (Amicon Ultra 100K; Millipore). The fluorescence intensity of hFTH labeled with Cy5.5 was measured using a fluorescent microplate reader (Infinite M200 Pro, TECAN, Austria). Cy5.5-labeled FH-SIRPα HV-dox, wtFH-dox, or mSIRPα-dox were intravenously injected into CT26.CL25 tumor-bearing Balb/c mice (100 μL/mouse) via tail vein. Fluorescence intensity of all samples was adjusted to the same value based on data obtained using a fluorescence microplate reader and the in vive systemic imaging of the mice was performed at various time points using the eXplore Optix System (Advanced Research Technologies Inc.).

For quantitative analysis of fluorescence intensity, near infrared fluorescence intensity (total photons/cm$^2$/steradian) of tumor tissue was calculated by ROI analysis using Analysis Workstation software (Advanced Research Technologies, Inc.) and mice were sacrificed 24 hours after injection and tumors and major organs including liver, lung, spleen, kidney, heart, and intestines were excised and imaged using a KODAK Image Station (4000 MM, Kodak, USA).

As a result, as shown in FIGS. 10A to 10D, higher near-infrared fluorescence intensity was exhibited in the FH-SIRPα HV-dox group as compared with the wtFH-dox or mSIRPα-dox group over time.

These results demonstrate that the FH-SIRPα nanocage according to an embodiment of the present invention not only inhibits cancer cell growth, but also promotes memory of anti-cancer activity of immune cells, thereby inhibiting cancer recurrence. Therefore, the FH-SIRPα HV-dox nanocage complex with the FH-SIRPα nanocage and the anthracycline anticancer drug loaded according to an embodiment of the present invention can be developed as a highly effective drug for the prevention of cancer treatment and recurrence.

While the present invention has been described with reference to exemplary embodiments, it is to be understood that the invention is not limited to the disclosed exemplary embodiments, but, on the contrary, is intended to cover various modifications and equivalent arrangements included within the spirit and scope of the appended claims. Accordingly, the true scope of the present invention should be determined by the technical idea of the appended claims

What is claimed is:

1. A pharmaceutical composition for treating cancer comprising as an active ingredient a nanocage formed by self-assembly of a fusion protein comprising a phagocytosis enhancing protein and a self-assembling protein, wherein the phagocytosis enhancing protein is linked to the N-terminus or C-terminus of the self-assembling protein directly or via a linker peptide, optionally wherein the nanocage is provided as a nanocage complex in which an immunogenic cell death inducer is encapsulated in the nanocage.

2. The pharmaceutical composition of claim 1, wherein the nanocage is a hybrid nanocage formed by self-assembly of a first fusion protein comprising the phagocytosis enhancing protein and the self-assembling protein, wherein the phagocytosis enhancing protein is linked to the N-terminus or C-terminus of the self-assembling protein directly or via a linker peptide, and a second fusion protein comprising a single chain-based antibody analogue targeting an immune checkpoint and the self-assembling protein.

3. The pharmaceutical composition according to claim 1, wherein the phagocytosis enhancing protein is selected from SIRPα, SIRPγ, surfactant protein A, surfactant protein D, and anti-CD47 antibody.

4. The pharmaceutical composition according to claim 1, wherein the self-assembling protein is selected from a small heat shock protein (sHsp), ferritin, vault, P6HRC1-SAPN, M2e-SAPN, MPER-SAPN, a viral capsid protein, and a bacteriophage capsid protein.

5. The pharmaceutical composition of claim 4, wherein the ferritin is a ferritin heavy chain protein or a ferritin light chain protein.

6. The pharmaceutical composition of claim 4, wherein said viral or bacteriophage capsid protein is selected from the group consisting of bacteriophage MS2 capsid protein, bacteriophage P22 capsid protein, Qβ bacteriophage capsid protein, CCMV capsid protein, CPMV capsid protein, RCNMV capsid protein, ASLV capsid protein, HCRSV capsid protein, HJCPV capsid protein, A SHIV capsid protein, an MPV capsid protein, an SV40 capsid protein, an HIV capsid protein, an HBV capsid protein, an adenovirus capsid protein, and a rotavirus VP6 protein.

7. The pharmaceutical composition according to claim 1, wherein the fusion protein comprises a linker peptide between the phagocytosis enhancing protein and the self-assembling protein.

8. The pharmaceutical composition according to claim 1, wherein the immunogenic cell death inducer is selected from the group consisting of an anthracycline-based anticancer agent, a taxanoid anticancer agent, an anti-EGFR antibody, a BK channel agonist, bortezomib, cardiac glycoside, a cyclophosphamide anticancer agent, a GADD34/PP1 inhibitor, LV-tSMAC, Measles virus, and oxaliplatin.

9. The pharmaceutical composition of claim 8, wherein the anthracycline-based anticancer agent is selected from the group consisting of daunorubicin, doxorubicin, epirubicin, idarubicin, pixantrone, sabarubicin, and valrubicin.

10. The pharmaceutical composition of claim 8, wherein the immunogenic cell death inducer comprises a cardiac glycoside and the composition further comprises a non-immunogenic apoptosis inducing agent.

11. The pharmaceutical composition of claim 8, wherein the immunogenic cell death inducer comprises a GADD34/PP1 inhibitor and the composition further comprises mitomycin.

12. The pharmaceutical composition of claim 8, wherein the taxanoid anticancer agent is paclitaxel or docetaxel.

13. The pharmaceutical composition according to claim 1, further comprising an immune checkpoint inhibitor.

14. The pharmaceutical composition according to claim 13, wherein said immune checkpoint inhibitor is a PD-1/PD-L1 interaction inhibitor or a CTLA-4/B7-1/B7-2 interaction inhibitor.

15. The pharmaceutical composition of claim 14, wherein the PD-1/PD-L1 interaction inhibitor is Pembrolizumab, Nivolumab, Atezolizumab or Avelumab.

16. The pharmaceutical composition of claim 14, wherein the CTLA-4/B7-1/B7-2 interaction inhibitor is Ipilimumab.

17. The pharmaceutical composition of claim 2, wherein the single chain-based antibody analogue is selected from a scFv, a sdAb, a diabody, a monobody, a variable lymphocyte receptor (VLR), a nanobody, and a camelid immunoglobulin heavy chain fragment ($V_H$H).

18. A fusion protein comprising SIRPα (signal-regulatory protein alpha) or SIRPγ linked to the N terminus or C-terminus of a ferritin heavy chain protein, wherein the fusion protein comprises the amino acid sequence of any one of SEQ ID NOS: 1-11.

19. The fusion protein of claim 18, wherein the SIRPα is composed of the amino acid sequence of any one of SEQ ID NOS: 12 to 64.

20. The fusion protein of claim 18, wherein the SIRPγ comprises the amino acid sequence of SEQ ID NO: 98 or 100.

21. A polynucleotide encoding the fusion protein of claim 18.

22. A recombinant vector comprising the polynucleotide of claim 21.

23. A transformed host cell prepared by transforming a host cell with the vector of claim 22.

24. A protein nanocage produced by self-assembly of the fusion protein of claim 18.

25. An anticancer protein nanocage complex encapsulated with an immunogenic apoptosis inducer in the protein nanocage of claim 24.

26. The anticancer protein nanocage complex of claim 24, wherein the immunogenic cell death inducer is selected from the group consisting of an anthracycline-based anticancer agent, a taxanoid anticancer agent, an anti-EGFR antibody, a BK channel agonist, bortezomib, cardiac glycoside, a cyclophosphamide anticancer agent, a GADD34/PP1 inhibitor, LV-tSMAC, Measles virus, and oxaliplatin.

27. A pharmaceutical composition for anti-cancer comprising the anticancer protein nanocage of claim 24 as an active ingredient.

* * * * *